(12) United States Patent
Nagayama et al.

(10) Patent No.: US 12,247,040 B2
(45) Date of Patent: Mar. 11, 2025

(54) IRIDIUM COMPLEX COMPOUND

(71) Applicant: Mitsubishi Chemical Corporation, Tokyo (JP)

(72) Inventors: Kazuhiro Nagayama, Tokyo (JP); Hideji Komatsu, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 813 days.

(21) Appl. No.: 17/305,164

(22) Filed: Jul. 1, 2021

(65) Prior Publication Data

US 2021/0323986 A1 Oct. 21, 2021

Related U.S. Application Data

(63) Continuation of application No. PCT/JP2020/000269, filed on Jan. 8, 2020.

(30) Foreign Application Priority Data

Jan. 10, 2019 (JP) ................................. 2019-002398
Oct. 7, 2019 (JP) ................................. 2019-184629

(51) Int. Cl.
*C09K 11/06* (2006.01)
*C07F 15/00* (2006.01)

(52) U.S. Cl.
CPC .......... *C07F 15/0033* (2013.01); *C09K 11/06* (2013.01); *C09K 2211/1029* (2013.01); *C09K 2211/185* (2013.01)

(58) Field of Classification Search
CPC ............................. C07F 15/033; C09K 11/06
See application file for complete search history.

(56) References Cited

U.S. PATENT DOCUMENTS

| | | | |
|---|---|---|---|
| 2008/0210930 A1 | 9/2008 | Kamatani et al. | |
| 2009/0179555 A1 | 7/2009 | Kim et al. | |
| 2016/0293866 A1 | 10/2016 | Ishibashi et al. | |
| 2018/0351114 A1 | 12/2018 | Kim et al. | |
| 2019/0221758 A1 | 7/2019 | Kim et al. | |
| 2020/0317706 A1 | 10/2020 | Nagayama et al. | |

FOREIGN PATENT DOCUMENTS

| | | | |
|---|---|---|---|
| CN | 101508673 A | 8/2009 | |
| CN | 102648203 A | 8/2012 | |
| EP | 2 062 959 A2 | 5/2009 | |
| EP | 2 062 959 A3 | 5/2009 | |
| JP | 2006-151888 A | 6/2006 | |
| JP | 2009173630 A * | 8/2009 | .......... C07F 15/0033 |
| TW | 201336853 A | 9/2013 | |
| WO | WO 2015/087961 A1 | 6/2015 | |
| WO | WO 2017/099516 A1 | 6/2017 | |

(Continued)

OTHER PUBLICATIONS

Chinese Office Action issued Mar. 28, 2024 in Chinese Patent Application No. 202080008778.0 (with unedited computer-generated English translation), 13 pages.
Combined Taiwanese Office Action and Search Report issued on May 15, 2023 in Taiwanese Patent Application No. 109100827 (with unedited computer-generated English translation), 9 pages.
International Search Report issued Feb. 25, 2020 in PCT/JP2020/000269 filed on Jan. 8, 2020, 3 pages.
Japanese Office Action issued Jan. 16, 2024, in Japanese Application 2020-565173, (with unedited computer-generated English translation), 6 pages.
Combined Chinese Office Action and Search Report issued Oct. 23, 2023 in Chinese Application 202080008778.0, (with unedited computer-generated English translation), 11 pages.

(Continued)

*Primary Examiner* — John S Kenyon
(74) *Attorney, Agent, or Firm* — Oblon, McClelland, Maier & Neustadt, L.L.P.

(57) ABSTRACT

An iridium complex compound represented by formula (5):

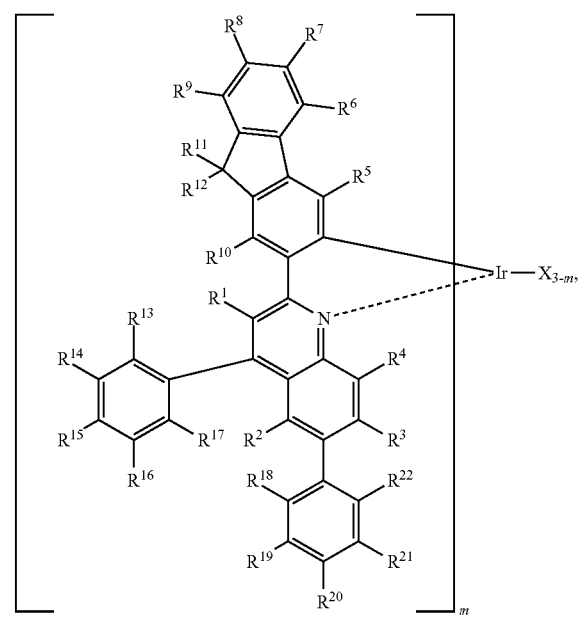

formula (5)

where in formula (5), Ir represents an iridium atom, $R^1$ to $R^{12}$ each independently represent a hydrogen atom or a substituent, adjacent $R^1$ to $R^{12}$ are optionally bonded together to form a ring, $R^{13}$ to $R^{22}$ each independently represent a hydrogen atom or a substituent, adjacent $R^{13}$ to $R^{22}$ are optionally bonded together to form a ring, X represents a bidentate ligand, m represents an integer of 1 to 3, and at least one of $R^{13}$, $R^{17}$, $R^{18}$, and $R^{22}$ represents a substituent other than a hydrogen atom.

13 Claims, 3 Drawing Sheets

(56) References Cited

FOREIGN PATENT DOCUMENTS

| WO | WO 2018/062758 A1 | 4/2018 |
| WO | WO 2018/062758 A9 | 4/2018 |
| WO | WO 2018/066583 A1 | 4/2018 |
| WO | WO 2019/093369 A1 | 5/2019 |

OTHER PUBLICATIONS

Extended European Search Report issued Jan. 27, 2022 in corresponding European Patent Application No. 20738629.3, 7 pages.
Chinese Office Action issued Jun. 28, 2024 in Chinese Patent Application 202080008778.0 (with unedited computer-generated English translation), 12 pages.

* cited by examiner

IRIDIUM COMPLEX COMPOUND

TECHNICAL FIELD

The present invention relates to an iridium complex compound, and in particular, to an iridium complex compound useful as a material for a light-emitting layer of an organic electroluminescent element (hereinafter also referred to as an "organic EL element").

BACKGROUND ART

Organic electroluminescent elements are produced by stacking multiple layers, such as a light-emitting layer, a charge injection layer, and a charge transport layer. Currently, most of the organic electroluminescent elements are produced by depositing organic materials under vacuum. Vacuum deposition methods have complicated deposition processes and poor productivity. It is very difficult to provide a large-sized panel for an illuminator or a display including an organic electroluminescent element produced by a vacuum deposition method. For this reason, in recent years, wet film-forming methods (application methods) have been actively studied as processes for efficiently producing organic electroluminescent elements that can be used in large-sized displays and illuminators.

To produce an organic electroluminescent element by a wet film-forming method, materials used each need to be capable of being used in the form of an ink containing the material dissolved in an organic solvent. In the case where each of the materials used has poor solvent solubility, the material may deteriorate before use because of the need for operations, such as long-time heating. When the solution of the material used cannot be maintained at a homogeneous state for a long period of time, the material precipitates out of the solution, failing to forming a film, for example, with an inkjet apparatus.

Materials used in a wet film-forming method each need to have solubility in two meanings: the material dissolves rapidly in an organic solvent; and the material does not precipitate after the dissolution and maintains the homogeneous state.

In recent years, there has been an increasing demand for the formation of a thicker light-emitting layer in order to extend the operating lifetimes of elements and to improve color purity by optimizing the optical design of elements to effectively provide what is called a microcavity effect. To form a thick light-emitting layer, it is necessary to increase the density of an ink. This requires a light-emitting material having higher solvent solubility than conventional ones.

Organic EL displays are required to have high light emission efficiency in addition to a long operating lifetime and a wide gamut, i.e., a high color reproduction rate. In particular, the red region is required to have a considerably deep red color with an x-coordinate of 0.68 in the coordinates in the XYZ colorimetric system defined by the Commission Internationale de l'Eclairage (CIE). To produce such a deep red color, the maximum emission wavelength of a light-emitting material needs to be longer (for example, 620 nm or more). In this wavelength region, a law called the energy gap law governs. In this wavelength region, the percentage of the dissipation of the excitation energy into molecular motion, i.e., thermal energy, rather than light emission increases as the wavelength lengthens. The emission quantum yield at longer wavelengths deteriorates significantly. In the red region, thus, it is difficult to achieve a deeper red color and a higher efficiency of the luminescent quantum yield (cd/A) at the same time.

The human visual sensitivity also decreases greatly in the red region. For this reason, higher emission intensity is required in the deep red region.

There are two types of multilayer structures for organic EL displays that differ in light extraction direction.

In a bottom-emission structure, which seemingly made by a relatively simple production process, light generated from organic molecules emerges from a bottom surface adjacent to a TFT substrate, and the light utilization efficiency of organic molecules is disadvantageously low.

In contrast, in a top-emission structure, light emerges from a top glass seal with no pixel circuit or the like, so that emitted light can be efficiently emitted to the outside. However, in the case where the top-emission structure is used, light components having wavelengths other than a specific wavelength are reflected and canceled within the multilayer structure and thus are less likely to travel outside the multilayer structure. For this reason, in the case where the emission spectrum of a light-emitting material has a large half-width, light components having wavelengths other than a specific wavelength are less likely to travel outside the multilayer structure, thus resulting in a decrease in light emission efficiency.

As described above, a red light-emitting material is required to have the following properties: high solubility in a solvent, high light emission efficiency even at a long wavelength, and a narrow half-width of the emission spectrum.

As red light-emitting materials, iridium complex compounds that inherently phosphoresce with high efficiency have been used. In particular, iridium complex compounds having phenyl-quinoline-type ligands, as described in PTLs 1 and 2, have been widely used.

PTL 1 discloses compounds in which two ligands having fluorene and quinoline coordinate to iridium, for example, structural formulae A1 to A58.

PTL 2 discloses compounds in which two ligands having an aromatic group-containing quinoline and fluorene coordinate to iridium, for example, compound Nos. 12 and 189.

PTL 1: JP2006-151888A
PTL 2: JP2009-173630A

In the iridium complexes having the fluorene structures as disclosed in PTL 1, the light emission thereof is mainly based on ligand centered (LC)-type emission with less contribution of iridium atoms, and the difference in electric dipole moment between an excited state and a ground state is small because of intraligand transitions. This typically results in a narrow half-width. Meanwhile, the solubility thereof is greatly decreased because of the rigid structure of fluorene. Additionally, as a result of the small contribution of the d orbitals of iridium, the light emission efficiency is disadvantageously decreased.

For example, compound No. 12 described in PTL 2 has poor solubility and an insufficient half-width. Ligands with phenyl group-containing quinoline and fluorene, as in compound No. 6 in PTL 2, are effective against the issue of the half-width to a certain extent and also effective for the quantum yield to a certain extent. However, the use of such ligands results in longer maximum emission wavelengths, which is especially problematic for red light-emitting materials.

SUMMARY OF INVENTION

It is an object of the present invention to provide an iridium complex compound that exhibits a narrow half-width of the emission spectrum thereof, has high solubility in a solvent, has light emission efficiency performance higher than or equivalent to conventional materials, does not have an excessively long maximum emission wavelength, and is suitable as a red light-emitting material.

The inventors have found that an iridium complex compound having a specific chemical structure does not have an excessively long maximum emission wavelength as a red-light-emitting material, has extremely higher solvent solubility than conventional materials, and exhibits a high PL quantum yield and a narrow half-width.

The present invention refers to an iridium complex compound described below.

[1] An iridium complex compound represented by formula (5):

[Chem. 1]

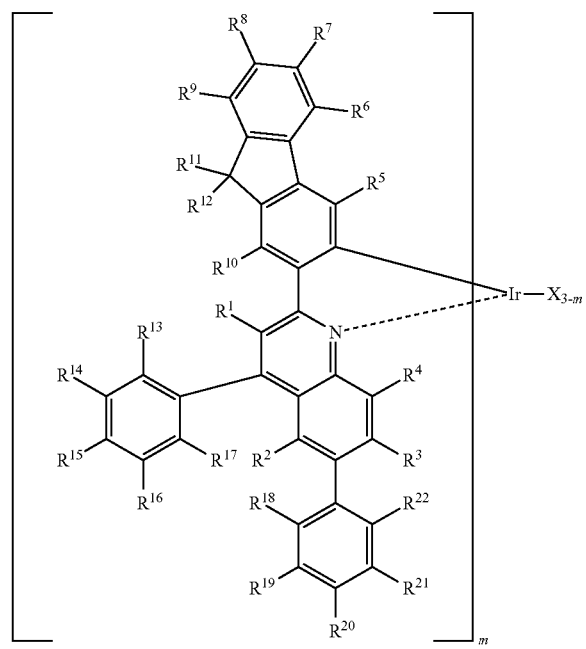

formula (5)

where in formula (5), Ir represents an iridium atom, $R^1$ to $R^{12}$ each independently represent a hydrogen atom or a substituent;

adjacent $R^1$ to $R^{12}$ are optionally bonded together to form a ring;

$R^{13}$ to $R^{22}$ each independently represent a hydrogen atom or a substituent;

adjacent $R^{13}$ to $R^{22}$ are optionally bonded together to form a ring;

X represents a bidentate ligand;

m represents an integer of 1 to 3, and;

at least one of $R^{13}$, $R^{17}$, $R^{19}$, and $R^{22}$ represents a substituent other than a hydrogen atom.

[2] The iridium complex compound according to [1], wherein formula (5) is represented by formula (2):

[Chem. 2]

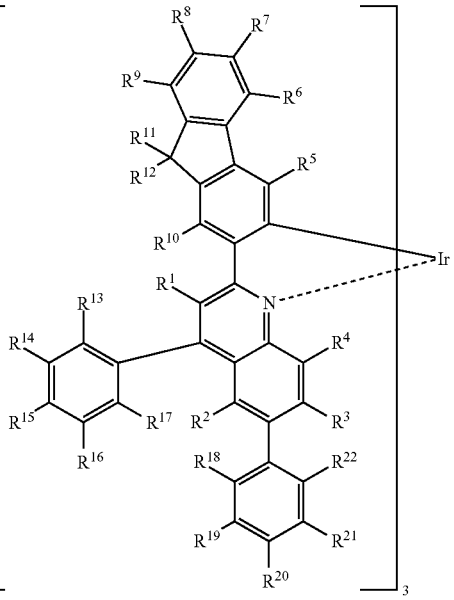

formula (2)

where in formula (2), $R^1$ to $R^{22}$ are defined the same as in formula (5).

[3] The iridium complex compound according to [1] or [2], wherein $R^1$ to $R^{12}$, and $R^{13}$ to $R^{22}$ are as follows:

$R^1$ to $R^{12}$ are each independently selected from D, F, Cl, Br, I, —N(R')$_2$, —CN, —NO$_2$, —OH, —COOR', —C(=O)R', —C(=O)NR', —P(=O) (R')$_2$, —S(=O) R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(—R')=C(—R')—, —C≡C—, —Si(—R')$_2$, —C(=O)—, —NR'—, —O—, —S—, —CONR'— or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R';

adjacent $R^1$ to $R^{12}$ are optionally bonded together to form a ring;

each R' is independently selected from a hydrogen atom, D, F, Cl, Br, I, —N(R")$_2$, —CN, —NO$_2$, —Si(R")$_3$, —B(OR")$_2$, —C(=O)R", —P(=O) (R")$_2$, —S(=O)$_2$R", —OSO$_2$R", a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R", one —CH$_2$— group or two or more non-adjacent —CH$_2$— groups in these groups are each optionally replaced with —C(—R")=C(—R")—, —C≡C—, —Si(—R")$_2$—, —C(=O)—, —NR"—, —O—, —S—, —CONR"—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R";

two or more R' are optionally bonded together to form an aliphatic, aromatic, or heteroaromatic, monocyclic or fused ring;

each R" is independently selected from a hydrogen atom, D, F, —CN, an aliphatic hydrocarbon group having 1 to 20 carbon atoms, an aromatic group having 3 to 20 carbon atoms, and a heteroaromatic group having 1 to 20 carbon atoms;

two or more R" are optionally bonded together to form an aliphatic, aromatic, or heteroaromatic, monocyclic or fused ring; and $R^{13}$ to $R^{22}$ are each independently a hydrogen atom or a substituent represented by R'.

[4] The iridium complex compound according to [1] or [3], wherein in formula (5), two or more adjacent $R^1$ to $R^{10}$, $R^{11}$ and $R^{12}$, two or more adjacent $R^{13}$ to $R^{17}$, or two or more adjacent $R^{18}$ to $R^{22}$ are bonded together to form an aliphatic, aromatic, or heteroaromatic, monocyclic or fused ring.

[5] The iridium complex compound according to [1], [3], or [4], wherein formula (5) is represented by formula (6):

[Chem. 3]

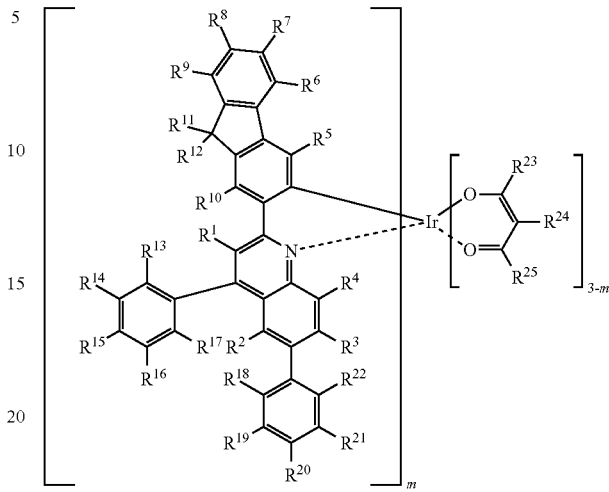

formula (6)

where in formula (6), $R^1$ to $R^{22}$, and m are defined the same as in formula (5);

$R^{23}$ and $R^{25}$ are each independently selected from —N(R')$_2$, —COOR', —C(=O)R', —C(=O)NR', —P(=O) (R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

$R^{24}$ is selected from a hydrogen atom, D, —N(R')$_2$, —COOR', —C(=O)R', —C(=O)NR', —P(=O) (R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

two or more adjacent $R^{23}$ to $R^{25}$ are optionally bonded together to form an aliphatic, aromatic, or heteroaromatic, monocyclic or fused ring;

the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(—R')═C(—R')—, —C≡C—, —Si(—R')$_2$, —C(═O)—, —NR'—, —O—, —S—, —CONR'—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R'; and when $R^{23}$ to $R^{25}$ each have R', R' is the same as R' in formula (5).

[6] The iridium complex compound according to any one of [1] to [5], wherein at least one of $R^1$ to $R^4$ and $R^{13}$ to $R^{22}$ in formula (2), (5), or (6) contains an alkyl group having 4 to 30 carbon atoms or an aralkyl group having 5 to 30 carbon atoms.

[7] The iridium complex compound according to any one of [1] to [6], wherein at least one or more of the substituents $R^{13}$, $R^{17}$, $R^{18}$, and $R^{22}$ in formula (2), (5), or (6) each optionally have an alkyl group having 1 to 4 carbon atoms or an optionally substituted aromatic group.

[8] The iridium complex compound according to [7], wherein each of the substituents $R^{18}$ and $R^{22}$ in formula (2), (5), or (6) is an alkyl group having 1 to 4 carbon atoms.

[9] The iridium complex compound according to any one of [1] to [8], wherein at least one or more of the substituents $R^{14}$, $R^{15}$, $R^{16}$, $R^{19}$, $R^{20}$, and $R^{21}$ in formula (2), (5), or (6) is an alkyl group, an optionally substituted aromatic ring group, or an aralkyl group.

[10] The iridium complex compound according to [9], wherein at least one or more of the substituents $R^{14}$, $R^{15}$, $R^{16}$, $R^{19}$, $R^{20}$, and $R^{21}$ in formula (2), (5), or (6) are each a substituted aromatic ring group, and the substituent is an aralkyl group.

[11] The iridium complex compound according to [10], wherein the iridium complex compound is represented by formula (3):

[Chem. 4]

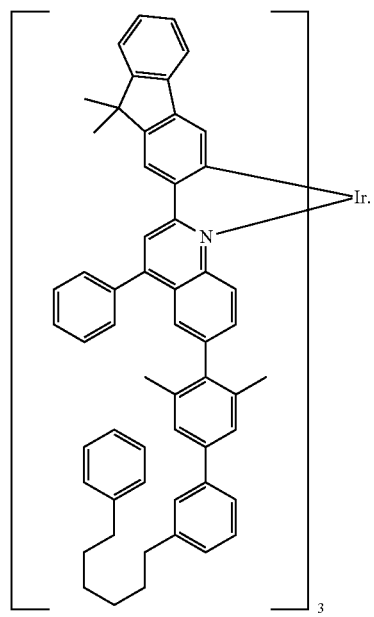

formula (3)

[12] The iridium complex compound according to any one of [1] to [10], wherein at least one or more of the substituents $R^{13}$, $R^{17}$, $R^{18}$, and $R^{22}$ in formula (2), (5), or (6) are each a substituted aromatic ring group, and the substituent is an aralkyl group.

[13] The iridium complex compound according to [12], wherein the iridium complex compound is represented by formula (4):

[Chem. 5]

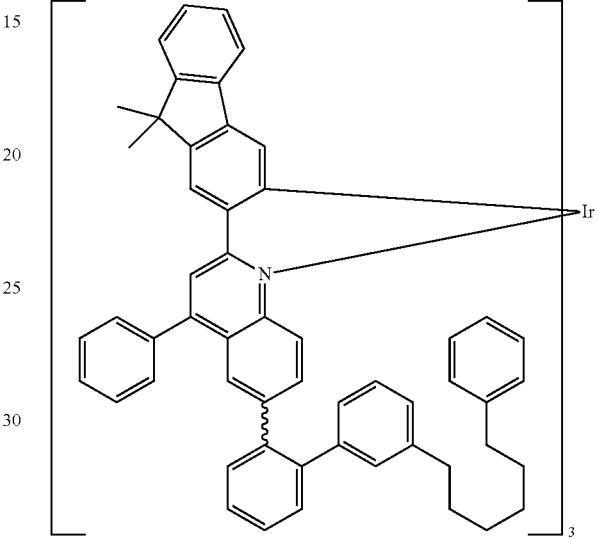

formula (4)

where in formula (4), a wiggly line indicates a mixture of rotamers.

ADVANTEGEOUS EFFECTS OF INVENTION

According to the present invention, it is possible to provide the iridium complex compound that exhibits a narrow half-width of the emission spectrum thereof, has high solubility in a solvent, has light emission efficiency performance higher than or equivalent to conventional materials, does not have an excessively long maximum emission wavelength, and is suitable as a red-light-emitting material.

DESCRIPTION OF EMBODIMENTS

Figure 1:
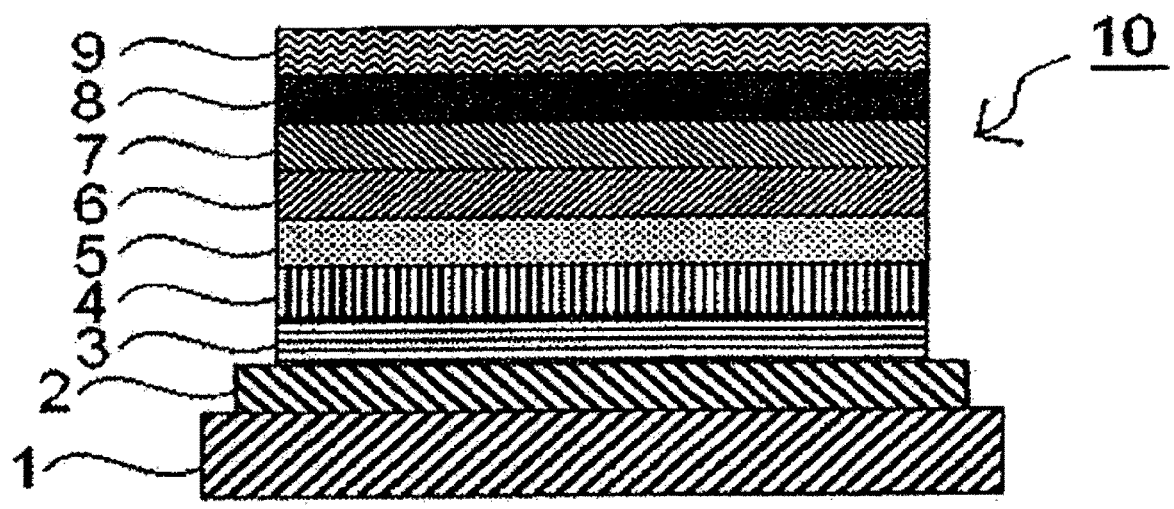
FIG. 1 is a sectional view schematically illustrating an example of a structure of an organic electroluminescent element of the present invention.

Embodiments of the present invention will now be described in detail, but the present invention is not limited to the following embodiments and can be practiced with various modifications within the scope of the gist of the invention.

As used herein, the term "aromatic ring" refers to an "aromatic hydrocarbon ring" and is distinct from a "heteroaromatic ring" which includes a heteroatom as an annular atom. Similarly, the term "aromatic group" refers to an "aromatic hydrocarbon ring group", and the term "heteroaromatic group" refers to a "heteroaromatic ring group".

[Iridium Complex Compound]

An iridium complex compound of the present invention is a compound represented by formula (1), (2), (5), or (6) described below.

[Chem. 6]

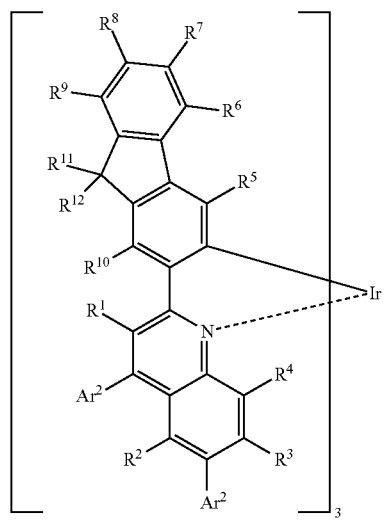

formula (1)

In formula (1), Ir represents an iridium atom. $Ar^1$ and $Ar^2$ each represent an optionally substituted aromatic ring or heteroaromatic ring. $R^1$ to $R^{12}$ each independently represent a hydrogen atom or a substituent, and adjacent substituents may be bonded together to form a ring.

[Chem. 7]

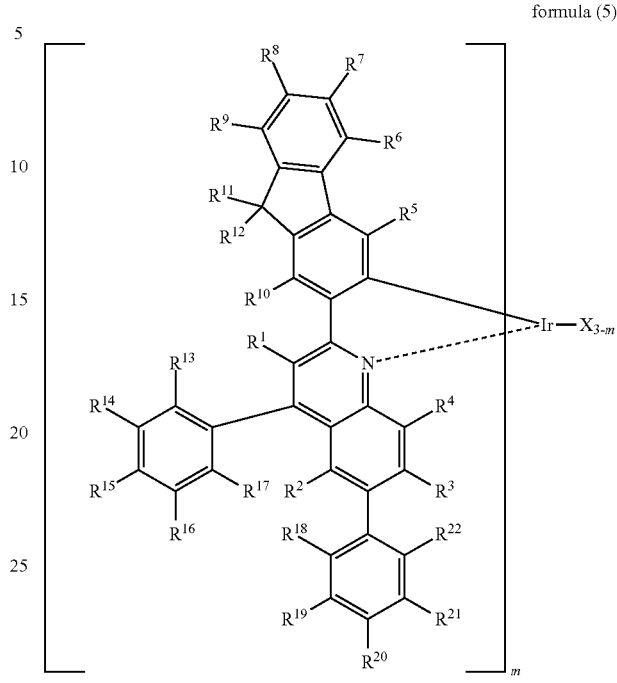

formula (5)

where in formula (5), Ir represents an iridium atom, $R^1$ to $R^{12}$ each independently represent a hydrogen atom or a substituent;

adjacent $R^1$ to $R^{12}$ are optionally bonded together to form a ring;

$R^{13}$ to $R^{22}$ each independently represent a hydrogen atom or a substituent;

adjacent $R^{13}$ to $R^{22}$ are optionally bonded together to form a ring;

X represents a bidentate ligand;

m represents an integer of 1 to 3, and;

at least one of $R^{13}$, $R^{17}$, $R^{18}$, and $R^{22}$ represents a substituent other than a hydrogen atom.

The compound represented by formula (1) according to a more preferred embodiment is a compound represented by formula (2) below.

[Chem. 8]

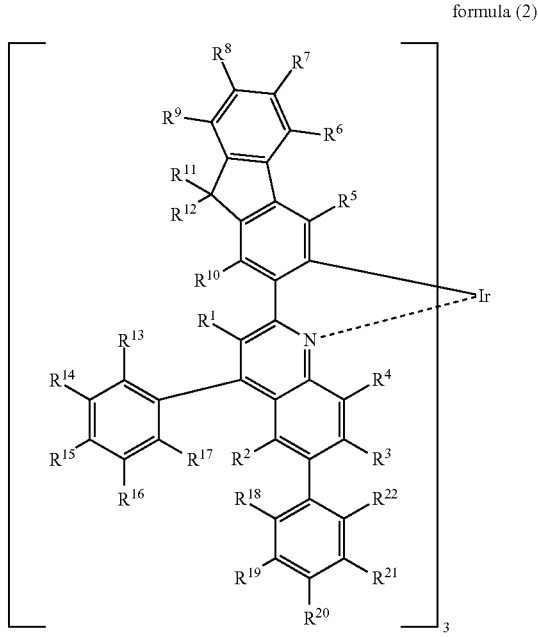

formula (2)

$R^1$ to $R^{12}$ are defined the same as $R^1$ to $R^{12}$ in formula (1), (5). $R^{13}$ to $R^{22}$ are defined the same as $R^{13}$ to $R^{22}$ in formula (5).

The possible reasons why the iridium complex compounds of the present invention do not have an excessively long maximum emission wavelength as red light-emitting materials, have extremely higher solvent solubility than conventional materials, and exhibit light emission efficiency equivalent to conventional materials and narrow half-widths are described below.

Fluorene in formula (1), (2), or (5) has a high electron-donating ability because of the effect of the electron-donating properties of a methylene group and the rigidly immobilized π-conjugate plane. This serves to raise the HOMO level of the ligand to suppress the inflow of d-electrons from the iridium atom. Thus, the metal-to-ligand charge-transfer (MLCT) properties are decreased, and the LC properties are promoted. In the LC-type emission with less contribution of iridium atoms, the difference in electric dipole moment between an excited state and a ground state is small because of intraligand transitions, thus resulting in a narrow half-width.

However, the small contribution of the d orbitals results in a small phosphorescence radiative rate constant kr of the light-emitting material, thus decreasing the light emission efficiency (see "Selected Books for the Japan Society of Coordination Chemistry 2, Photochemistry in Metal Complexes", edited by Yoichi SASAKI and Osamu ISHITANI, Sankyo Shuppan Co., Ltd. (2007), Chapter 4).

The use of a homoleptic tris-cyclometalated complex of trivalent iridium coordinated with three identical ligands ($L_3Ir$) can narrow the half-width (formula (1) or (2)). Unlike a similar heteroleptic tris-cyclometalated complex of iridium coordinated with different ligands ($L^1_2L^2Ir$, $L^1L^2_2Ir$, or $L^1L^2L^3Ir$) that affect each other, the homoleptic complex does not have such a problem. Thus, the quantum yield tends to be better in this respect. Meanwhile, since the contribution of the d orbitals is small as described above, the quantum yield is decreased in this respect.

The inventors have found that in a three-coordinate iridium complex with fluorene ligands, the quantum yield can be improved by introducing an appropriate substituent at a specific position of each quinoline ring while a narrow half-width offered by fluorene, which is a desirable property, is not impaired. Specifically, it was found that the introduction of aromatic ring groups at both of the 4- and 6-positions of the quinoline ring extends the conjugation of the ligand to reduce the LUMO of the ligand, thereby increasing the proportion of excitation from the d-orbitals of iridium to recover the quantum yield.

Additionally, the introduction of the aromatic ring groups at the 4- and 6-positions of the quinoline ring increases the molecular size, thus increasing the number of possible conformations between the quinoline and the aromatic ring groups. For this reason, crystallization is less likely to occur, thus also leading to an increase in solubility. Here, the introduction of one aromatic ring group into the quinoline ring moiety is not sufficient. The introduction of the aromatic ring group at each of the 4-position and the 6-position is presumably important.

Even in the cases of homoleptic tris-cyclometalated Ir complexes where each trivalent iridium is coordinated with three identical ligands, such as m=3 in formulae (1), (2), and (5), the interaction acted between the three identical ligands is such that the half-width is slightly larger. For this reason, the half-width can seemingly be further narrowed by use of a bis-cyclometalated complex in which at least one of the three ligands is a ligand that does not easily interact with the other two ligands, such as m=1 or 2 in formula (5).

In the case where at least one of $R^{13}$, $R^{17}$, $R^{18}$ and $R^{22}$ in formula (2) or (5) is a substituent other than a hydrogen atom, a twist can be formed between the quinoline ring and the benzene ring bonded to the quinoline ring, thus shortening the conjugation length, improving the solubility, and suppressing the lengthening of the wavelength. This makes it possible to provide a suitable compound as a red light-emitting material that does not have an excessively long maximum emission wavelength.

<$Ar^1$ and $Ar^2$>

$Ar^1$ and $Ar^2$ each represent an aromatic ring or a heteroaromatic ring and may be the same or different. These rings may further have substituents. The types thereof are defined the same as $R^{13}$ to $R^{22}$ described below.

The number of carbon atoms constituting $Ar^1$ or $Ar^2$ is, excluding the carbon atoms of the substituent, usually 4 to 60, preferably 4 to 40, more preferably 5 to 20, in view of the solubility and the maximum emission wavelength affected by conjugate extension.

Specific examples of $Ar^1$ or $Ar^2$ include aromatic rings, such as monocyclic rings, e.g., a benzene ring; bicyclic rings, e.g., a naphthalene ring; and tri- or higher cyclic rings, e.g., a fluorene ring, an anthracene ring, a phenanthrene ring, a perylene ring, a tetracene ring, a pyrene ring, a benzpyrene ring, a chrysene ring, a triphenylene ring, and a fluoranthene ring. Specific examples thereof include heteroaromatic rings, such as oxygen-containing rings, e.g., a furan ring, a benzofuran ring, and a dibenzofuran ring; sulfur-containing rings, e.g., a thiophene ring, a benzothiophene ring, and a dibenzothiophene ring; nitrogen-containing rings, e.g., a pyrrole ring, a pyrazole ring, an imidazole ring, a benzimidazole ring, an indole ring, an indazole ring, a carbazole ring, an indolocarbazole ring, an indenocarbazole ring, a pyridine ring, a pyrazine ring, a pyridazine ring, a pyrimidine ring, a triazine ring, a quinoline ring, an isoquinoline ring, a cinnoline ring, a phthalazine ring, a quinoxaline ring, a quinazoline ring, a quinazolinone ring, an acridine ring, a phenanthridine ring, a carboline ring, and a purine ring; and rings including two or more different types of heteroatoms, e.g., an oxazole ring, an oxadiazole ring, an isoxazole ring, a benzisoxazole ring, a thiazole ring, a benzothiazole ring, an isothiazole ring, and a benzisothiazole ring.

In view of the solubility and the maximum emission wavelength affected by conjugate extension, preferred are a benzene ring, a naphthalene ring, an anthracene ring, a phenanthrene ring, a pyridine ring, a pyrimidine ring, a triazine ring, a quinoline ring, and an isoquinoline ring. More preferred are a benzene ring, a naphthalene ring, a phenanthrene ring, and a pyridine ring. A benzene ring is most preferred.

<$R^1$ to $R^{12}$>

$R^1$ to $R^{12}$ in formulae (1), (5), and (2) each represent a hydrogen atom or a substituent. $R^1$ to $R^{12}$ are independent of each other and may be the same or different.

Two or more adjacent $R^1$ to $R^{12}$ may be bonded together to form an aliphatic, aromatic, or heteroaromatic, monocyclic or fused ring.

When $R^1$ to $R^{12}$ are each a substituent other than a hydrogen atom, the types thereof are not particularly limited. An optimal substituent can be selected in view of, for example, precise control of the target emission wavelength, an affinity for a solvent used, and an affinity for a host compound in the case where an organic electroluminescent element is produced. In considering the optimization, preferred substituents are within the range described below.

$R^1$ to $R^{12}$ are each independently selected from D, F, Cl, Br, I, —N(R')$_2$, —CN, —NO$_2$, —OH, —COOR', —C(=O) R', —C(=O)NR', —P(=O) (R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(—R')=C(—R')—, —C≡C—, —Si(—R')$_2$, —C(=O)—, —NR'—, —O—, —S—, —CONR'— or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R';

R' will be described later.

PREFERRED EXAMPLES OF $R^1$ TO $R^{12}$

Examples of the linear, branched, or cyclic alkyl group that has 1 to 30 carbon atoms and that can be used as each of $R^1$ to $R^{12}$ include a methyl group, an ethyl group, an n-propyl group, an isopropyl group, an n-butyl group, an n-pentyl group, an n-hexyl group, an n-octyl group, a 2-ethylhexyl group, an isopropyl group, an isobutyl group, a cyclopentyl group, a cyclohexyl group, an n-octyl group, a norbornyl group, and an adamantyl group. From the viewpoint of durability, the number of carbon atoms is preferably 1 or more, and preferably 30 or less, more preferably 20 or less, most preferably 12 or less.

Examples of the linear, branched, or cyclic alkoxy group that has 1 to 30 carbon atoms and that can be used as each of $R^1$ to $R^{12}$ include a methoxy group, an ethoxy group, an n-propyloxy group, an n-butoxy group, an n-hexyloxy group, an isopropyloxy group, a cyclohexyloxy group, a 2-ethoxyethoxy group, and a 2-ethoxyethoxyethoxy group. From the viewpoint of durability, the number of carbon atoms is preferably 1 or more, and preferably 30 or less, more preferably 20 or less, most preferably 12 or less.

Examples of the linear, branched, or cyclic alkylthio group that has 1 to 30 carbon atoms and that can be used as each of $R^1$ to $R^{12}$ include a methylthio group, an ethylthio group, an n-propylthio group, an n-butylthio group, an n-hexylthio group, an isopropylthio group, a cyclohexylthio group, a 2-methylbutylthio group, and an n-hexylthio group. From the viewpoint of durability, the number of carbon atoms is preferably 1 or more, and preferably 30 or less, more preferably 20 or less, most preferably 12 or less.

Examples of the linear, branched, or cyclic alkenyl group that has 2 to 30 carbon atoms and that can be used as each of $R^1$ to $R^{12}$ include a vinyl group, an allyl group, a propenyl group, a heptenyl group, a cyclopentenyl group, a cyclohexenyl group, and a cyclooctenyl group. From the viewpoint of durability, the number of carbon atoms is preferably 2 or more, and preferably 30 or less, more preferably 20 or less, most preferably 12 or less.

Examples of the linear, branched, or cyclic alkynyl group that has 2 to 30 carbon atoms and that can be used as each of $R^1$ to $R^{12}$ include an ethynyl group, a propionyl group, a butynyl group, a pentynyl group, a hexynyl group, a heptynyl group, and an octynyl group. From the viewpoint of durability, the number of carbon atoms is preferably 2 or more, and preferably 30 or less, more preferably 20 or less, most preferably 12 or less.

The aromatic group having 5 to 60 carbon atoms and the heteroaromatic group having 3 to 60 carbon atoms, which can be used as each of $R^1$ to $R^{12}$ may be present in the form of a single ring or a fused ring, or may be a group formed through bonding or condensation between one ring and another type of aromatic group or heteroaromatic group.

Examples of such groups include a phenyl group, a naphthyl group, an anthracenyl group, a benzanthracenyl group, a phenanthrenyl group, a benzophenanthrenyl group, a pyrenyl group, a chrysenyl group, a fluoranthenyl group, a perylenyl group, a benzopyrenyl group, a benzofluoranthenyl group, a naphthacenyl group, a pentacenyl group, a biphenyl group, a terphenyl group, a fluorenyl group, a spirobifluorenyl group, a dihydrophenanthrenyl group, a dihydropyrenyl group, a tetrahydropyrenyl group, an indenofluorenyl group, a furyl group, a benzofuryl group, an isobenzofuryl group, a dibenzofuranyl group, a thiophene group, a benzothiophenyl group, a dibenzothiophenyl group, a pyrrolyl group, an indolyl group, an isoindolyl group, a carbazolyl group, a benzocarbazolyl group, an indolocarbazolyl group, an indenocarbazolyl group, a pyridyl group, a cinnolyl group, an isocinnolyl group, an acridyl group, a phenanthridyl group, a pyrazolyl group, an indazolyl group, an imidazolyl group, a benzimidazolyl group, a naphthoimidazolyl group, a phenanthroimidazolyl group, a pyridinimidazolyl group, an oxazolyl group, a benzoxazolyl group, a naphthoxazolyl group, a thiazolyl group, a benzothiazolyl group, a pyrimidyl group, a benzopyrimidyl group, a pyridazinyl group, a quinoxalinyl group, a diazaanthracenyl group, a diazapyrenyl group, a pyrazinyl group, a phenoxazinyl group, a phenothiazinyl group, a naphthyridinyl group, an azacarbazolyl group, a benzocarbolinyl group, a phenanthrolinyl group, a triazinyl group, and a 2,6-diphenyl-1,3,5-triazin-4-yl group.

From the viewpoint of the balance between solubility and durability, the number of carbon atoms in these groups is preferably 5 or more, and preferably 50 or less, more preferably 40 or less, most preferably 30 or less.

Preferred aromatic hydrocarbon groups are a phenyl group, a naphthyl group, an anthracenyl group, a phenanthrenyl group, a pyrenyl group, a chrysenyl group, a biphenyl group, a terphenyl group, a fluorenyl group, a spirobifluorenyl group, and an indenofluorenyl group. More preferred are a phenyl group, a naphthyl group, a biphenyl group, a terphenyl group, a fluorenyl group, and an indenofluorenyl group.

Preferred heteroaromatic groups are a furyl group, a benzofuryl group, an isobenzofuryl group, a dibenzofuranyl group, a thiophene group, a benzothiophenyl group, a dibenzothiophenyl group, a pyrrolyl group, an indolyl group, an isoindolyl group, a carbazolyl group, a benzocarbazolyl group, an indolocarbazolyl group, an indenocarbazolyl group, a pyridyl group, a cinnolyl group, an isocinnolyl group, an acridyl group, a phenanthridyl group, a phenothiazinyl group, a phenoxazyl group, a pyrazolyl group, an indazolyl group, an imidazolyl group, a benzimidazolyl group, a naphthoimidazolyl group, a pyridinimidazolyl group, an oxazolyl group, a benzoxazolyl group, a naphthoxazolyl group, a thiazolyl group, a benzothiazolyl group, a pyrimidyl group, a benzopyrimidyl group, a pyridazinyl group, a quinoxalinyl group, a diazaanthracenyl group, a diazapyrenyl group, a pyrazinyl group, a naphthyridinyl group, an azacarbazolyl group, a benzocarbolinyl group, a phenanthrolinyl group, a triazinyl group, and a 2,6-diphenyl-1,3,5-triazin-4-yl group. More preferred are a dibenzofuranyl group, a dibenzothiophenyl group, a carbazolyl group, a benzocarbazolyl group, an indolocarbazolyl group, an indenocarbazolyl group, a pyridyl group, a cinnolyl group, an isocinnolyl group, an acridyl group, a phenanthridyl group, a phenoxazyl group, a pyrazolyl group, an indazolyl group, a benzimidazolyl group, a pyridinimidazolyl group, a benzoxazolyl group, a benzothiazolyl group, a pyrimidyl group, a benzopyrimidyl group, a pyridazinyl group, a quinoxalinyl group, a pyrazinyl group, a naphthyridinyl group, a triazinyl group, and a 2,6-diphenyl-1,3,5-triazin-4-yl group.

Examples of the aryloxy group that has 5 to 40 carbon atoms and that can be used as each of $R^1$ to $R^{12}$ include a phenoxy group, a methylphenoxy group, a naphtoxy group, and a methoxyphenoxy group. From the viewpoint of the balance between solubility and durability, the number of carbon atoms in these aryloxy groups is preferably 5 or more, and preferably 30 or less, more preferably 25 or less, most preferably 20 or less.

Examples of the arylthio group that has 5 to 40 carbon atoms and that can be used as each of $R^1$ to $R^{12}$ include a phenylthio group, a methylphenylthio group, a naphthylthio group, and a methoxyphenylthio group. From the viewpoint of the balance between solubility and durability, the number of carbon atoms in these arylthio groups is preferably 5 or more, and preferably 30 or less, more preferably 25 or less, most preferably 20 or less.

Examples of the aralkyl group that has 5 to 60 carbon atoms and that can be used as each of $R^1$ to $R^{12}$ include a 1,1-dimethyl-1-phenylmethyl group, a 1,1-di(n-butyl)-1-phenylmethyl group, a 1,1-di(n-hexyl)-1-phenylmethyl group, a 1,1-di(n-octyl)-1-phenylmethyl group, a phenylmethyl group, a phenylethyl group, a 3-phenyl-1-propyl group, a 4-phenyl-1-n-butyl group, a 1-methyl-1-phenylethyl group, a 5-phenyl-1-n-propyl group, a 6-phenyl-1-n-hexyl group, a 6-naphthyl-1-n-hexyl group, a 7-phenyl-1-n-heptyl group, an 8-phenyl-1-n-octyl group, and a 4-phenylcyclohexyl group. From the viewpoint of the balance between solubility and durability, the number of carbon atoms in these aralkyl groups is preferably 5 or more and more preferably 40 or less.

Examples of the heteroaralkyl group that has 5 to 60 carbon atoms and that can be used as each of $R^1$ to $R^{12}$ include a 1,1-dimethyl-1-(2-pyridyl)methyl group, a 1,1-di(n-hexyl)-1-(2-pyridyl)methyl group, a (2-pyridyl)methyl group, a (2-pyridyl)ethyl group, a 3-(2-pyridyl)-1-propyl group, a 4-(2-pyridyl)-1-n-butyl group, a 1-methyl-1-(2-pyridyl)ethyl group, a 5-(2-pyridyl)-1-n-propyl group, a 6-(2-pyridyl)-1-n-hexyl group, a 6-(2-pyrimidyl)-1-n-hexyl group, a 6-(2,6-diphenyl-1,3,5-triazin-4-yl)-1-n-hexyl group, a 7-(2-pyridyl)-1-n-heptyl group, an 8-(2-pyridyl)-1-n-octyl group, and a 4-(2-pyridyl)cyclohexyl group. From the viewpoint of the balance between solubility and durability, the number of carbon atoms in these heteroaralkyl groups is preferably 5 or more, and preferably 50 or less, more preferably 40 or less, most preferably 30 or less.

Examples of the diarylamino group that has 10 to 40 carbon atoms and that can be used as each of $R^1$ to $R^{12}$ include a diphenylamino group, a phenyl(naphthyl)amino group, a di(biphenyl)amino group, and a di(p-terphenyl)amino group. From the viewpoint of the balance between solubility and durability, the number of carbon atoms in these diarylamino groups is preferably 10 or more, and preferably 36 or less, more preferably 30 or less, most preferably 25 or less.

Examples of the arylheteroarylamino group that has 10 to 40 carbon atoms and that can be used as each of $R^1$ to $R^{12}$ include a phenyl(2-pyridyl)amino group and a phenyl(2,6-diphenyl-1,3,5-triazin-4-yl)amino group. From the viewpoint of the balance between solubility and durability, the number of carbon atoms in these arylheteroarylamino groups is preferably 10 or more, and preferably 36 or less, more preferably 30 or less, most preferably 25 or less.

Examples of the diheteroarylamino group that has 10 to 40 carbon atoms and that can be used as each of $R^1$ to $R^{12}$ include a di(2-pyridyl)amino group and a di(2,6-diphenyl-1,3,5-triazin-4-yl)amino group. From the viewpoint of the balance between solubility and durability, the number of carbon atoms in these diheteroarylamino groups is preferably 10 or more, and preferably 36 or less, more preferably 30 or less, most preferably 25 or less.

In order, particularly, not to impair the durability of a light-emitting material in an organic electroluminescent element, $R^1$ to $R^{12}$ are each independently, preferably, a hydrogen atom, F, —CN, a linear, branched, or cyclic alkyl group having 1 to 30 carbon atoms, an aryloxy group having 5 to 40 carbon atoms, an arylthio group having 5 to 40 carbon atoms, a diarylamino group having 10 to 40 carbon atoms, an aralkyl group having 5 to 60 carbon atoms, an aromatic group having 5 to 60 carbon atoms, or a heteroaromatic group having 5 to 60 carbon atoms, particularly preferably, a hydrogen atom, F, —CN, an alkyl group, an aralkyl group, an aromatic group, or a heteroaromatic group, most preferably, a hydrogen atom, F, —CN, an alkyl group, an aromatic group, or a heteroaromatic group.

Two or more adjacent $R^1$ to $R^{12}$ in each of formulae (1) and (2) may be bonded together to form a ring. However, a fused-ring structure need not be formed because a large-sized fused-ring structure can result in excessively high rigidity of the ligand to impair the solubility.

Two or more adjacent $R^1$ to $R^{12}$ in formula (5) may be bonded together to form a ring. In particular, two or more adjacent substituents selected from $R^1$ to $R^{10}$, or $R^{11}$ and $R^{12}$ may be bonded together to form an aliphatic, aromatic, or heteroaromatic, monocyclic or fused ring. However, a fused-ring structure need not be formed because a large-sized fused-ring structure can result in excessively high rigidity of the ligand to impair the solubility.

<R'> each R' is independently selected from a hydrogen atom, D, F, Cl, Br, I, —N(R")$_2$, —NO$_2$, —Si(R")$_3$, —B(OR")$_2$, —C(=O)R", —P(=O) (R")$_2$, —S(=O)$_2$R", —OSO$_2$R", a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R", one —CH$_2$— group or two or more non-adjacent —CH$_2$— groups in these groups are each optionally replaced with —C(—R")=C(—R")—, —CC, —Si(—R")$_2$—, —C(=O)—, —NR"—, —O—, —S—, —CONR"—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R";

Two or more R' may be bonded together to form an aliphatic, aromatic, or heteroaromatic, monocyclic or fused ring. Although R' may be bonded together to form a ring, a fused-ring structure need not be formed because a large-sized fused-ring structure can result in excessively high rigidity of the ligand to impair the solubility.

Examples of the above-described groups that can be used as R' are all as described in the section of $R^1$ to $R^{12}$. That is, for each group that can be used as R', the examples and preferred ranges of the substituents having the same structures as described in the above section of $R^1$ to $R^{12}$ apply.

<R">

Each R" is independently selected from a hydrogen atom, D, F, —CN, an aliphatic hydrocarbon group having 1 to 20 carbon atoms, an aromatic group having 3 to 20 carbon atoms, and a heteroaromatic group having 1 to 20 carbon atoms.

Two or more R" may be bonded together to form an aliphatic, aromatic, or heteroaromatic, monocyclic or fused ring. However, a fused-ring structure need not be formed because a large-sized fused-ring structure formed by bonding R" together to form a ring can result in excessively high rigidity of the ligand to impair the solubility.

PREFERRED ESAMPLES OF R"

Examples of the aliphatic hydrocarbon group that has 1 to 20 carbon atoms and that can be used as R" include linear, branched, or cyclic alkyl groups having 1 to 20 carbon atoms described in the section of $R^1$ to $R^{12}$, and preferred ranges thereof are the same.

Examples of the aromatic group that has 3 to 20 carbon atoms and that can be used as R" include aromatic groups having 3 to 20 carbon atoms described in the section of $R^1$ to $R^{12}$, and preferred ranges thereof are the same.

Examples of the heteroaromatic group that has 1 to 20 carbon atoms and that can be used as R" include heteroaromatic groups having 1 to 20 carbon atoms described in the section of $R^1$ to $R^{12}$, and preferred ranges thereof are the same.

<$R^{13}$ to $R^{22}$>

$R^{13}$ to $R^{22}$ each represent a hydrogen atom or a substituent. When each of $R^{13}$ to $R^{22}$ is a substituent, the type of substituent and its preferred range are the same as those for R' described above. That is, $R^{13}$ to $R^{22}$ are each independently the same as R'.

As with R', two or more adjacent $R^{13}$ to $R^{22}$ may be bonded together to form a ring. In this case, it is clear that two or more adjacent substituents that can be bonded together to form a ring are two or more adjacent substituents selected from $R^{13}$ to $R^{17}$ or two or more adjacent substituents selected from $R^{18}$ to $R^{22}$. A fused-ring structure need not be formed because a large-sized fused-ring structure can result in excessively high rigidity of the ligand to impair the solubility.

The three ligands in each of formula (1) and (2) may be the same or different.

Preferred Embodiment of $Ar^1$, $Ar^2$, $R^1$ to $R^4$, and $R^{13}$ to $R^{22}$ In a more preferred embodiment for the purpose of increasing the solubility without adversely affecting the light emission efficiency or the half-width, at least one linear, branched, or cyclic alkyl group having 4 to 30 carbon atoms or aralkyl group having 5 to 30 carbon atoms is present in the atomic groups of $Ar^1$ and $Ar^2$ in formula (1) or $R^1$ to $R^4$ in formulae (1), (2), and (5). Particularly preferably, at least one or more of these groups are contained in at least one or more of $Ar^1$ and $Ar^2$. The presence of these groups can increase the solubility in a solvent. The presence of these groups in $R^1$ to $R^4$ can increase the solubility in a solvent while preventing a decrease in quantum yield due to the fact that the fluorene side is oxidized to impede the entry of electrons.

Moreover, in order to improve the solubility and suppress the lengthening of the maximum emission wavelength, preferably, at least one or more of $R^{13}$, $R^{17}$, $R^{18}$, and $R^{22}$ in formula (5) are each a substituent that is not a hydrogen atom.

In a more preferred embodiment for the purposes of increasing the solubility and suppressing the influence of the introduction of the substituent on the maximum emission wavelength without adversely affecting the light emission efficiency or the half-width, at least one or more of $R^{13}$, $R^{17}$, $R^{18}$, and $R^{22}$ in each of formulae (2) and (5) are each an alkyl group having 1 to 4 or an optionally substituted aromatic ring group. In this case, the optionally substituted aromatic ring group refers to an aromatic group that is optionally substituted with R" and that has 5 to 60 carbon atoms from the definitions of $R^{13}$, $R^{17}$, $R^{18}$, and $R^{22}$. The introduction of these groups, as needed, can improve the solubility and twists the bond between the quinoline ring and the aromatic ring having the substituents. Thus, the conjugation of fluorene and quinoline does not extend beyond the aromatic groups attached at the 4- and 6-positions of quinoline. This results in a short conjugation length to prevent the lengthening of the wavelength more than necessary.

Particularly preferably, at least one or more of $R^{18}$ and $R^{22}$ in formula (5) are each an alkyl group having 1 to 4 carbon atoms or an optionally substituted aromatic group.

A structure in which at least one of the substituents $R^1$ to $R^4$ and $R^{13}$ to $R^{22}$ in formulae (2) and (5) is an alkyl group having 4 to 30 carbon atoms or an aralkyl group having 5 to 30 carbon atoms is preferred because the solubility in a solvent can seemingly be improved without any electronic effect on fluorene.

In a structure in which at least one or more of the substituents $R^{13}$, $R^{17}$, $R^{18}$, and $R^{22}$ in formulae (2) and (5) are each a substituent such as an alkyl group, the steric hindrance between the benzene ring attached to the quinoline ring and the quinoline ring results in the twist of the bond to break the conjugation, suppressing the lengthening of the wavelength more than necessary. This can increase the quantum yield (it is known that in the case of a long wavelength, the quantum yield is low according to the energy gap law, and a shorter wavelength results in a higher quantum yield). Particularly preferably, each of the substituents is an alkyl group having 1 to 4 carbon atoms or an optionally substituted aromatic ring group.

Each of the substituents $R^{18}$ and $R^{22}$ in formula (2), (5), or (6) is preferably an alkyl group having 1 to 4 carbon atoms. In the case where each of the substituents $R^{18}$ and $R^{22}$ is an alkyl group having 1 to 4, a sufficient twist can be formed between the quinoline ring and the benzene ring attached to the quinoline ring, so that the lengthening of the wavelength can be suppressed more sufficiently.

In the case where at least one or more of the substituents $R^{14}$, $R^{15}$, $R^{16}$, $R^{19}$, $R^{20}$, and $R^{21}$ in each of formulae (2) and (5) are each an alkyl group, an optionally substituted aromatic ring group, or an aralkyl group and where at least one or more of $R^{13}$, $R^{17}$, $R^{18}$, and $R^{22}$ each have a substituent such as an alkyl group, a twisted moiety, i.e., the benzene ring attached to the quinoline ring in a twisted manner has a structure that increases the solubility in a solvent. This can prevent the lengthening of the wavelength more than necessary, thereby increasing the PL yield and the solubility in a solvent, which is preferred. An optionally substituted aromatic ring group is particularly preferred. The substituent is more preferably an aralkyl group. This structure is obtained in the case where at least one or more of $R^{14}$, $R^{15}$, and $R^{16}$ are each an alkyl group, an optionally substituted aromatic ring group, or an aralkyl group and where at least one or more of $R^{13}$ and $R^{17}$ each have a substituent such as an alkyl group. Alternatively, this structure is also obtained in the case where at least one or more of $R^{19}$, $R^{20}$, and $R^{21}$ are each an alkyl group, an optionally substituted aromatic ring group, or an aralkyl group and where at least one or more of $R^{18}$ and $R^{22}$ each have a substituent such as an alkyl group.

The substituent, such as an alkyl group, on each of the substituents $R^{13}$, $R^{17}$, $R^{18}$, and $R^{22}$ in each of formulae (2) and (5) may be further substituted with an aromatic ring group or an aralkyl group. In this way, the substituent that produces twisting and the structure that increases the solubility can be provided within the same substituent.

SPECIFIC EXAMPLES

Specific examples of preferred iridium complex compounds of the present invention other than iridium complex compounds given in Examples described later will be illustrated below, regarding the case where m=3 in formulae (1), (2), and (5). The iridium complex compounds of the present invention are not limited to any of these exemplified compounds below.

[Chem. 9]

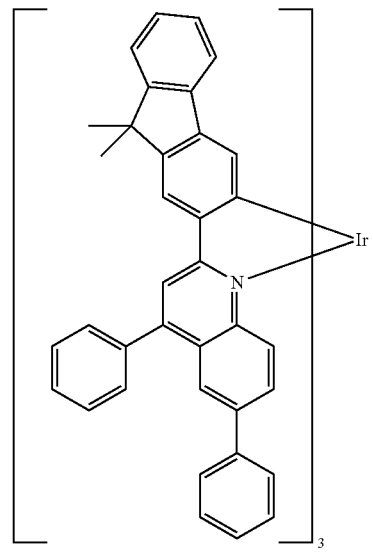

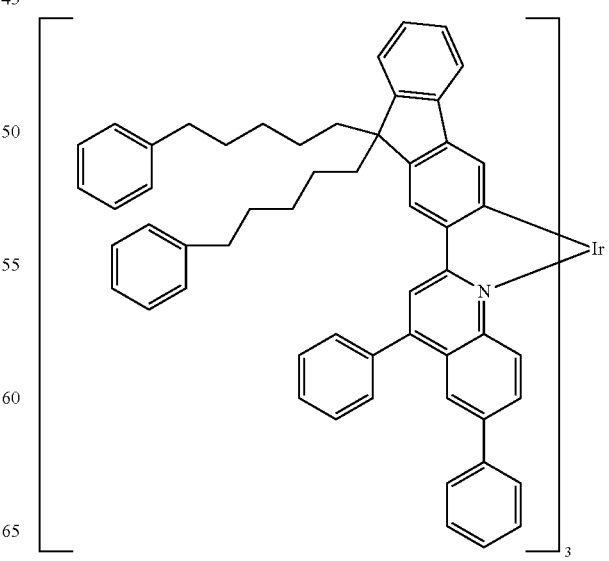

21
-continued
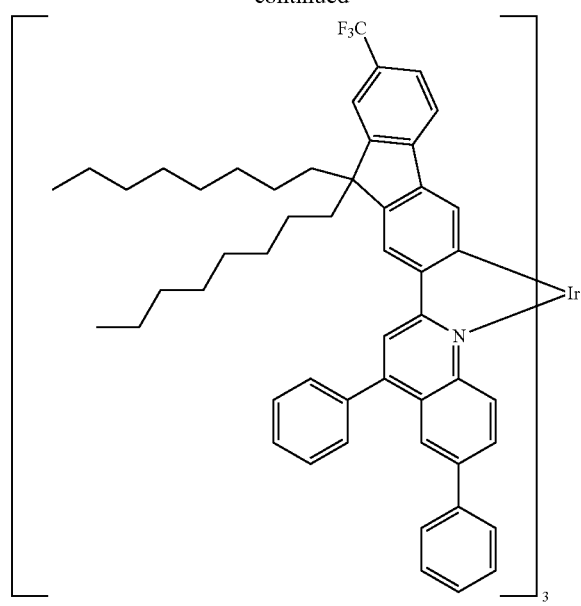
22
-continued
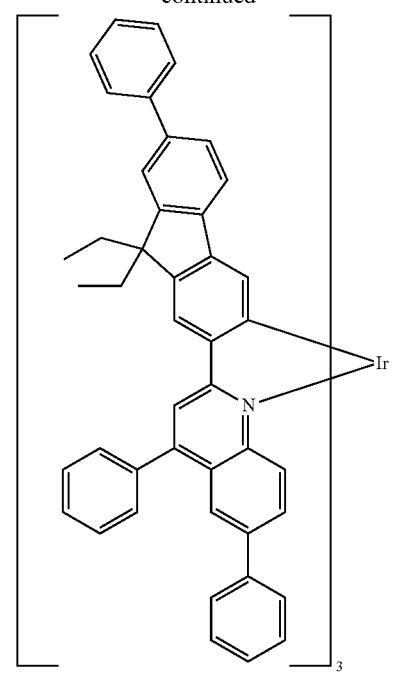
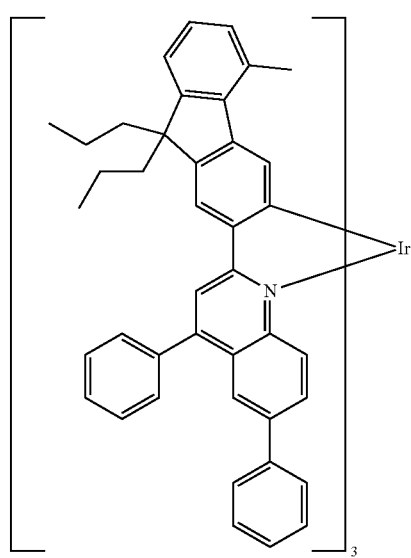
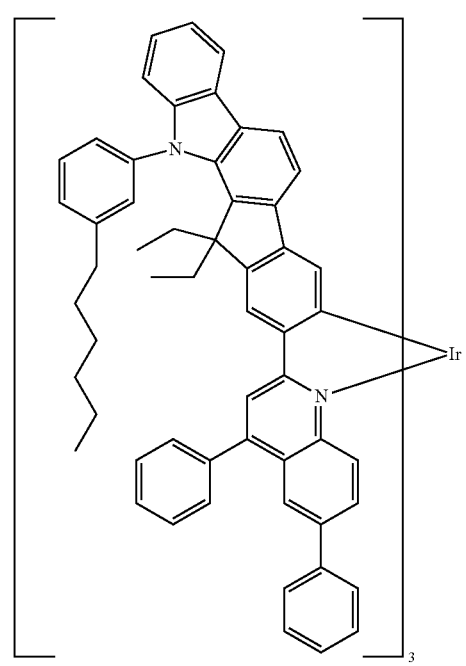

23
-continued
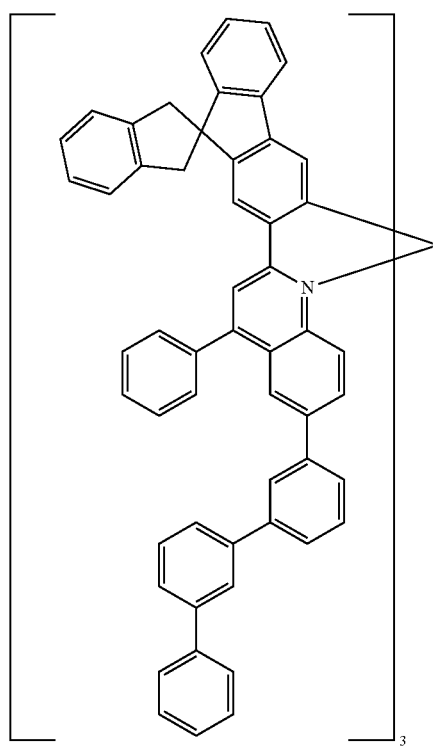
24
-continued
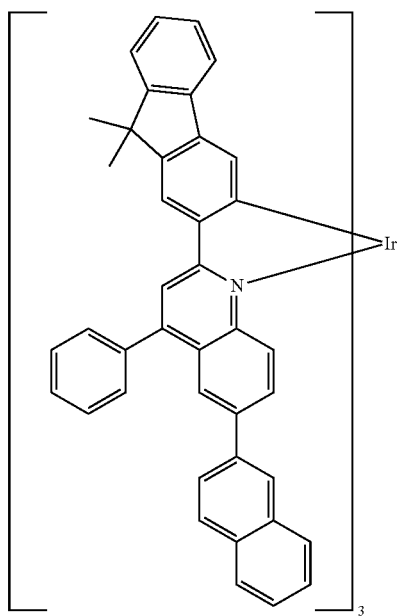
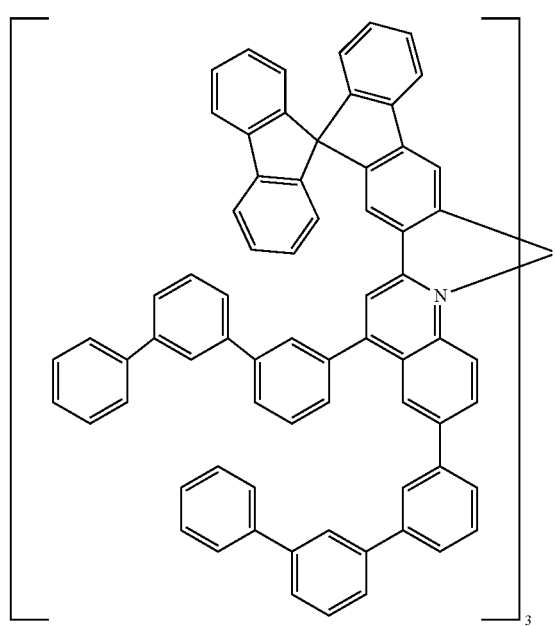
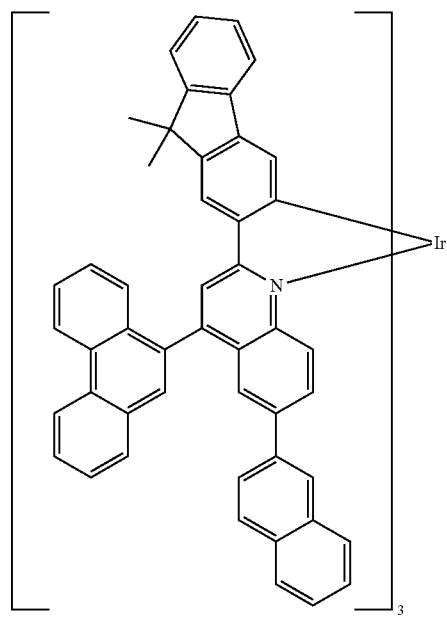

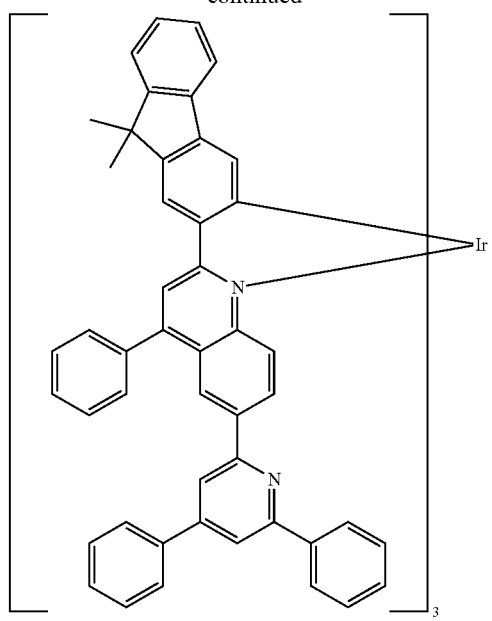
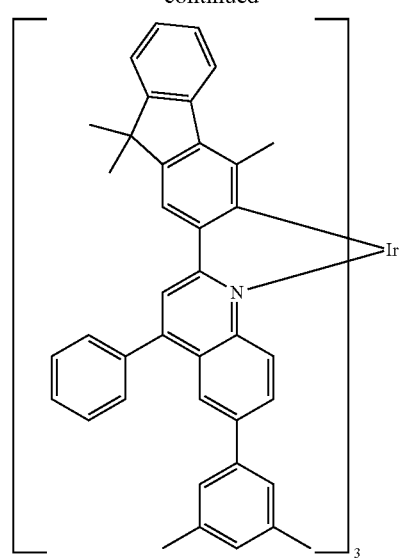
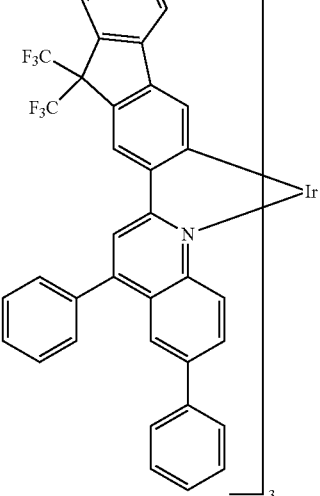
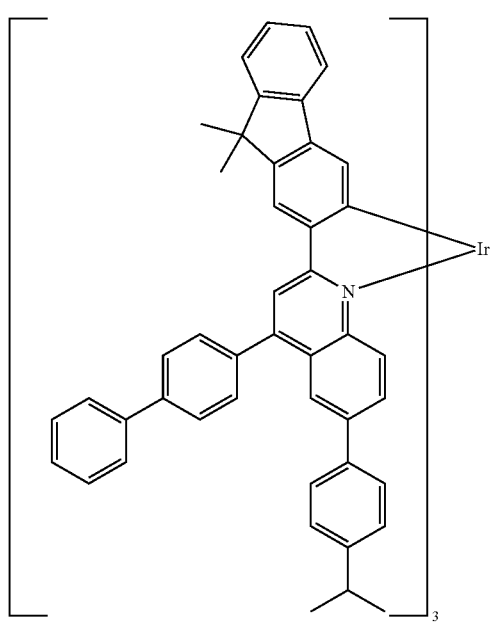

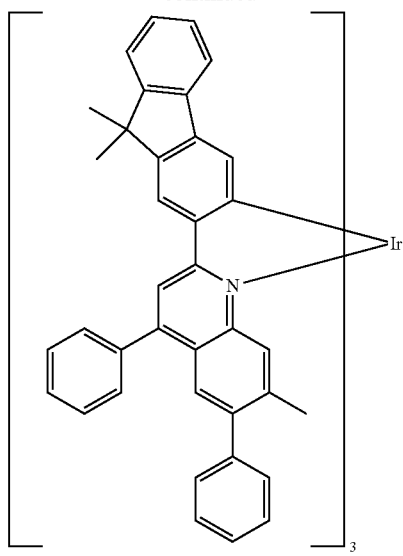
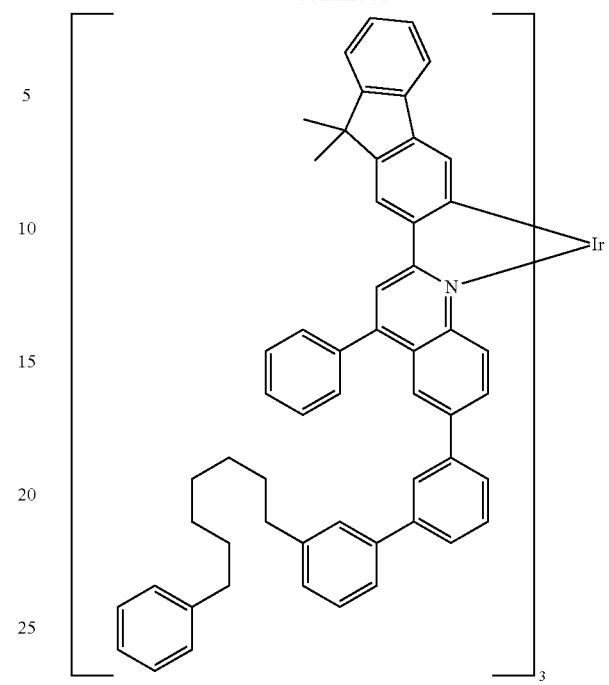
Specific examples of more preferred embodiments will be illustrated below.
[Chem. 10]
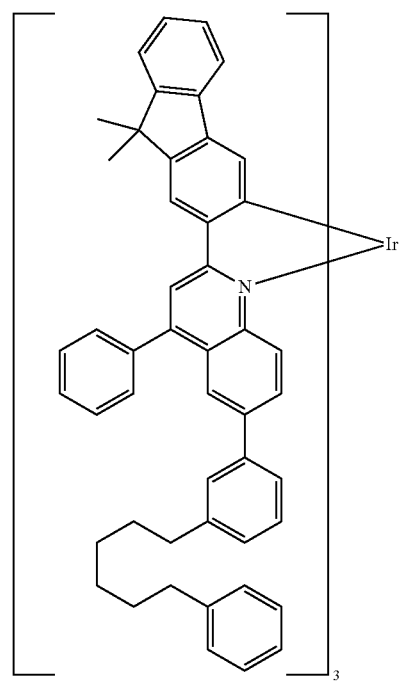
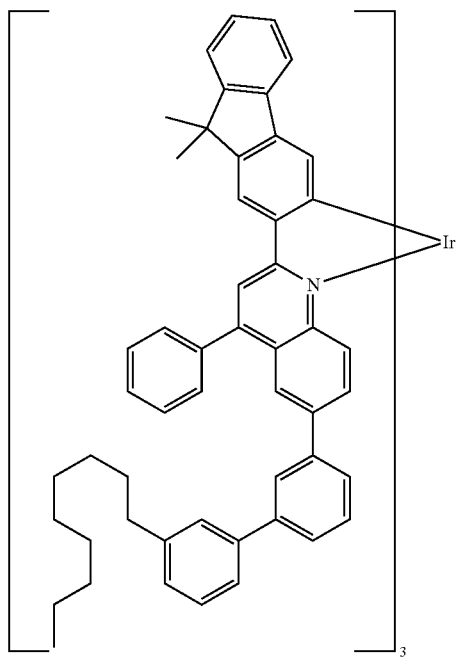

29
-continued
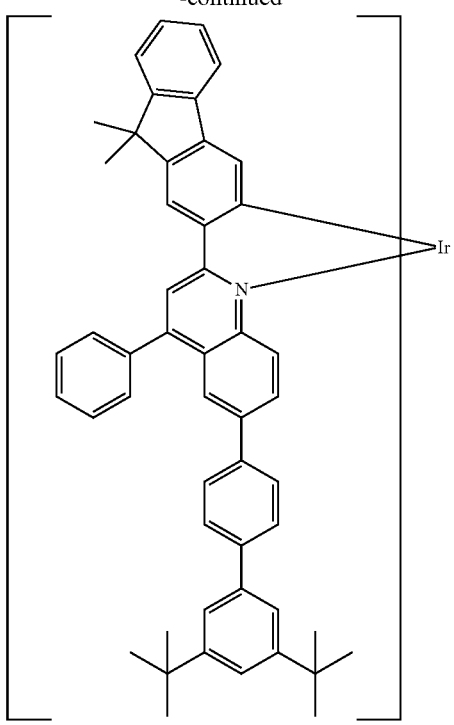
30
-continued
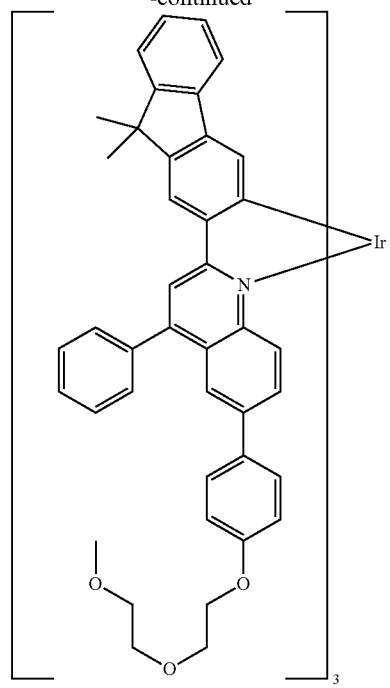
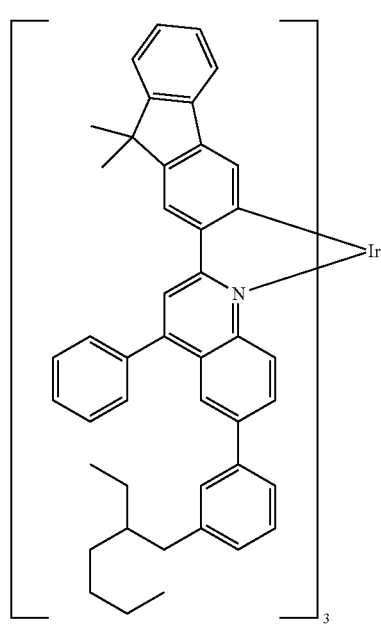
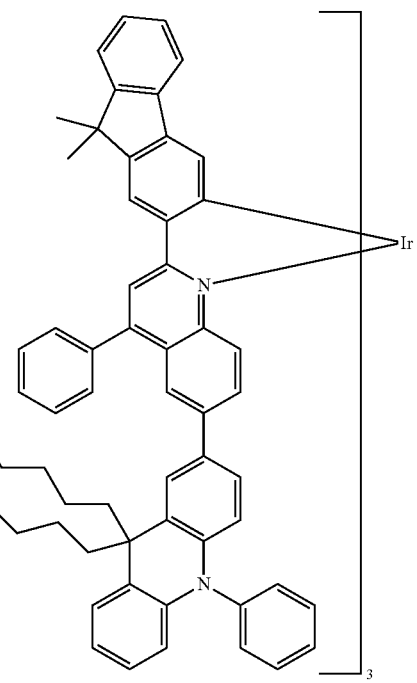

-continued
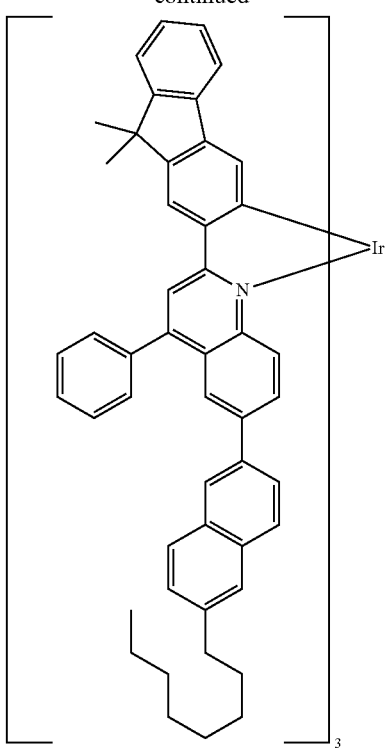
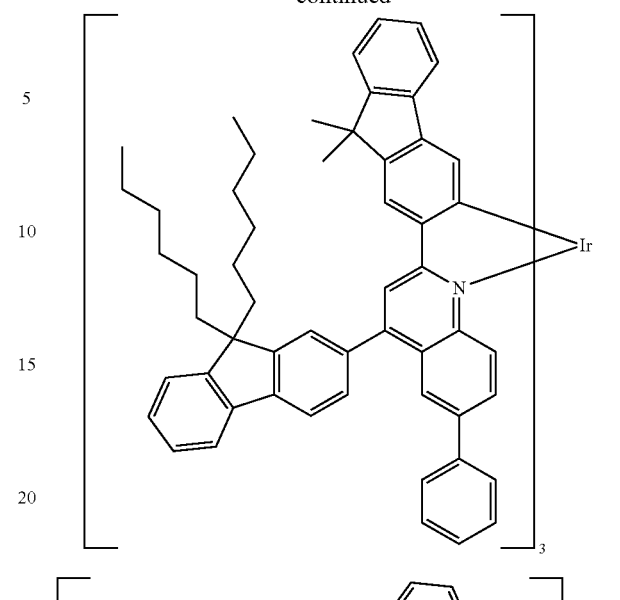
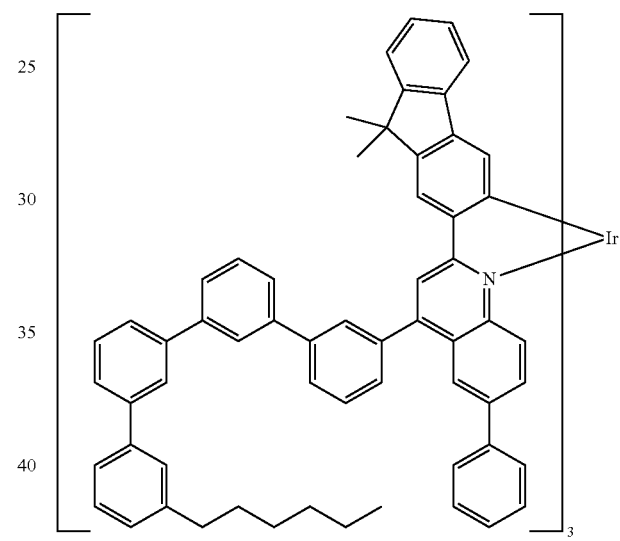
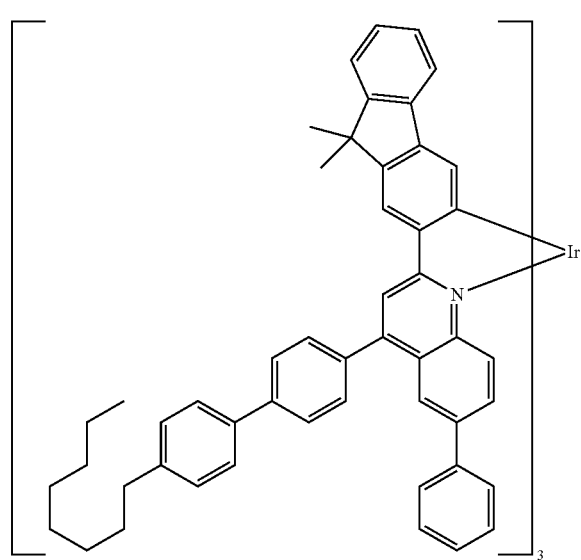
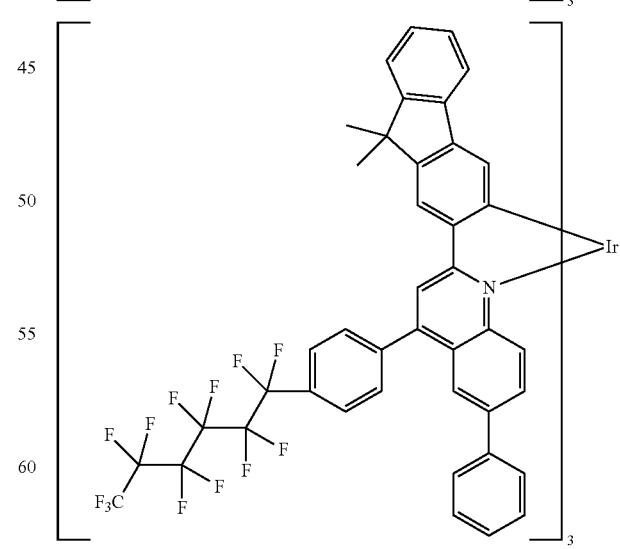

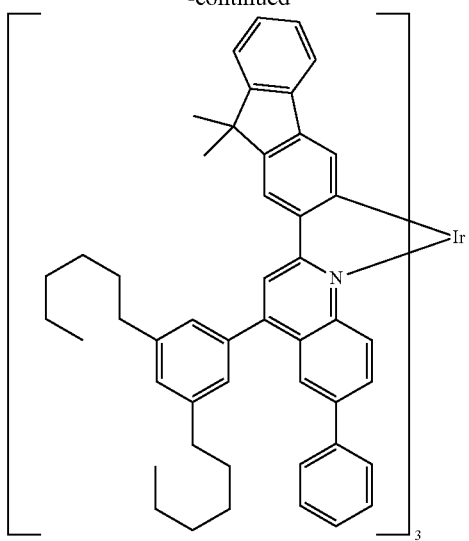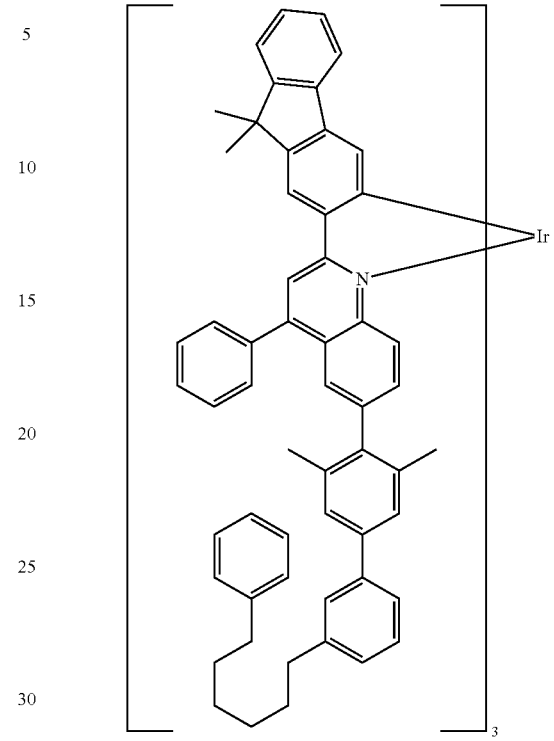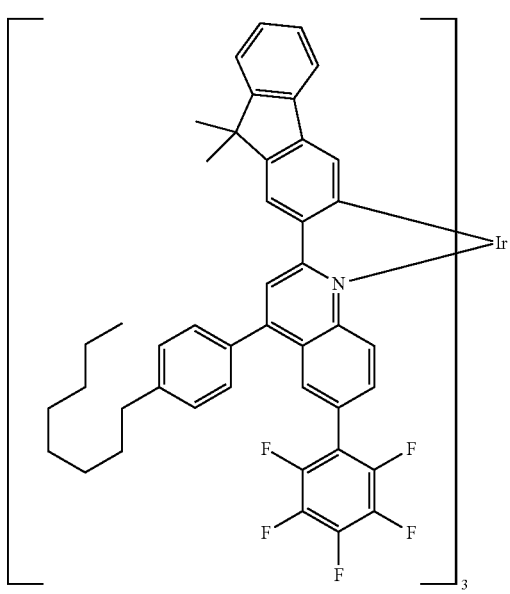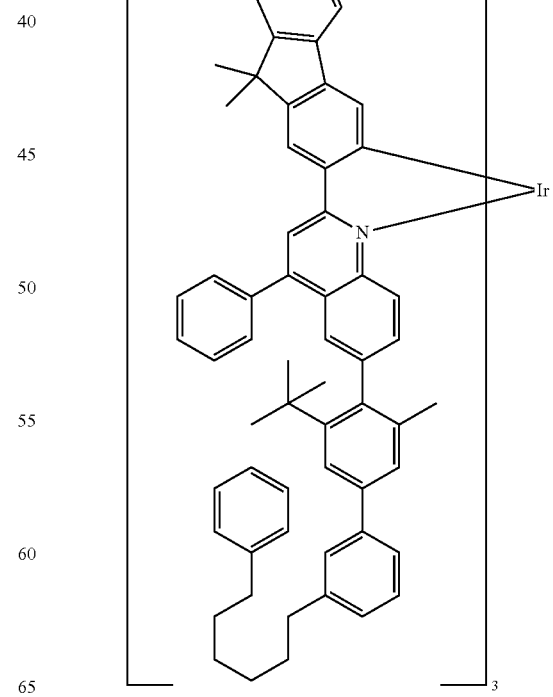
Specific examples of more preferred embodiments will be illustrated below.

35
-continued
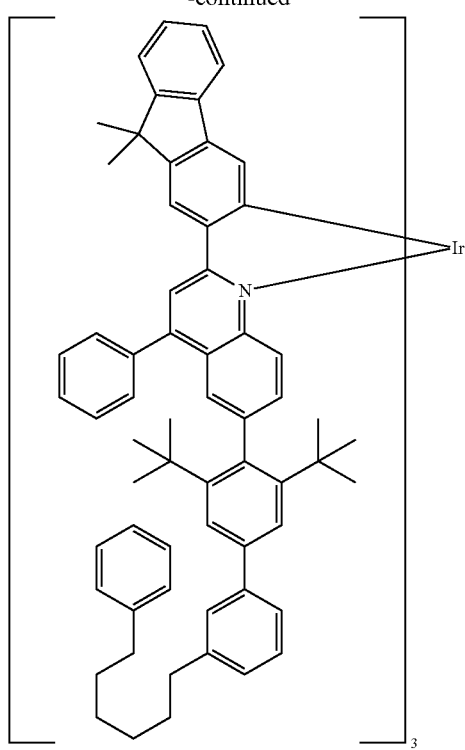
36
-continued
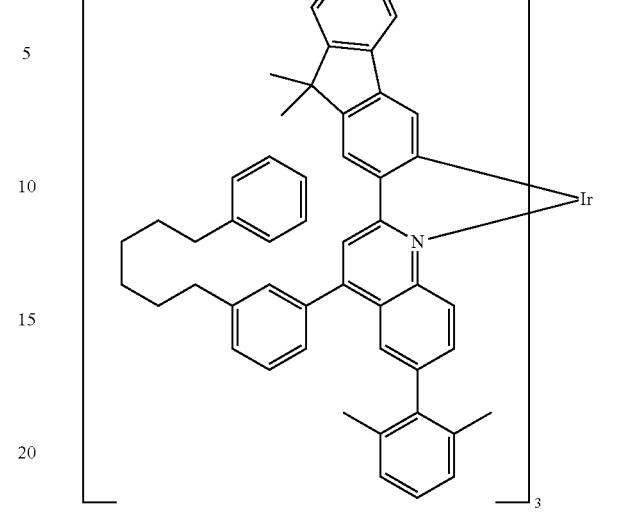
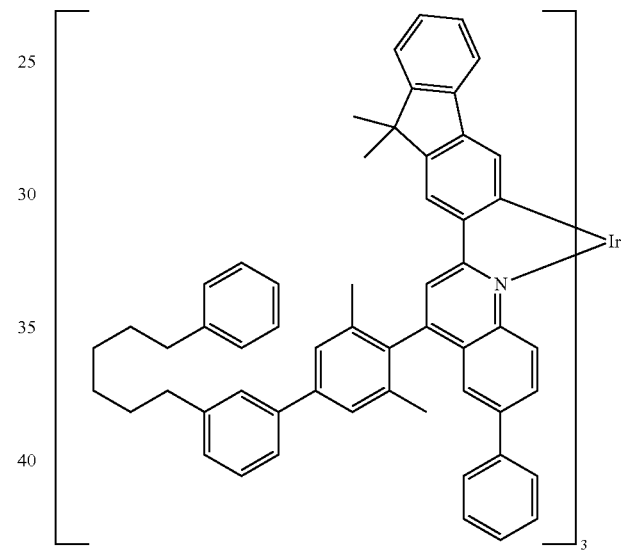
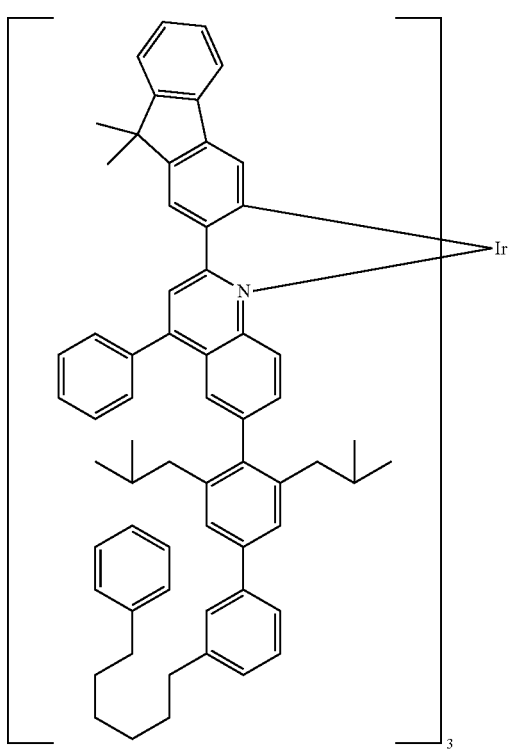
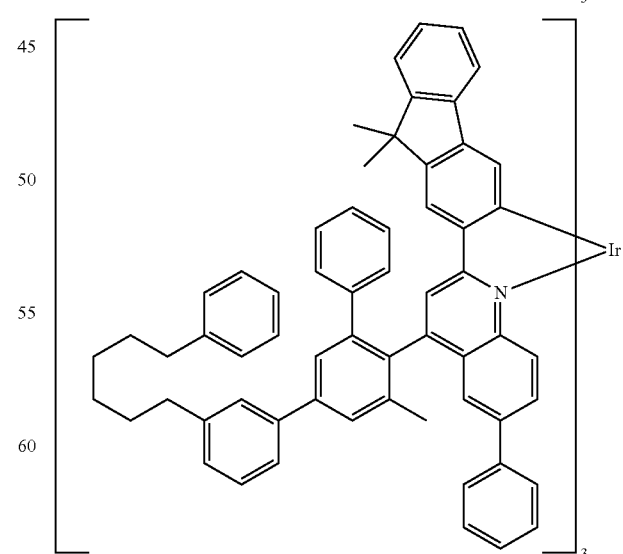

37
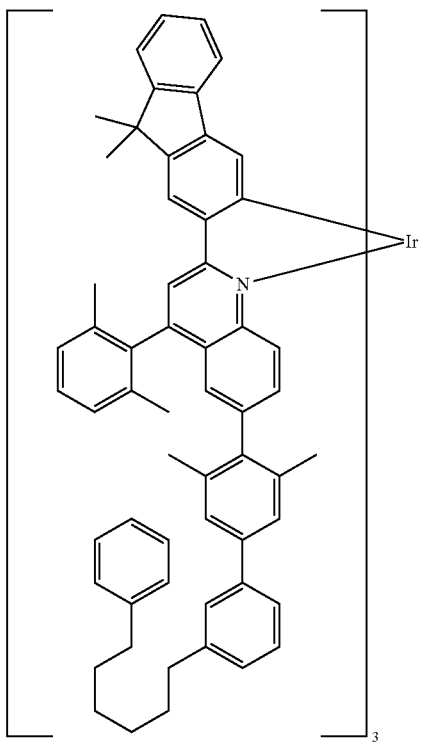
38
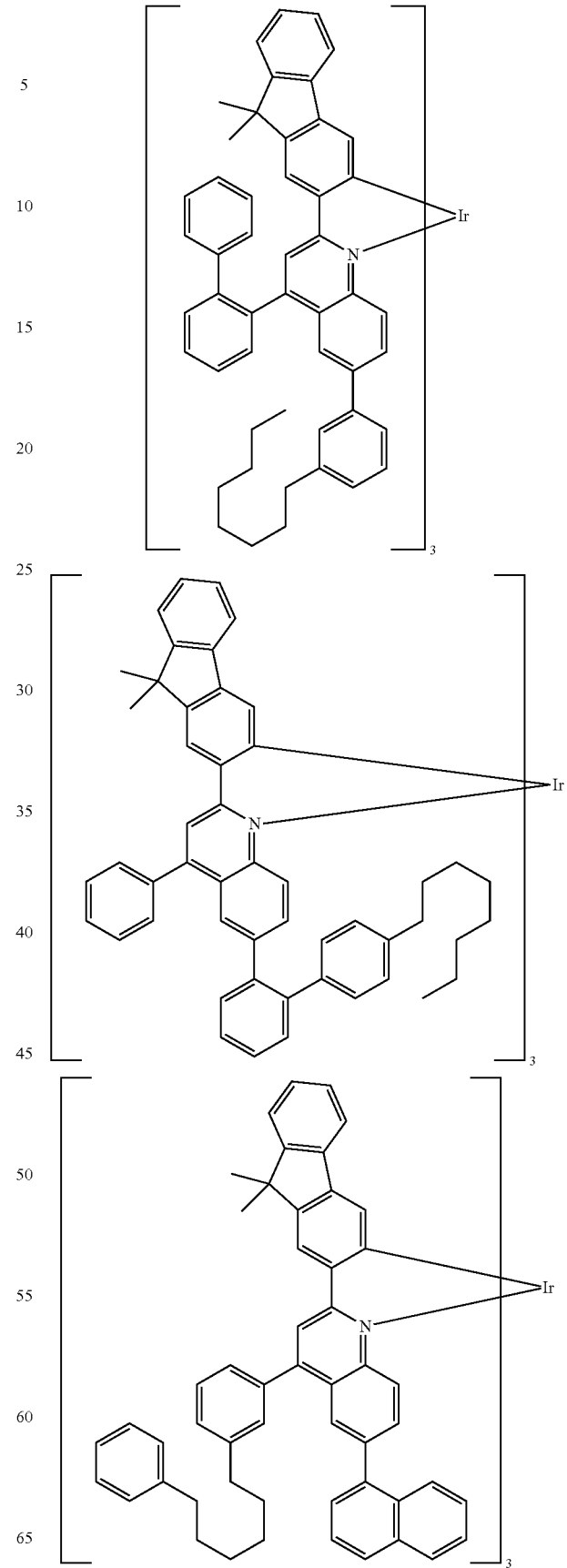

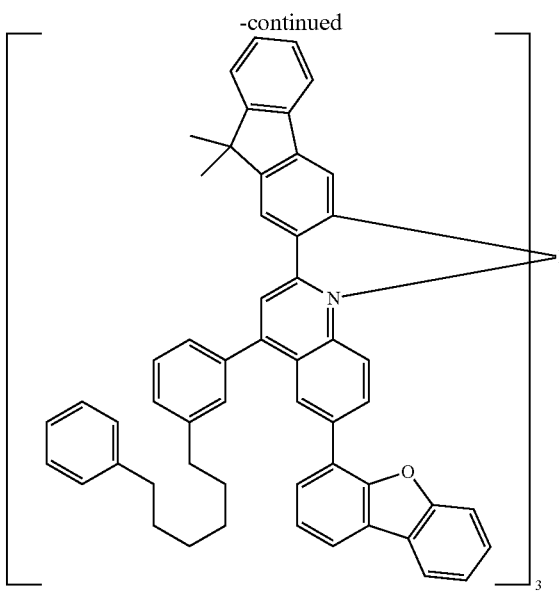

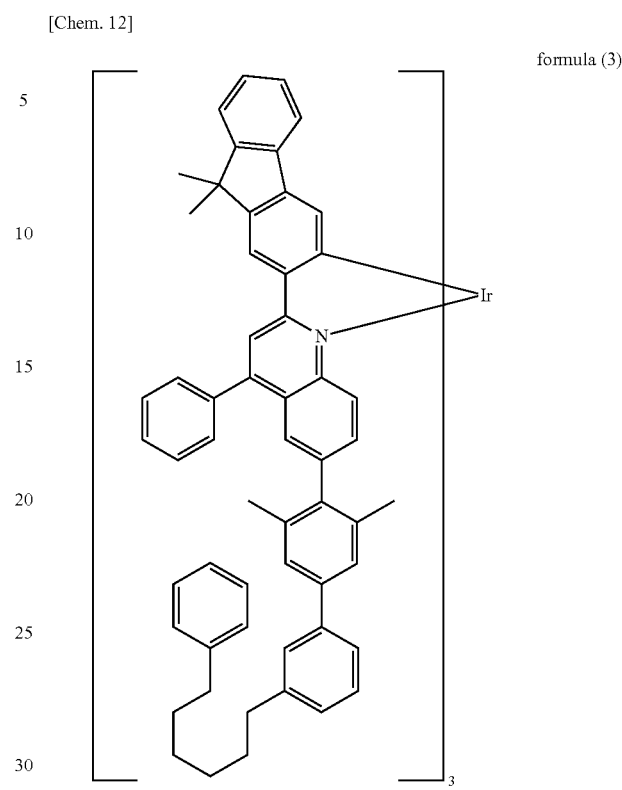

As the iridium complex compound of the present invention, a compound represented by formula (4) below is preferred.

[Chem. 13]

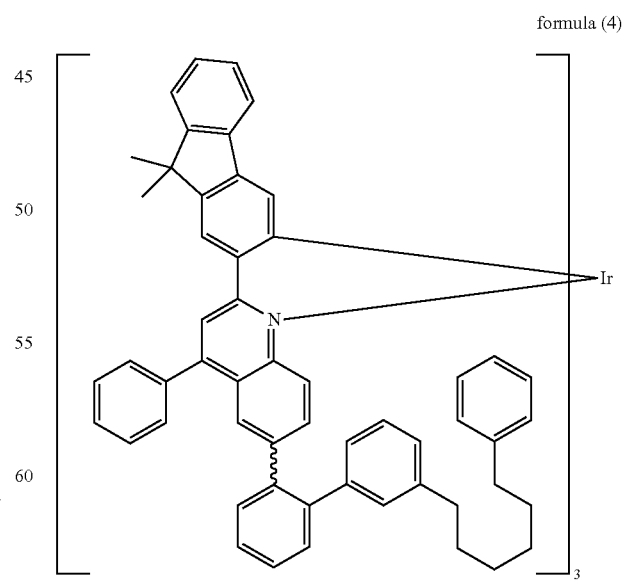

formula (4)

The wiggly line in formula (4) is used to indicate a mixture of rotamers.

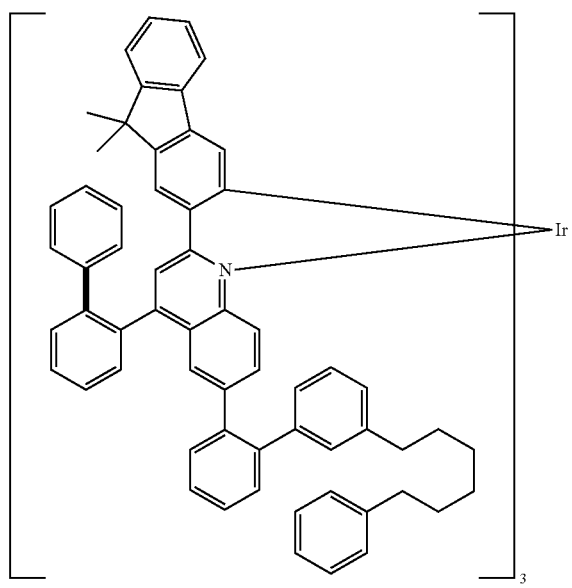

Among the foregoing compounds illustrated as specific examples, the compounds in which at least one of the groups corresponding to $R^{13}$, $R^{17}$, $R^{18}$, and $R^{22}$ is a substituent other than a hydrogen atom are particularly preferred from the viewpoints of improving the quantum yield and suppressing the lengthening of the wavelength.

As the iridium complex compound of the present invention, a compound represented by formula (3) below is particularly preferred.

[Iridium Complex Compounds Represented by Formulae (5) and (6)]

A preferred embodiment of the iridium complex compound represented by formula (5) is a compound represented by formula (6) below, where X is represented by formula (6a) below.

[Chem. 14]

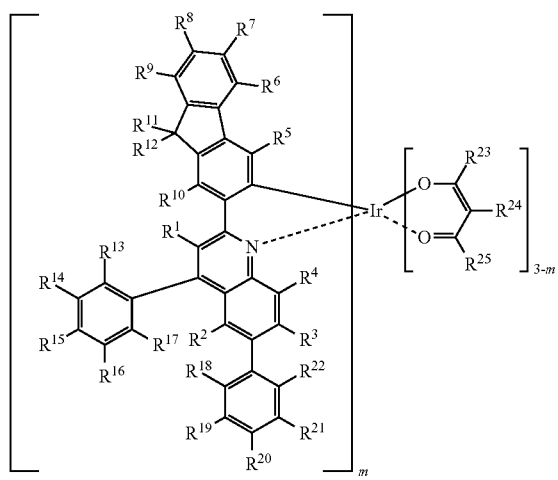

formula (6)

[Chem. 15]

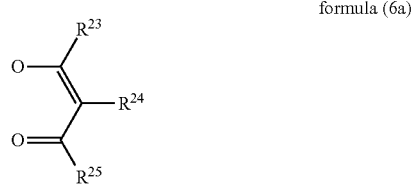

formula (6a)

where in formula (6), $R^2$ to $R^{22}$, and m are defined the same as in formula (5);
where in formula (6), (6a), $R^{23}$ and $R^{25}$ are each independently selected from —N(R')$_2$, —COOR', —C(=O)R', —C(=O)NR', —P(=O) (R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

$R^{24}$ is selected from a hydrogen atom, D, —N(R')$_2$, —COOR', —C(=O)R', —C(=O)NR', —P(=O) (R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

two or more adjacent $R^{23}$ to $R^{25}$ are optionally bonded together to form an aliphatic, aromatic, or heteroaromatic, monocyclic or fused ring;

the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(—R')=C(—R')—, —C≡C—, —Si(—R')$_2$, —C(=O)—, —NR'—, —O—, —S—, —CONR'—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R'; and when $R^{23}$ to $R^{25}$ each have R', R' is the same as R' in formula (5).

In the present invention, more preferably, only one of the three ligands is the ligand represented by formula (6a), i.e., m=2 in formula (6), because the half-width is narrowed.

<$R^{23}$ and $R^{25}$>

Similar to $R^{23}$ to $R^{25}$ in formula (5), when $R^{23}$ to $R^{25}$ each have R", R" is the same as R" in formula (5).

Specific examples, preferred ranges, and preferred embodiments of the above-described group in $R^{23}$ and $R^{25}$ are the same as the specific examples, the preferred ranges, and the preferred embodiments as described in the above section of $R^1$ to $R^{12}$ in formula (5).

Preferably, $R^{23}$ and $R^{25}$ are each independently the alkyl group, the aromatic group, the heteroaromatic group, the aralkyl group, or the heteroaralkyl group, more preferably the alkyl group or the aralkyl group, in view of durability.

<$R^{24}$>

Specific examples, preferred ranges, and preferred embodiments of the above-described group in $R^{24}$ are the same as the specific examples, the preferred ranges, and the preferred embodiments as described in the above section of $R^1$ to $R^{12}$ in formula (5).

Preferably, $R^{24}$ is independently the hydrogen atom, the alkyl group, the aromatic group, the heteroaromatic group, the aralkyl group, or the heteroaralkyl group, more preferably the hydrogen atom or the aralkyl group, in view of durability.

Two or more adjacent $R^{23}$ to $R^{25}$ in formula (6) may be bonded together to form an aliphatic, aromatic, or heteroaromatic, monocyclic or fused ring.

In the case where $R^{23}$ to $R^{25}$ are bonded together to form a fused ring, examples of the fused ring include aliphatic rings and their fused rings, such as hexahydro-1,8(2H,5H)-naphthalenedione and 1,3-cyclodecanedione, and fused rings of aromatics and aliphatics, such as 2-acetyl-3,4-dihydro-1(2H)-naphthalenone.

Aliphatic fused rings are preferred in view of durability.

In each of formulae (5) and (6), m is an integer of 1 to 3, preferably 2 or 3, in view of durability.

In formula (5) or (6), two or more adjacent substituents selected from $R^1$ to $R^{10}$, two or more adjacent substituents selected from $R^{11}$ and $R^{12}$, two or more adjacent substituents selected from $R^{13}$ to $R^{17}$, or two or more adjacent substituents selected from $R^{18}$ to $R^{22}$ may be bonded together to form an aliphatic, aromatic, or heteroaromatic, monocyclic or fused ring. However, a fused-ring structure need not be formed because a large-sized fused-ring structure can result in excessively high rigidity of the ligand to impair the solubility.

In each of formulae (5) and (6), when m is 2 or more, the ligands having $R^{1-12}$ and $R^{13-22}$ may be the same or different.

In each of formulae (5) and (6), when m is 1, two ligands X in formula (5) and two ligands (—OC($R^{23}$)═C($R^{24}$)C($R^{25}$)═O—) in formula (6) may be the same or different.

In formula (5), when m=3, the iridium complex compound represented by formula (5) is substantially the same as the iridium complex compound represented by formula (2).

Specific Examples of Iridium Complex Compound Represented by Formulae (5) and (6)

Specific examples of preferred iridium complex compounds represented by formulae (5) and (6) according to the present invention other than iridium complex compounds given in Examples described later will be illustrated below. The iridium complex compounds of the present invention are not limited to any of these exemplified compounds below.

[Chem. 16]

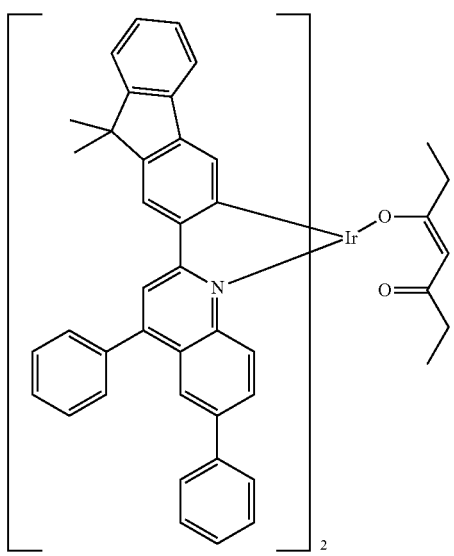

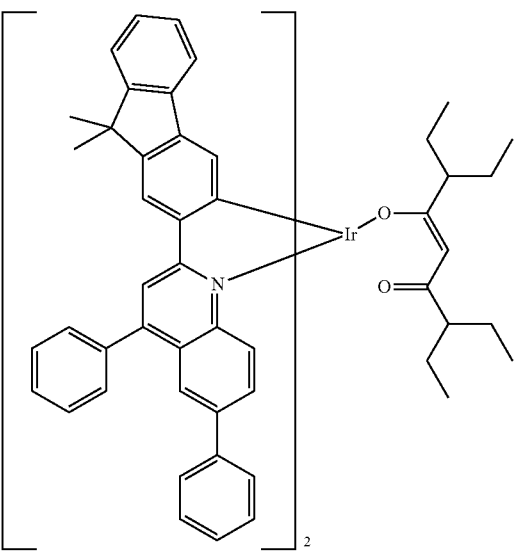

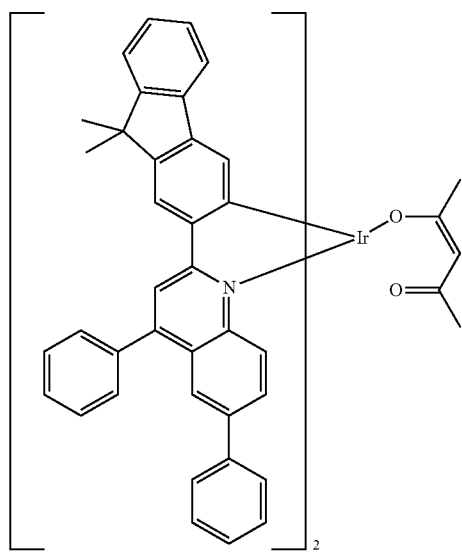

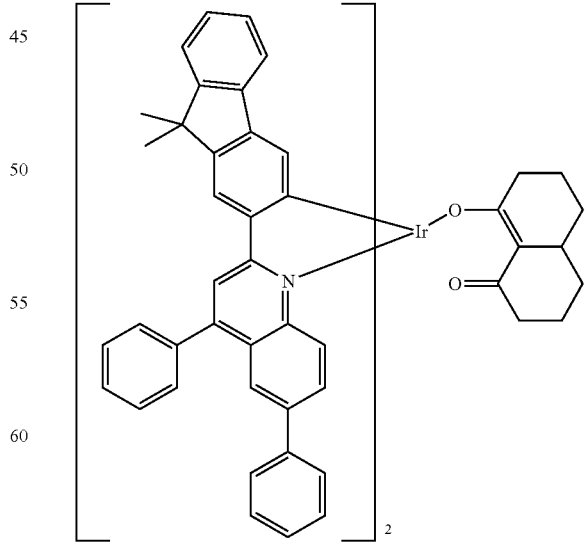

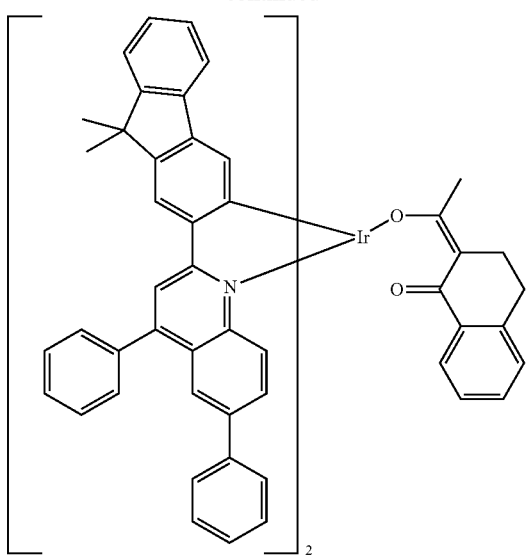
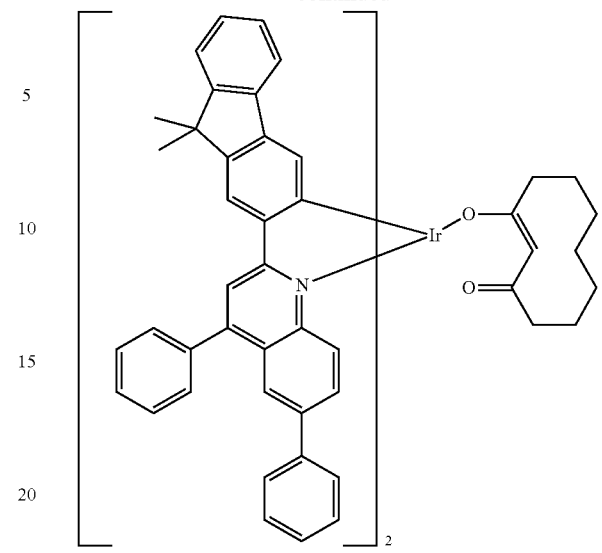
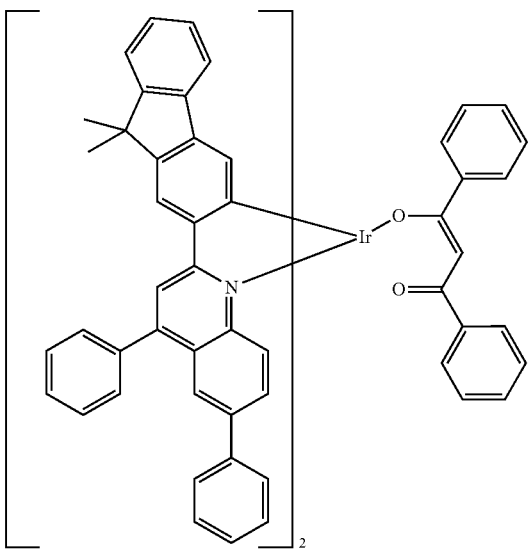
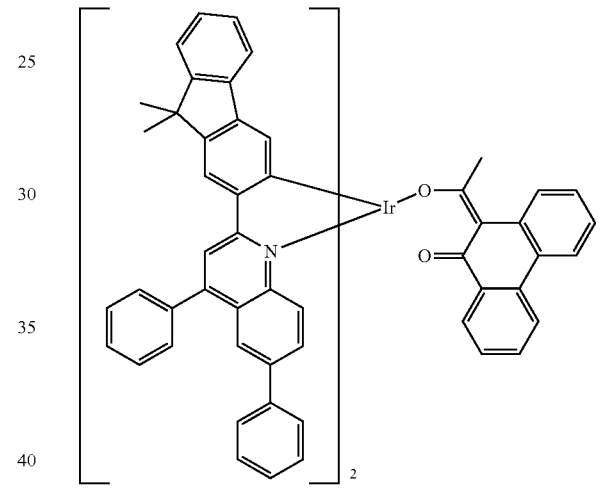
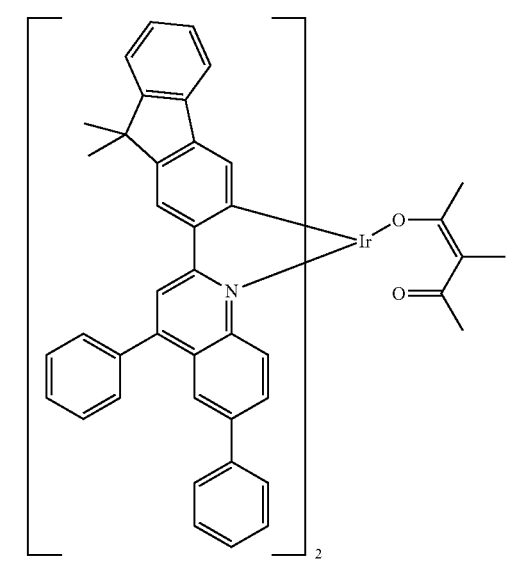
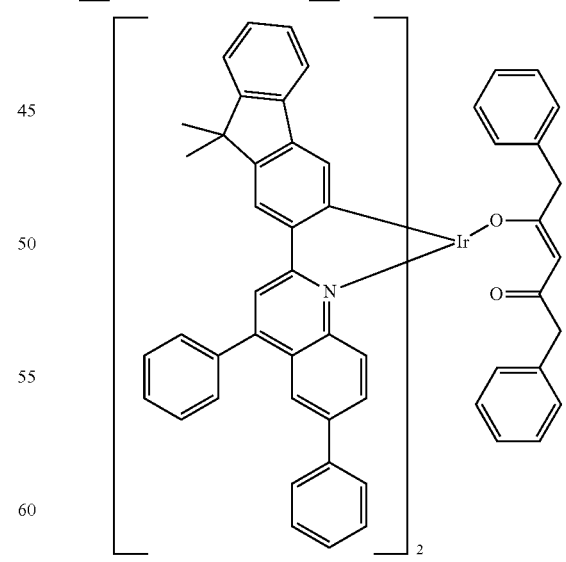

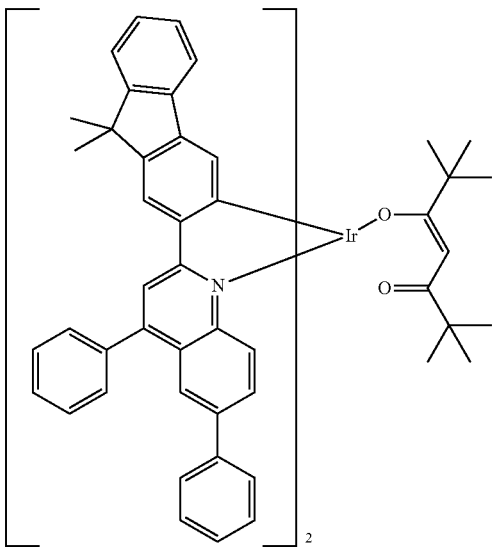
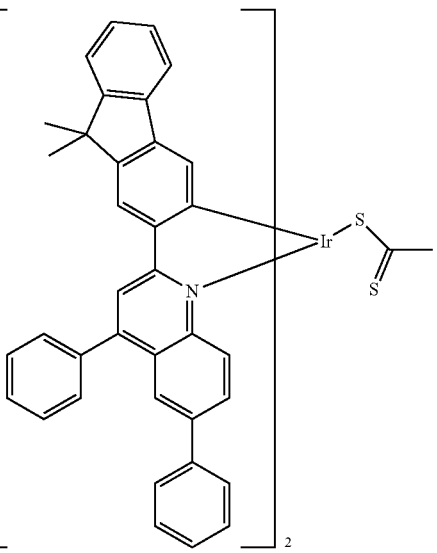
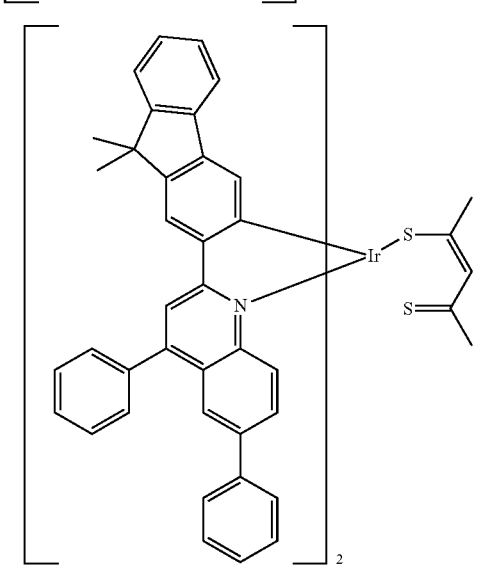

<Maximum Emission Wavelength>

The iridium complex compound of the present invention can have an appropriately lengthened emission wavelength. As an indicator of the length of an emission wavelength, the maximum emission wavelength measured by the following procedure is preferably 615 nm or more, more preferably 620 nm or more, and preferably 650 nm or less, more preferably 640 nm or less, even more preferably 635 nm or less. When the maximum emission wavelength is in this range, a preferred color of a red-light-emitting material suitable for an organic electroluminescent element tends to be exhibited.

(Method of Measuring Maximum Emission Wavelength)

At normal temperature, the phosphorescence spectrum of a solution obtained by dissolving the iridium complex compound in 2-methyltetrahydrofuran at a concentration $1 \times 10^{-4}$ mol/L or less is measured with a spectrophotometer (C9920-02 organic EL quantum yield spectrometer manufactured by Hamamatsu Photonics K.K.). The wavelength at a maximum intensity in the measured phosphorescence spectrum is used a maximum emission wavelength.

<Method of Synthesizing Iridium Complex Compound>
<Method of Synthesizing Ligand>

The ligands of the iridium complex compound of the present invention can be synthesized, for example, by a combination of known methods. The fluorene ring can be readily introduced, for example, by using, as a raw material, a compound having bromine, a —B(OH)$_2$ group, an acetyl group, or a carboxy group at the 2-position or the 3-position of a fluorene ring. The fluorene-quinoline ligand can be synthesized by further subjecting these raw materials to a known reaction such as Suzuki-Miyaura coupling reaction with halogenated quinoline or Friedlaender cyclization reaction with 2-formyl or acyl aniline or with acyl-amino pyridine in ortho position to each other (Chem. Rev. 2009, 109, 2652 or Organic Reactions, 28(2), 37-201).

<Method of Synthesizing Iridium Complex Compound>

The iridium complex compound of the present invention can be synthesized, for example, by a combination of known methods. Details will be described below.

Examples of the method of synthesizing the iridium complex compound includes, but are not limited to, a method by which the target compound is obtained through a chloro-bridged iridium binuclear complex as expressed by reaction formula [A] below (M. G. Colombo, T. C. Brunold, T. Riedener, H. U. Gudel, Inorg. Chem., 1994, 33, 545-550), where a phenylpyridine ligand is used for ease of understanding, and a method by which the target compound is obtained after a binuclear complex is converted into a mononuclear complex by exchanging a chloro bridge for acetylacetonate as expressed by reaction formula [B] below (S. Lamansky, P. Djurovich, D. Murphy, F. Abdel-Razzaq, R. Kwong, I. Tsyba, M. Borz, B. Mui, R. Bau, M. Thompson, Inorg. Chem., 2001, 40, 1704-1711).

For example, conditions for the typical reaction expressed by reaction formula [A] below are as follows. In the first stage, a chloro-bridged iridium binuclear complex is synthesized through a reaction of 2 equivalents of a ligand and 1 equivalent of iridium chloride n-hydrate. Typically, a mixed solvent of 2-ethoxyethanol and water is used, but the reaction may be performed without a solvent or with another solvent. The reaction can be promoted by using the ligand in excess amount or using an additive such as a base. Instead of chlorine, other crosslinkable anionic ligands such as bromine can be used.

The reaction temperature is not particularly limited, and typically, it is preferably 0° C. or more, more preferably 50° C. or more, and preferably 250° C. or less, more preferably 150° C. or less. When the reaction temperature is in this range, the desired reaction alone tends to proceed with no by-products or decomposition reaction, thus achieving high selectivity.

[Chem. 17]

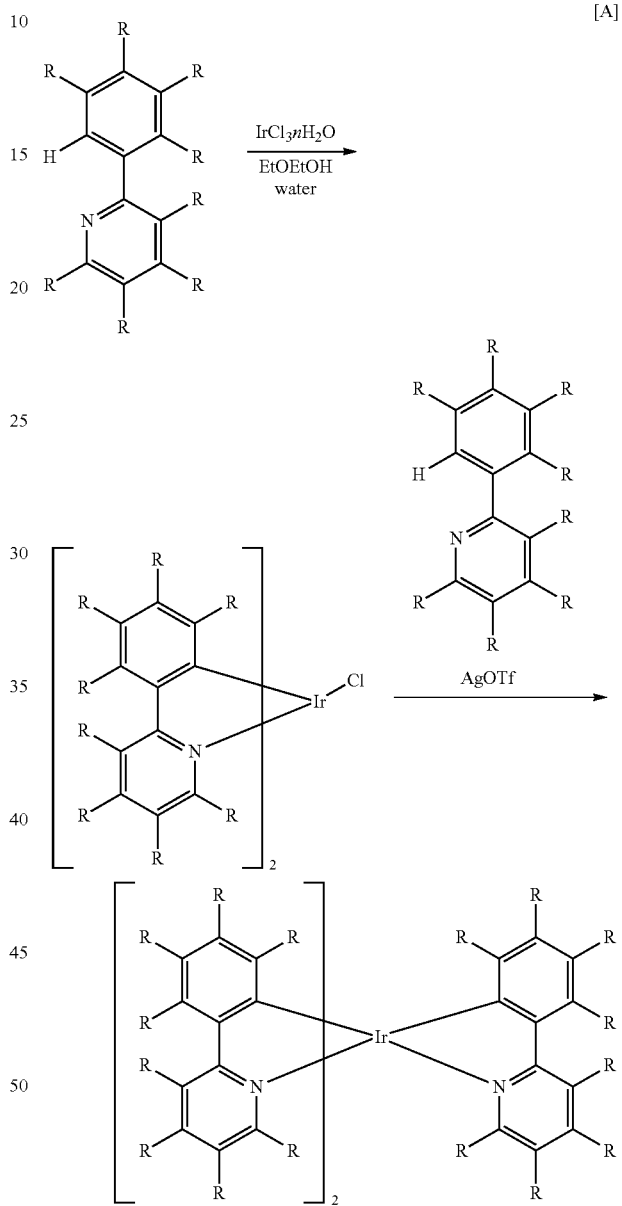

In the second stage, a halogen ion scavenger such as silver trifluoromethanesulfonate is added to bring the chloro-bridged iridium binuclear complex into contact with a newly added ligand, whereby the target complex is obtained. Typically, ethoxyethanol or diglyme is used as a solvent, but depending on the type of ligand, the reaction may be performed without a solvent, with another solvent, or with a mixture of two or more solvents. Although the halogen ion scavenger is not essential since the reaction may proceed without it, the addition of the scavenger is advantageous for increasing the reaction yield and selectively synthesizing a facial isomer having a higher quantum yield. The reaction temperature is typically, but not necessarily, in the range of 0° C. to 250° C.

Typical reaction conditions expressed by reaction formula [B] below will be described. The binuclear complex in the first stage can be synthesized in the same manner as in reaction formula [A]. In the second stage, the binuclear complex is allowed to react with 1 equivalent or more of a 1,3-dione compound such as acetylacetone and 1 equivalent or more of a basic compound, such as sodium carbonate, that can abstract active hydrogen of the 1,3-dione compound, to thereby convert into a mononuclear complex coordinated with a 1,3-dionate ligand. Typically, a solvent such as ethoxyethanol or dichloromethane that can dissolve the starting binuclear complex is used, but when the ligand is liquid, the reaction can be performed without a solvent. The reaction temperature is typically, but not necessarily, in the range of 0° C. to 200° C.

[Chem. 18]

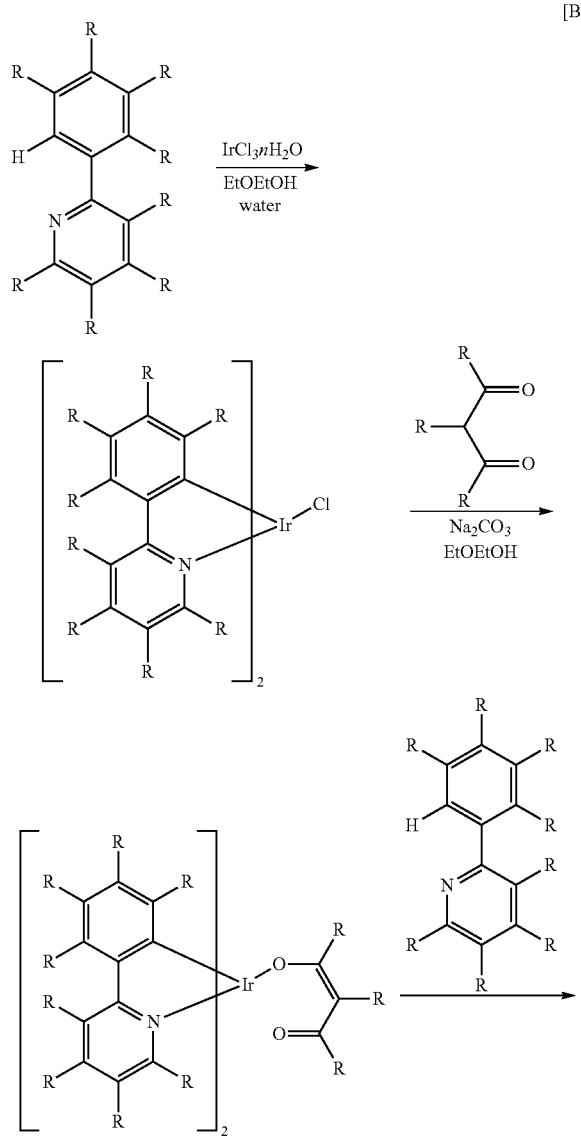

[B]

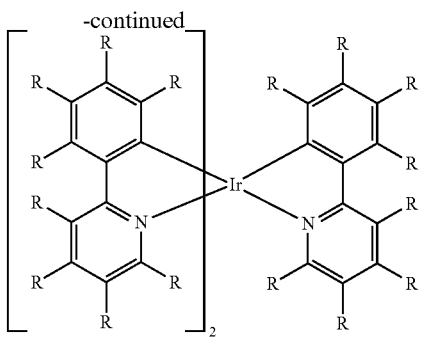

In the third stage, 1 equivalent or more of the ligand is allowed to react. The type and amount of solvent is not particularly limited, and when the ligand is liquid at a reaction temperature, the reaction may be performed without a solvent. The reaction temperature is also not particularly limited, but the reaction is often performed at a relatively high temperature of 100° C. to 300° C. because the reactivity is somewhat low. Thus, a high-boiling solvent such as glycerol is preferably used.

After the final reaction, purification is performed to remove unreacted raw materials, by-products, and the solvents. While a standard purification operation in synthetic organic chemistry can be used, purification by normal silica gel column chromatography is mainly performed as described in NPL above. As an eluent, hexane, heptane, dichloromethane, chloroform, ethyl acetate, toluene, methyl ethyl ketone, methanol, or a mixture thereof can be used. The purification may be performed more than once under different conditions. Purification operations such as other chromatography techniques (reverse phase silica gel chromatography, size exclusion chromatography, and paper chromatography), separate washing, reprecipitation, recrystallization, washing by powder suspension, and vacuum drying can be performed as required.

<Applications for Iridium Complex Compound>

The iridium complex compound of the present invention can be suitably used as a material used for an organic electroluminescent element, that is, a red-light-emitting material for an organic electroluminescent element, and can also be suitably used as a light-emitting material for an organic electroluminescent element and other light-emitting elements.

[Iridium Complex Compound-Containing Composition]

The iridium complex compound of the present invention has high solvent solubility and thus is preferably used together with a solvent. A composition of the present invention containing the iridium complex compound of the present invention and a solvent (hereinafter also referred to as "the composition of the present invention" or "the iridium complex compound-containing composition of the present invention") will be described below.

The iridium complex compound-containing composition of the present invention contains the iridium complex compound of the present invention and a solvent. The iridium complex compound-containing composition of the present invention is typically used to form a layer or a film by a wet film-forming method, and in particular, the composition is preferably used to form an organic layer of an organic electroluminescent element. In particular, the organic layer is preferably a light-emitting layer.

The iridium complex compound-containing composition of the present invention is preferably a composition for an organic electroluminescent element, and is particularly preferably used as a composition for light-emitting layer formation.

The content of the iridium complex compound of the present invention in the iridium complex compound-containing composition is typically 0.001 mass % or more, preferably 0.01 mass % or more, and typically 99.9 mass % or less, preferably 99 mass % or less. When the content of the iridium complex compound in the composition is in this range, holes and electrons are efficiently injected from adjacent layers (e.g., a hole transport layer and a hole blocking layer) into a light-emitting layer, thus leading to a low drive voltage.

The iridium complex compound of the present invention may be contained in the iridium complex compound-containing composition in the form of a single compound or a combination of two or more compounds.

The iridium complex compound-containing composition of the present invention, when used, for example, for an organic electroluminescent element, may contain, in addition to the iridium complex compound of the present invention and the solvent, a charge transport compound used for an organic electroluminescent element, particularly, for a light-emitting layer.

The iridium complex compound-containing composition of the present invention, when used to form a light-emitting layer of an organic electroluminescent element, preferably contains the iridium complex compound of the present invention as a light-emitting material and another charge transport compound as a charge transport host material.

The solvent contained in the iridium complex compound-containing composition of the present invention is a volatile liquid component used to form a layer containing the iridium complex compound by wet film-formation.

Since the iridium complex compound of the present invention serving as a solute has high solvent solubility, the solvent is not particularly limited as long as it is an organic solvent in which the charge transport compounds described later are dissolved well. Examples of preferred solvents include alkanes such as n-decane, cyclohexane, ethylcyclohexane, decalin, and bicyclohexane; aromatic hydrocarbons such as toluene, xylene, mesitylene, phenylcyclohexane, and tetralin; halogenated aromatic hydrocarbons such as chlorobenzene, dichlorobenzene, and trichlorobenzene; aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, and diphenyl ether; aromatic esters such as phenyl acetate, phenyl propionate, methyl benzoate, ethyl benzoate, propyl benzoate, and n-butyl benzoate; alicyclic ketones such as cyclohexanone, cyclooctanone, and fenchone; alicyclic alcohols such as cyclohexanol and cyclooctanol; aliphatic ketones such as methyl ethyl ketone and dibutyl ketone; aliphatic alcohols such as butanol and hexanol; and aliphatic ethers such as ethylene glycol dimethyl ether, ethylene glycol diethyl ether, and propylene glycol-1-monomethyl ether acetate (PGMEA).

Of these, alkanes and aromatic hydrocarbons are preferred. In particular, phenylcyclohexane has a viscosity and boiling point preferred for a wet film-forming process.

These solvents may be used alone, or two or more of them may be used in any combination and ratio.

The boiling point of the solvent used is typically 80° C. or more, preferably 100° C. or more, more preferably 120° C. or more, and typically 270° C. or less, preferably 250° C. or less, more preferably 230° C. or less. Below this range, the solvent may evaporate from the composition during wet film-formation, resulting in unstable film formation.

The content of the solvent in the iridium complex compound-containing composition is preferably 1 mass % or more, more preferably 10 mass % or more, particularly preferably 50 mass % or more, and preferably 99.99 mass % or less, more preferably 99.9 mass % or less, particularly preferably 99 mass % or less. The thickness of the light-emitting layer is typically about 3 to 200 nm, and when the content of the solvent is below this lower limit, the viscosity of the composition may be excessively high, resulting in low workability in film formation. When the content of the solvent is above this upper limit, the thickness of a film obtained by removing the solvent after film formation tends to be insufficient, thus resulting in unsuccessful film formation.

As the other charge transport compound that may be contained in the iridium complex compound-containing composition of the present invention, a compound conventionally used as a material for an organic electroluminescent element can be used. Examples include pyridine, carbazole, naphthalene, perylene, pyrene, anthracene, chrysene, naphthacene, phenanthrene, coronene, fluoranthene, benzophenanthrene, fluorene, acetonaphthofluoranthene, coumarin, p-bis(2-phenylethenyl)benzene, derivatives thereof, quinacridone derivatives, DCM (4-(dicyanomethylene)-2-methyl-6-(p-dimethylaminostyryl)-4H-pyran) compounds, benzopyran derivatives, rhodamine derivatives, benzothioxanthene derivatives, azabenzothioxanthene, arylamino-substituted fused aromatic ring compounds, and arylamino-substituted styryl derivatives.

These may be used alone, or two or more of them may be used in any combination and ratio.

Relative to 1 part by mass of the iridium complex compound of the present invention in the iridium complex compound-containing composition, the content of the other charge transport compound in the iridium complex compound-containing composition is typically 1,000 parts by mass or less, preferably 100 parts by mass or less, still more preferably 50 parts by mass or less, and typically 0.01 parts by mass or more, preferably 0.1 parts by mass or more, still more preferably 1 part by mass or more.

The iridium complex compound-containing composition of the present invention may optionally further contain other compounds in addition to the above-described compounds. For example, other solvents may be contained in addition to the above-described solvents. Examples of the other solvents include amides such as N,N-dimethylformamide and N,N-dimethylacetamide, and dimethylsulfoxide. These may be used alone, or two or more of them may be used in any combination and ratio.

[Organic Electroluminescent Element]

An organic electroluminescent element (hereinafter, may be referred to as "the organic electroluminescent element of the present invention") can be manufactured using the iridium complex compound of the present invention. The organic electroluminescent element of the present invention containing the iridium complex compound of the present invention will be described below.

The organic electroluminescent element of the present invention preferably includes a substrate, an anode and a cathode on the substrate, and one or more organic layers between the anode and the cathode, and at least one of the organic layers contains the iridium complex compound of the present invention. The organic layers include a light-emitting layer.

The organic layer containing the iridium complex compound of the present invention is more preferably a layer formed using the composition of the present invention, still more preferably a layer formed by a wet film-forming method. The layer formed by a wet film-forming method is preferably a light-emitting layer.

In the present invention, the term "wet film-forming method" refers to a method of forming a film in which film formation, that is, application is performed by a wet method, such as a spin coating method, a dip coating method, a die coating method, a bar coating method, a blade coating method, a roll coating method, a spray coating method, a capillary coating method, an ink-jet method, a nozzle printing method, a screen printing method, a gravure printing method, or a flexographic printing method, to form a film and the film formed by any of these methods is dried.

FIG. 1 is a schematic sectional view of an exemplary structure suitable for an organic electroluminescent element 10 of the present invention. In FIG. 1, reference numeral 1 denotes a substrate, reference numeral 2 an anode, reference numeral 3 a hole injection layer, reference numeral 4 a hole transport layer, reference numeral 5 a light-emitting layer, reference numeral 6 a hole blocking layer, reference numeral 7 an electron transport layer, reference numeral 8 an electron injection layer, and reference numeral 9 a cathode.

Materials used for the structure may be known materials and are not particularly limited. For each layer, an exemplary material and production method will be described below. It is intended that the content of any patent publications and journals cited herein may be appropriately applied or used within the common knowledge of a person skilled in the art.

<Substrate 1>

A substrate 1 serves as a support for the organic electroluminescent element and is typically, for example, a quartz or glass plate, a metal plate or metal foil, or a plastic film or sheet. In particular, the substrate 1 is preferably a glass plate or a transparent synthetic resin plate made of, for example, polyester, polymethacrylate, polycarbonate, or polysulfone. The substrate 1 is preferably made of a material with high gas barrier properties to prevent deterioration of the organic electroluminescent element due to ambient air. In particular, when a material with low gas barrier properties, such as a synthetic resin substrate, is used, a dense silicon oxide film or the like is preferably disposed on at least one surface of the substrate 1 to improve the gas barrier properties.

<Anode 2>

An anode 2 functions to inject holes into a layer on the light-emitting layer side. The anode 2 is typically made of a metal such as aluminum, gold, silver, nickel, palladium, or platinum; a metal oxide such as indium and/or tin oxide; a halogenated metal such as copper iodide; a conductive polymer such as carbon black, poly(3-methylthiophene), polypyrrole, or polyaniline; or the like.

The anode 2 is typically formed by a dry method such as a sputtering method or a vacuum deposition method. When the anode 2 is formed by using, for example, fine particles of a metal such as silver, fine particles of copper iodide or the like, carbon black, fine particles of a conductive metal oxide, or fine powder of a conductive polymer, a dispersion of such a material in an appropriate binder resin solution may be applied to the substrate to form the anode 2. In the case of a conductive polymer, the anode 2 can be formed by forming a thin film directly on a substrate through electrolytic polymerization or applying the conductive polymer on a substrate (Appl. Phys. Lett., vol. 60, p. 2711, 1992).

The anode 2 typically has a single-layer structure but may have a multilayer structure as appropriate. When the anode 2 has a multilayer structure, a different conductive material may be stacked on a first anode layer.

The thickness of the anode 2 may be determined according to, for example, the transparency required and the material used. When particularly high transparency is required, the thickness is preferably such that the visible light transmittance of the anode 2 is 60% or more, more preferably 80% or more. The thickness of the anode 2 is typically 5 nm or more, preferably 10 nm or more, and typically 1,000 nm or less, preferably 500 nm or less.

When transparency is not required, the anode 2 may have any thickness according to, for example, the strength required. In this case, the anode 2 may have the same thickness as the substrate 1.

When a film is formed on a surface of the anode 2, it is preferable to perform, before the film formation, a treatment with ultraviolet rays+ozone, oxygen plasma, argon plasma, or the like to thereby remove impurities on the anode and adjust the ionization potential thereof to improve hole injection ability.

<Hole Injection Layer 3>

The layer that functions to transport holes from the anode 2 side to the light-emitting layer 5 side is typically called a hole injection-transport layer or a hole transport layer. When there are two or more layers that function to transport holes from the anode 2 side to the light-emitting layer 5 side, the layer closer to the anode 2 side may be called a hole injection layer 3. The hole injection layer 3 is preferably used to enhance the function of transporting holes from the anode 2 to the light-emitting layer 5 side. When the hole injection layer 3 is used, the hole injection layer 3 is typically formed on the anode 2.

The thickness of the hole injection layer 3 is typically 1 nm or more, preferably 5 nm or more, and typically 1,000 nm or less, preferably 500 nm or less.

The hole injection layer 3 may be formed by a vacuum deposition method or a wet film-forming method. In terms of high film formability, the hole injection layer 3 is preferably formed by a wet film-forming method.

The hole injection layer 3 preferably contains a hole-transporting compound, more preferably contains a hole-transporting compound and an electron-accepting compound. Furthermore, the hole injection layer 3 preferably contains a cation radical compound, particularly preferably contains a cation radical compound and a hole-transporting compound.

(Hole-Transporting Compound)

A composition for hole injection layer formation typically contains a hole-transporting compound that will form the hole injection layer 3.

In the case of a wet film-forming method, typically, a solvent is further contained. The composition for hole injection layer formation preferably has a high hole transport ability and can efficiently transport injected holes. Thus, the composition preferably has high hole mobility and is less likely to generate trapping impurities, for example, during production or use. In addition, the composition preferably has high stability, a low ionization potential, and high transparency to visible light. Particularly when the hole injection layer 3 is in contact with the light-emitting layer 5, the composition preferably does not quench light emitted from the light-emitting layer 5 and does not form an exciplex together with the light-emitting layer 5 to reduce light emission efficiency.

The hole-transporting compound is preferably a compound having an ionization potential of 4.5 eV to 6.0 eV from the viewpoint of a barrier to charge injection from the anode 2 to the hole injection layer 3. Examples of the hole-transporting compound include aromatic amine compounds, phthalocyanine compounds, porphyrin compounds, oligothiophene compounds, polythiophene compounds, benzylphenyl compounds, compounds having tertiary amines connected to each other through a fluorene group, hydrazone compounds, silazane compounds, and quinacridone compounds.

Among the above exemplary compounds, aromatic amine compounds are preferred, and aromatic tertiary amine compounds are particularly preferred, in terms of amorphous properties and visible light transmittance. Aromatic tertiary amine compounds are compounds having an aromatic tertiary amine structure and also include compounds having a group derived from an aromatic tertiary amine.

The type of aromatic tertiary amine compound is not particularly limited, but it is preferable to use a polymer compound having a weight average molecular weight of 1,000 or more and 1,000,000 or less (polymerized compound having a series of repeating units) because uniform light emission is readily provided due to the surface-smoothing effect. Examples of preferred aromatic tertiary amine polymer compounds include a polymer compound having a repeating unit represented by formula (I) below.

[Chem. 19]

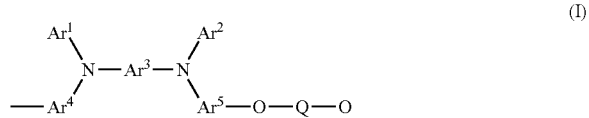

(I)

In formula (I), $Ar^1$ and $Ar^2$ each independently represent an optionally substituted aromatic group or an optionally substituted heteroaromatic group. $Ar^3$ to $Ar^5$ each independently represent an optionally substituted aromatic group or an optionally substituted heteroaromatic group. Q represents a linking group selected from the group of linking groups given below. Among $Ar^1$ to $Ar^5$, two groups bonded to the same N atom may be bonded together to form a ring.

The linking groups are given below.

[Chem. 20]

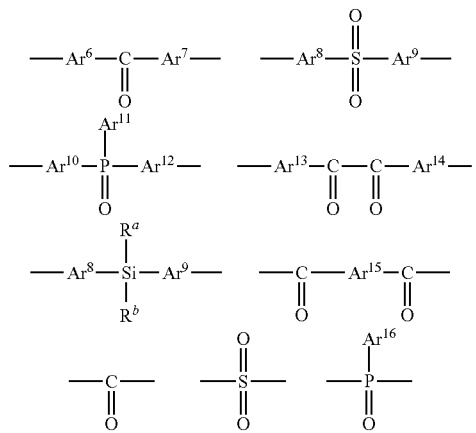

In each of the above formulae, $Ar^6$ to $Ar^{16}$ each independently represent an optionally substituted aromatic group or an optionally substituted heteroaromatic group. $R^a$ to $R^b$ each independently represent a hydrogen atom or a substituent.

In terms of solubility, heat resistance, and hole injection transport ability of the polymer compound, the aromatic groups and the heteroaromatic groups represented by $Ar^1$ to $Ar^{16}$ are each preferably a group derived from a benzene ring, a naphthalene ring, a phenanthrene ring, a thiophene ring, or a pyridine ring, more preferably a group derived from a benzene ring or a naphthalene ring.

Specific examples of the aromatic tertiary amine polymer compound having the repeating unit represented by formula (I) include compounds described in International Publication No. 2005/089024.

(Electron-Accepting Compound)

The hole injection layer 3 preferably contains an electron-accepting compound because the electric conductivity of the hole injection layer 3 can be improved through oxidation of the hole-transporting compound.

The electron-accepting compound is preferably a compound having oxidizing power and capable of accepting one electron from the above hole-transporting compound. Specifically, a compound having an electron affinity of 4 eV or more is preferred, and a compound having an electron affinity of 5 eV or more is more preferred.

Examples of such electron-accepting compounds include one or more compounds selected from the group consisting of triaryl boron compounds, halogenated metals, Lewis acids, organic acids, onium salts, salts of an arylamine and a halogenated metal, and salts of an arylamine and a Lewis acid. Specific examples include onium salts with a substituted organic group, such as 4-isopropyl-4'-methyldiphenyliodonium tetrakis(pentafluorophenyl)borate and triphenylsulfonium tetrafluoroborate (International Publication No. 2005/089024); high-valent inorganic compounds such as iron (III) chloride (Japanese Unexamined Patent Application Publication No. 11-251067) and ammonium peroxodisulfate; cyano compounds such as tetracyanoethylene; aromatic boron compounds such as tris(pentafluorophenyl)borane (Japanese Unexamined Patent Application Publication No. 2003-31365); fullerene derivatives; and iodine.

(Cation Radical Compound)

The cation radical compound is preferably an ionic compound composed of a cation radical, which is a chemical species resulting from the removal of one electron from a hole-transporting compound, and a counter anion. When the cation radical is derived from a hole-transporting polymer compound, the cation radical has a structure resulting from the removal of one electron from the repeating unit of the polymer compound.

The cation radical is preferably a chemical species that results from the removal of one electron from any of the compounds listed above as a hole-transporting compound. A chemical species that results from the removal of one electron from a compound preferred as a hole-transporting compound is suitable in terms of, for example, amorphous properties, visible light transmittance, heat resistance, and solubility.

The cation radical compound can be produced by mixing the hole-transporting compound and the electron-accepting compound. The mixing of the hole-transporting compound and the electron-accepting compound causes electrons to migrate from the hole-transporting compound to the electron-accepting compound, as a result of which a cationic compound composed of a cation radical of the hole-transporting compound and a counter anion is produced.

Polymer compound-derived cation radical compounds such as PEDOT/PSS (Adv. Mater., 2000, vol. 12, p. 481) and emeraldine hydrochloride (J. Phys. Chem., 1990, vol. 94, p 7716) are produced also through oxidation polymerization (dehydrogenation polymerization).

As used herein, oxidation polymerization refers to oxidizing a monomer, in an acidic solution, chemically using peroxodisulfate or the like or electrochemically. In the case of oxidation polymerization (dehydrogenation polymerization), a monomer is oxidized to form a polymer, while one electron is removed from the repeating unit of the polymer to produce a cation radical, with an anion derived from an acidic solution serving as a counter anion.

(Formation of Hole Injection Layer 3 by Wet Film-Forming Method)

When the hole injection layer 3 is formed by a wet film-forming method, it is typically formed by mixing a material that will form the hole injection layer 3 with an appropriate solvent (a solvent for a hole injection layer) to prepare a composition for film formation (composition for hole injection layer formation), applying the composition for hole injection layer formation onto a layer (typically, the anode 2) corresponding to an underlayer of the hole injection layer 3 by a wet film-forming method to form a film, and drying the film. The drying of the formed film can be performed in the same manner as the drying in the formation of the light-emitting layer 5 by a wet film-forming method.

The concentration of the hole-transporting compound in the composition for hole injection layer formation, although not particularly limited as long as the effects of the present invention are not greatly impaired, is preferably low in terms of thickness uniformity, and is preferably high in terms of defect resistance of the hole injection layer 3. The concentration of the hole-transporting compound in the composition for hole injection layer formation is preferably 0.01 mass % or more, more preferably 0.1 mass % or more, particularly preferably 0.5 mass % or more, and preferably 70 mass % or less, more preferably 60 mass % or less, particularly preferably 50 mass % or less.

Examples of the solvent include ether solvents, ester solvents, aromatic hydrocarbon solvents, and amide solvents.

Examples of ether solvents include aliphatic ethers such as ethylene glycol dimethyl ether, ethylene glycol diethyl ether, and propylene glycol-1-monomethyl ether acetate (PGMEA) and aromatic ethers such as 1,2-dimethoxybenzene, 1,3-dimethoxybenzene, anisole, phenetole, 2-methoxytoluene, 3-methoxytoluene, 4-methoxytoluene, 2,3-dimethylanisole, and 2,4-dimethylanisole.

Examples of ester solvents include aromatic esters such as phenyl acetate, phenyl propionate, methyl benzoate, ethyl benzoate, propyl benzoate, and n-butyl benzoate.

Examples of aromatic hydrocarbon solvents include toluene, xylene, cyclohexylbenzene, 3-isopropylbiphenyl, 1,2,3,4-tetramethylbenzene, 1,4-diisopropylbenzene, and methylnaphthalene.

Examples of amide solvents include N,N-dimethylformamide and N,N-dimethylacetamide.

Other solvents such as dimethylsulfoxide can also be used.

The formation of the hole injection layer 3 by a wet film-forming method is typically performed by preparing the composition for hole injection layer formation, then applying the composition onto a layer (typically, the anode 2) corresponding to an underlayer of the hole injection layer 3 to form a film, and drying the film. In forming the hole injection layer 3, typically, the coating film is dried, for example, by heating or vacuum drying after the film formation.

(Formation of Hole Injection Layer 3 by Vacuum Deposition Method)

When the hole injection layer 3 is formed by a vacuum deposition method, it is typically formed as described below. One or more of the constituent materials (e.g., the hole-transporting compound and the electron-accepting compound) of the hole injection layer 3 are placed in a crucible mounted in a vacuum chamber (when two or more materials are used, they are typically placed in different crucibles), and the vacuum chamber is evacuated with a vacuum pump to about $10^{-4}$ Pa. Thereafter, the crucible is heated (when two or more materials are used, the crucibles are typically each heated), and the material in the crucible is evaporated while controlling the amount of evaporation (when two or more materials are used, the materials are typically independently evaporated while controlling the amount of evaporation) to form the hole injection layer 3 on the anode 2 on a substrate placed so as to face the crucible. When two or more materials are used, a mixture thereof may be placed in a crucible, and heated and evaporated to form the hole injection layer 3.

The degree of vacuum during the deposition is not particularly limited as long as the effects of the present invention are not greatly impaired, and is typically $0.1 \times 10^{-6}$ Torr ($0.13 \times 10^{-4}$ Pa) or more and $9.0 \times 10^{-6}$ Torr ($12.0 \times 10^{-4}$ Pa) or less. The rate of deposition is not particularly limited as long as the effects of the present invention are not greatly impaired, and is typically 0.1 Å/s or more and 5.0 Å/s or less. The film formation temperature during the deposition is not particularly limited as long as the effects of the present invention are not greatly impaired, and is preferably 10° C. or more and 50° C. or less.

<Hole Transport Layer 4>

A hole transport layer 4 is a layer that functions to transport holes from the anode 2 side to the light-emitting layer 5 side. Although the hole transport layer 4 is not essential in the organic electroluminescent element of the present invention, this layer is preferably provided in order to enhance the function of transporting holes from the anode 2 to the light-emitting layer 5. When the hole transport layer 4 is provided, the hole transport layer 4 is typically formed between the anode 2 and the light-emitting layer 5. When the hole injection layer 3 is present, the hole transport layer 4 is formed between the hole injection layer 3 and the light-emitting layer 5.

The thickness of the hole transport layer 4 is typically 5 nm or more, preferably 10 nm or more, and typically 300 nm or less, preferably 100 nm or less.

The hole transport layer 4 may be formed by a vacuum deposition method or a wet film-forming method. In terms of high film formability, the hole transport layer 4 is preferably formed by a wet film-forming method.

The hole transport layer 4 typically contains a hole-transporting compound that will form the hole transport layer 4. Specific examples of the hole-transporting compound contained in the hole transport layer 4 include aromatic diamines which contain two or more tertiary amines and in which two or more fused aromatic rings are substituted with nitrogen atoms, such as 4,4'-bis[N-(1-naphthyl)-N-phenylamino]biphenyl (Japanese Unexamined Patent Application Publication No. 5-234681); aromatic amine compounds having a starburst structure, such as 4,4',4"-tris (1-naphthylphenylamino)triphenylamine (J. Lumin., vols.

72-74, p. 985, 1997); aromatic amine compounds composed of a tetramer of triphenylamine (Chem. Commun., p. 2175, 1996); spiro compounds such as 2,2',7,7'-tetrakis-(diphenylamino)-9,9'-spirobifluorene (Synth. Metals, vol. 91, p. 209, 1997); and carbazole derivatives such as 4,4'-N,N'-dicarbazolebiphenyl. Polyvinylcarbazole, polyvinyltriphenylamine (Japanese Unexamined Patent Application Publication No. 7-53953), polyarylene ether sulfone containing tetraphenylbenzidine (Polym. Adv. Tech., vol. 7, p. 33, 1996), and the like can also be preferably used.

(Formation of Hole Transport Layer 4 by Wet Film-Forming Method)

When the hole transport layer 4 is formed by a wet film-forming method, it is typically formed as in the case where the hole injection layer 3 is formed by a wet film-forming method, except that the composition for hole injection layer formation is replaced with a composition for hole transport layer formation.

When the hole transport layer 4 is formed by a wet film-forming method, the composition for hole transport layer formation typically further contains a solvent. The solvent used for the composition for hole transport layer formation may be the same solvent as used for the composition for hole injection layer formation.

The concentration of the hole-transporting compound in the composition for hole transport layer formation may be in the same range as that of the concentration of the hole-transporting compound in the composition for hole injection layer formation.

The formation of the hole transport layer 4 by a wet film-forming method can be performed in the same manner as the formation of the hole injection layer 3.

(Formation of Hole Transport Layer 4 by Vacuum Deposition Method)

Also when the hole transport layer 4 is formed by a vacuum deposition method, it can be typically formed as in the case where the hole injection layer 3 is formed by a vacuum deposition method, except that the constituent materials of the hole injection layer 3 are replaced with constituent materials of the hole transport layer 4. The film formation conditions, including the degree of vacuum during the deposition, the rate of deposition, and the temperature, may be the same as the conditions for the vacuum deposition of the hole injection layer 3.

<Light-Emitting Layer 5>

The light-emitting layer 5 is a layer that functions to emit light upon being excited by recombination of holes injected from the anode 2 and electrons injected from a cathode 9 in response to an electric field applied between the pair of electrodes. The light-emitting layer 5 is a layer formed between the anode 2 and the cathode 9. When the hole injection layer 3 is present on the anode 2, the light-emitting layer 5 is formed between the hole injection layer 3 and the cathode 9, and when the hole transport layer 4 is present on the anode 2, the light-emitting layer 5 is formed between the hole transport layer 4 and the cathode 9.

The thickness of the light-emitting layer 5, although not particularly limited as long as the effects of the present invention are not greatly impaired, is preferably large to prevent defects of the film, and is preferably small to help achieve a low drive voltage. The thickness of the light-emitting layer 5 is preferably 3 nm or more, more preferably 5 nm or more, and preferably 200 nm or less, more preferably 100 nm or less.

The light-emitting layer 5 contains at least a material having light-emitting properties (light-emitting material), and preferably also contains a material having charge transport ability (charge-transporting material). It is only required that at least one of the light-emitting layers contain the iridium complex compound of the present invention as a light-emitting material, and other light-emitting materials may be used as appropriate. Light-emitting materials other than the iridium complex compound of the present invention will be described below in detail.

(Light-Emitting Material)

The light-emitting material is not particularly limited as long as it emits light at a desired emission wavelength and the effects of the present invention are not impaired, and a known light-emitting material can be used. The light-emitting material may be a fluorescent material or a phosphorescent material, and is preferably a material with good light emission efficiency, preferably a phosphorescent material from the viewpoint of internal quantum efficiency.

Examples of the fluorescent material include the following materials.

Examples of fluorescent materials that provide blue-light emission (blue fluorescent materials) include naphthalene, perylene, pyrene, anthracene, coumarin, chrysene, p-bis(2-phenylethenyl)benzene, and derivatives thereof.

Examples of fluorescent materials that provide green-light emission (green fluorescent materials) include quinacridone derivatives, coumarin derivatives, and aluminum complexes such as $Al(C_9H_6NO)_3$.

Examples of fluorescent materials that provide yellow-light emission (yellow fluorescent materials) include rubrene and perimidone derivatives.

Examples of fluorescent materials that provide red-light emission (red fluorescent materials) include DCM (4-(dicyanomethylene)-2-methyl-6-(p-dimethylaminostyryl)-4H-pyran) compounds, benzopyran derivatives, rhodamine derivatives, benzothioxanthene derivatives, and azabenzothioxanthene.

Examples of the phosphorescent material include organometallic complexes containing a metal selected from groups 7 to 11 of the long-form periodic table (hereinafter, when the term "the periodic table" is used, it refers to the long-form periodic table, unless otherwise specified). Preferred examples of the metal selected from groups 7 to 11 of the periodic table include ruthenium, rhodium, palladium, silver, rhenium, osmium, iridium, platinum, and gold.

The ligand of such an organometallic complex is preferably a ligand in which a (hetero)aryl group is linked to pyridine, pyrazole, phenanthroline, or the like, such as a (hetero)arylpyridine ligand or a (hetero)arylpyrazole ligand, particularly preferably a phenylpyridine ligand or a phenylpyrazole ligand. Here, (hetero)aryl means an aryl group or a heteroaryl group.

Specific examples of preferred phosphorescent materials include phenylpyridine complexes such as tris(2-phenylpyridine)iridium, tris(2-phenylpyridine)ruthenium, tris(2-phenylpyridine)palladium, bis(2-phenylpyridine)platinum, tris(2-phenylpyridine)osmium, and tris(2-phenylpyridine)rhenium; and porphyrin complexes such as platinum octaethylporphyrin, platinum octaphenylporphyrin, palladium octaethylporphyrin, and palladium octaphenylporphyrin.

Examples of polymeric light-emitting materials include polyfluorene materials such as poly(9,9-dioctylfluorene-2,7-diyl), poly[(9,9-dioctylfluorene-2,7-diyl)-co-(4,4'-(N-(4-sec-butylphenyl))diphenylamine)], and poly[(9,9-dioctylfluorene-2,7-diyl)-co-(1,4-benzo{2,1'-3}-triazole)]; and polyphenylenevinylene materials such as poly[2-methoxy-5-(2-ethylhexyloxy)-1,4-phenylenevinylene].

(Charge-Transporting Material)

The charge-transporting material is a material having a positive charge (hole) or negative charge (electron) transport ability and may be any known material as long as the effects of the present invention are not impaired.

The charge-transporting material may be, for example, a compound conventionally used for the light-emitting layer 5 of an organic electroluminescent element, and, in particular, is preferably a compound used as a host material of the light-emitting layer 5.

Specific examples of the charge-transporting material include the compounds exemplified as the hole-transporting compound of the hole injection layer 3, such as aromatic amine compounds, phthalocyanine compounds, porphyrin compounds, oligothiophene compounds, polythiophene compounds, benzylphenyl compounds, compounds having tertiary amines connected to each other through a fluorene group, hydrazone compounds, silazane compounds, silanamine compounds, phosphamine compounds, and quinacridone compounds; and electron-transporting compounds such as anthracene compounds, pyrene compounds, carbazole compounds, pyridine compounds, phenanthroline compounds, oxadiazole compounds, and silole compounds.

Also preferred for use as the charge-transporting material are, for example, the compounds exemplified as the hole-transporting compound of the hole transport layer 4, such as aromatic diamines which contain two or more tertiary amines and in which two or more fused aromatic rings are substituted with nitrogen atoms, as typified by 4,4'-bis[N-(1-naphthyl)-N-phenylamino]biphenyl (Japanese Unexamined Patent Application Publication No. 5-234681); aromatic amine compounds having a starburst structure, such as 4,4',4"-tris(1-naphthylphenylamino)triphenylamine (J. Lumin., vols. 72-74, p. 985, 1997); aromatic amine compounds composed of a tetramer of triphenylamine (Chem. Commun., p. 2175, 1996); fluoren compounds such as 2,2',7,7'-tetrakis-(diphenylamino)-9,9'-spirobifluorene (Synth. Metals, vol. 91, p. 209, 1997); and carbazole compounds such as 4,4'-N,N'-dicarbazolebiphenyl. Examples of the charge-transporting material also include oxadiazole compounds such as 2-(4-biphenylyl)-5-(p-tert-butylphenyl)-1,3,4-oxadiazole (tBu-PBD) and 2,5-bis(1-naphthyl)-1,3,4-oxadiazole (BND); silole compounds such as 2,5-bis(6'-(2', 2"-bipyridyl))-1,1-dimethyl-3,4-diphenylsilole (PyPySPyPy); and phenanthroline compounds such as bathophenanthroline (BPhen) and 2,9-dimethyl-4,7-diphenyl-1,10-phenanthroline (BCP, bathocuproine).

(Formation of Light-Emitting Layer 5 by Wet Film-Forming Method)

The light-emitting layer 5 may be formed by a vacuum deposition method or a wet film-forming method. In terms of high film formability, the wet film-forming method is preferred.

When the light-emitting layer 5 is formed by a wet film-forming method, it is typically formed as in the case where the hole injection layer 3 is formed by a wet film-forming method, except that the composition for hole injection layer formation is replaced with a composition for light-emitting layer formation prepared by mixing a material that will form the light-emitting layer 5 with an appropriate solvent (a solvent for a light-emitting layer). In the present invention, the iridium complex compound-containing composition of the present invention is preferably used as the composition for light-emitting layer formation.

Examples of the solvent include the solvents exemplified for the formation of the hole injection layer 3, such as ether solvents, ester solvents, aromatic hydrocarbon solvents, and amide solvents; and alkane solvents, halogenated aromatic hydrocarbon solvents, aliphatic alcohol solvents, alicyclic alcohol solvents, aliphatic ketone solvents, and alicyclic ketone solvents. The solvent used is as exemplified also as the solvent of the iridium complex compound-containing composition of the present invention. Specific examples of the solvent are given below, but other solvents may also be used as long as the effects of the present invention are not impaired.

Examples include aliphatic ether solvents such as ethylene glycol dimethyl ether, ethylene glycol diethyl ether, and propylene glycol-1-monomethyl ether acetate (PGMEA); aromatic ether solvents such as 1,2-dimethoxybenzene, 1,3-dimethoxybenzene, anisole, phenetole, 2-methoxytoluene, 3-methoxytoluene, 4-methoxytoluene, 2,3-dimethylanisole, 2,4-dimethylanisole, and diphenyl ether; aromatic ester solvents such as phenyl acetate, phenyl propionate, methyl benzoate, ethyl benzoate, propyl benzoate, and n-butyl benzoate; aromatic hydrocarbon solvents such as toluene, xylene, mesitylene, cyclohexylbenzene, tetralin, 3-isopropylbiphenyl, 1,2,3,4-tetramethylbenzene, 1,4-diisopropylbenzene, and methylnaphthalene; amide solvents such as N,N-dimethylformamide and N,N-dimethylacetamide; alkane solvents such as n-decane, cyclohexane, ethylcyclohexane, decalin, and bicyclohexane; halogenated aromatic hydrocarbon solvents such as chlorobenzene, dichlorobenzene, and trichlorobenzene; aliphatic alcohol solvents such as butanol and hexanol; alicyclic alcohol solvents such as cyclohexanol and cyclooctanol; aliphatic ketone solvents such as methyl ethyl ketone and dibutyl ketone; and alicyclic ketone solvents such as cyclohexanone, cyclooctanone, and fenchone. Of these, alkane solvents and aromatic hydrocarbon solvents are particularly preferred.

To form a more uniform film, the solvent is preferably evaporated from a freshly formed liquid film at an appropriate rate. Thus, the boiling point of the solvent used, as described above, is typically 80° C. or more, preferably 100° C. or more, more preferably 120° C. or more, and typically 270° C. or less, preferably 250° C. or less, more preferably 230° C. or less.

The solvent may be used in any amount as long as the effects of the present invention are not greatly impaired, but the total content of the solvent in the composition for light-emitting layer formation, that is, the iridium complex compound-containing composition is preferably high in terms of ease of film-forming operation due to a low viscosity, and is preferably low in terms of ease of film formation due to a thick film. As described above, the content of the solvent in the iridium complex compound-containing composition is preferably 1 mass % or more, more preferably 10 mass % or more, particularly preferably 50 mass % or more, and preferably 99.99 mass % or less, more preferably 99.9 mass % or less, particularly preferably 99 mass % or less.

The solvent can be removed after the wet film formation, for example, by heating or pressure reduction. The heating means used for heating is preferably a clean oven or a hot plate because heat is uniformly applied to the whole film.

The heating temperature in the heating process, although not particularly limited as long as the effects of the present invention are not greatly impaired, is preferably high in terms of reduction in drying time, and is preferably low in terms of reduction in damage to the materials. The upper limit of the heating temperature is typically 250° C. or less, preferably 200° C. or less, more preferably 150° C. or less. The lower limit of the heating temperature is typically 30° C. or more, preferably 50° C. or more, more preferably 80°

C. or more. Temperatures over the upper limit are higher than the level of heat resistance of a commonly used charge transport material or phosphorescent material and may disadvantageously cause decomposition or crystallization. When the heating temperature is below the lower limit, removal of the solvent disadvantageously requires a long time. The heating temperature in the heating process is appropriately determined according to the boiling point of the solvent in the composition for light-emitting layer formation, the vapor pressure, the heat resistance of the materials, and the heating conditions.

(Formation of Light-Emitting Layer 5 by Vacuum Deposition Method)

When the light-emitting layer 5 is formed by a vacuum deposition method, it is typically formed as described below. One or more of the constituent materials (e.g., the light-emitting material and the charge transport compound) of the light-emitting layer 5 are placed in a crucible mounted in a vacuum chamber (when two or more materials are used, they are typically placed in different crucibles), and the vacuum chamber is evacuated with a vacuum pump to about $10^{-4}$ Pa. Thereafter, the crucible is heated (when two or more materials are used, the crucibles are typically each heated), and the material in the crucible is evaporated while controlling the amount of evaporation (when two or more materials are used, the materials are typically independently evaporated while controlling the amount of evaporation) to form the light-emitting layer 5 on the hole injection layer 3 or the hole transport layer 4 placed so as to face the crucible. When two or more materials are used, a mixture thereof may be placed in a crucible, and heated and evaporated to form the light-emitting layer 5.

The degree of vacuum during the deposition is not particularly limited as long as the effects of the present invention are not greatly impaired, and is typically $0.1 \times 10^{-6}$ Torr ($0.13 \times 10^{-4}$ Pa) or more and $9.0 \times 10^{-6}$ Torr ($12.0 \times 10^{-4}$ Pa) or less. The rate of deposition is not particularly limited as long as the effects of the present invention are not greatly impaired, and is typically 0.1 Å/s or more and 5.0 Å/s or less. The film formation temperature during the deposition is not particularly limited as long as the effects of the present invention are not greatly impaired, and is preferably 10° C. or more and 50° C. or less.

<Hole Blocking Layer 6>

A hole blocking layer 6 may be disposed between the light-emitting layer 5 and an electron injection layer 8 described later. The hole blocking layer 6 is a layer stacked on the light-emitting layer 5 so as to be in contact with a surface of the light-emitting layer 5 on the cathode 9 side.

The hole blocking layer 6 serves to prevent holes moving from the anode 2 from reaching the cathode 9 and to efficiently transport electrons injected from the cathode 9 toward the light-emitting layer 5. The material forming the hole blocking layer 6 is required to have physical properties such as high electron mobility, low hole mobility, a large energy gap (difference between HOMO and LUMO), and a high excited triplet level (T1).

Examples of materials of the hole blocking layer 6 that satisfy such requirements include mixed ligand complexes such as bis(2-methyl-8-quinolinolate) (phenolate)aluminum and bis(2-methyl-8-quinolinolate) (triphenylsilanolate)aluminum; metal complexes such as a bis(2-methyl-8-quinolate)aluminum-μ-oxo-bis-(2-methyl-8-quinolinolate)aluminum dinuclear metal complex; styryl compounds such as distyrylbiphenyl derivatives (Japanese Unexamined Patent Application Publication No. 11-242996); triazole derivatives such as 3-(4-biphenylyl)-4-phenyl-5(4-tert-butylphenyl)-1,2,4-triazole (Japanese Unexamined Patent Application Publication No. 7-41759); and phenanthroline derivatives such as bathocuproine (Japanese Unexamined Patent Application Publication No. 10-79297). A compound having at least one pyridine ring substituted at the 2-, 4-, and 6-positions described in International Publication No. 2005/022962 is also preferred as the material of the hole blocking layer 6.

The hole blocking layer 6 may be formed by any method, and can be formed in the same manner as the light-emitting layer 5.

The thickness of the hole blocking layer 6, although not particularly limited as long as the effects of the present invention are not greatly impaired, is typically 0.3 nm or more, preferably 0.5 nm or more, and typically 100 nm or less, preferably 50 nm or less.

<Electron Transport Layer 7>

An electron transport layer 7 is disposed between the light-emitting layer 5 or the hole blocking layer 6 and the electron injection layer 8 for the purpose of further improving the current efficiency of the element.

The electron transport layer 7 is formed of a compound that, between the electrodes under an electric field, is capable of efficiently transporting electrons injected from the cathode 9 toward the light-emitting layer 5. The electron-transporting compound used for the electron transport layer 7 needs to be a compound into which electrons from the cathode 9 or the electron injection layer 8 are injected with high efficiency and which has high electron mobility so that injected electrons can be efficiently transported.

Examples of electron-transporting compounds that satisfy such requirements include metal complexes such as aluminum complexes of 8-hydroxyquinoline (Japanese Unexamined Patent Application Publication No. 59-194393), metal complexes of 10-hydroxybenzo[h]quinoline, oxadiazole derivatives, distyrylbiphenyl derivatives, silole derivatives, 3-hydroxyflavone metal complexes, 5-hydroxyflavone metal complexes, benzoxazole metal complexes, benzothiazole metal complexes, trisbenzimidazolylbenzene (U.S. Pat. No. 5,645,948), quinoxaline compounds (Japanese Unexamined Patent Application Publication No. 6-207169), phenanthroline derivatives (Japanese Unexamined Patent Application Publication No. 5-331459), 2-t-butyl-9,10-N,N'-dicyanoanthraquinonediimine, n-type hydrogenated amorphous silicon carbide, n-type zinc sulfide, and n-type zinc selenide.

The thickness of the electron transport layer 7 is typically 1 nm or more, preferably 5 nm or more, and typically 300 nm or less, preferably 100 nm or less.

The electron transport layer 7 is formed by being stacked on the light-emitting layer 5 or the hole blocking layer 6 by a wet film-forming method or a vacuum deposition method as with the light-emitting layer 5. Typically, a vacuum deposition method is used.

<Electron Injection Layer 8>

The electron injection layer 8 serves to efficiently inject electrons injected from the cathode 9 into the electron transport layer 7 or the light-emitting layer 5.

To achieve efficient electron injection, the material forming the electron injection layer 8 is preferably a metal with a low work function. Examples include alkali metals such as sodium and cesium and alkaline-earth metals such as barium and calcium.

The thickness of the electron injection layer 8 is preferably 0.1 to 5 nm.

To interpose, as the electron injection layer 8, an ultrathin insulating film (about 0.1 to 5 nm thick) of LiF, $MgF_2$, $Li_2O$, $Cs_2CO_3$, or the like between the cathode 9 and the electron transport layer 7 is also an effective means for improving the efficiency of the element (Appl. Phys. Lett., vol. 70, p. 152, 1997; Japanese Unexamined Patent Application Publication No. 10-74586; IEEE Trans. Electron. Devices, vol. 44, p. 1245, 1997; and SID 04 Digest, p. 154).

Furthermore, to dope an organic electron transport material, as typified by nitrogen-containing heterocyclic compounds such as bathophenanthroline and metal complexes such as aluminum complexes of 8-hydroxyquinoline, with an alkali metal such as sodium, potassium, cesium, lithium, or rubidium (described in Japanese Unexamined Patent Application Publication No. 10-270171, Japanese Unexamined Patent Application Publication No. 2002-100478, Japanese Unexamined Patent Application Publication No. 2002-100482, etc.) is preferred because the electron injection/transport ability can be improved to achieve excellent film quality. In this case, the thickness of the film is typically 5 nm or more, preferably 10 nm or more, and typically 200 nm or less, preferably 100 nm or less.

The electron injection layer 8 is formed by being stacked on the light-emitting layer 5 or on the hole blocking layer 6 or the electron transport layer 7 thereon by a wet film-forming method or a vacuum deposition method as with the light-emitting layer 5.

Details in the case of a wet film-forming method are the same as in the case of the light-emitting layer 5.

<Cathode 9>

The cathode 9 serves to inject electrons into a layer on the light-emitting layer 5 side (e.g., the electron injection layer 8 or the light-emitting layer 5). The material of the cathode 9 may be the same as the material used for the anode 2. For efficient electron injection, it is preferable to use a metal with a low work function, such as tin, magnesium, indium, calcium, aluminum, silver, or an alloy thereof. Examples of the material of the cathode 9 include alloy electrodes with a low work function, such as magnesium-silver alloys, magnesium-indium alloys, and aluminum-lithium alloys.

In terms of element stability, a metal layer having a high work function and stable to the atmosphere is preferably stacked on the cathode 9 to protect the cathode 9 formed of a metal with a low work function. Examples of the metal stacked include metals such as aluminum, silver, copper, nickel, chromium, gold, and platinum.

The thickness of the cathode is typically the same as that of the anode 2.

<Other Constituent Layers>

While the description has been made mainly in the context of an element with a layer structure illustrated in FIG. 1, any desired layers, in addition to the layers described above, may be disposed between the anode 2 and the light-emitting layer 5 and between the cathode 9 and the light-emitting layer 5 in the organic electroluminescent element of the present invention, or any of the layers other than the light-emitting layer 5 may be omitted, as long as the performance of the element is not impaired.

For example, to dispose an electron blocking layer between the hole transport layer 4 and the light-emitting layer 5 is also effective for the same purpose as that of the hole blocking layer 6. The electron blocking layer serves to prevent electrons moving from the light-emitting layer 5 from reaching the hole transport layer 4, thereby increasing the probability of recombination of electrons with holes in the light-emitting layer 5 and confining the resultant excitons in the light-emitting layer 5, and also serves to efficiently transport holes injected from the hole transport layer 4 toward the light-emitting layer 5.

The electron blocking layer is required to have properties such as high hole transport ability, a large energy gap (difference between HOMO and LUMO), and a high excited triplet level (T1).

When the light-emitting layer 5 is formed by a wet film-forming method, the electron blocking layer is also preferably formed by a wet film-forming method for ease of element production.

Thus, the electron blocking layer also preferably has suitability for wet film formation, and examples of materials used for such electron blocking layers include copolymers of dioctylfluorene and triphenylamine, as typified by F8-TFB (International Publication No. 2004/084260).

The structure in FIG. 1 may be reversed; specifically, the cathode 9, the electron injection layer 8, the electron transport layer 7, the hole blocking layer 6, the light-emitting layer 5, the hole transport layer 4, the hole injection layer 3, and the anode 2 may be stacked in this order on the substrate 1. It is also possible to dispose the organic electroluminescent element of the present invention between two substrates at least one of which is highly transparent.

A structure formed of a plurality of the layer structures illustrated in FIG. 1 stacked on top of each other (a structure formed of a plurality of light-emitting units stacked on top of each other) is also possible. In this case, from the viewpoint of light emission efficiency and drive voltage, it is more preferable to use, for example, $V_2O_5$ as a charge generation layer in place of the interfacial layer (when the anode is ITO and the cathode is Al, the interfacial layer means these two layers) between the stages (between the light-emitting units) because such a configuration reduces the barrier between the stages.

The present invention can be applied to any of a single organic electroluminescent element, organic electroluminescent elements configured in an array arrangement, and a structure in which anodes and cathodes are arranged in an X-Y matrix.

[Display Device and Illumination Device]

A display device and an illumination device can be manufactured using the organic electroluminescent element of the present invention. The display device and the illumination device of the present invention may be of any type and may have any structure, and can be assembled according to an ordinary method by using the organic electroluminescent element of the present invention.

For example, the display device and the illumination device of the present invention can be formed by a method as described in "Organic EL Display" (Ohmsha, Ltd., published Aug. 20, 2004, written by Shizuo Tokito, Chihaya Adachi, and Hideyuki Murata) using the organic electroluminescent element of the present invention.

EXAMPLES

The present invention will now be described in more detail with reference to examples. The present invention is not limited to the following examples, and any modifications can be made without departing from the scope of the present invention.

In the following Synthesis Examples, all reactions were performed under a stream of nitrogen. Solvents and solutions used in reactions were deaerated by an appropriate method such as bubbling with nitrogen before use.

Synthesis of Iridium Complex Compound Synthesis Example 1: Synthesis of Comparative Compound 1

[Chem. 21]

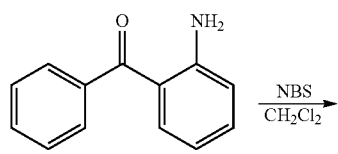

In a 500 cc round-bottomed flask, 12.53 g of 2-aminobenzophenone and 120 cc of dichloromethane were placed. The flask was placed in an ice bath. A slurry mixture of 11.43 g of N-bromosuccinimide and 30 cc of dichloromethane was added thereto. The mixture was stirred for 10 minutes and then stirred at room temperature for 1 hour. The mixture was allowed to stand overnight, washed with 500 cc of water, and phase-separated. After extraction was performed with 200 cc of dichloromethane from the aqueous phase, the resulting dichloromethane solution was combined with the oil phase. The mixture was dried over 20 g of magnesium sulfate. Removal of the solvent under reduced pressure gave a residue, which was purified by silica gel column chromatography (neutral silica gel: 500 cc, dichloromethane/hexane=7/3 to 85/15) to obtain 16.67 g of 2-amino-4-bromobenzophenone as a yellow solid.

[Chem. 28]

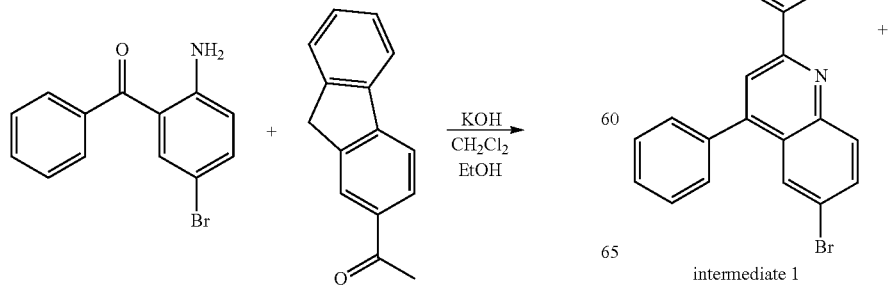

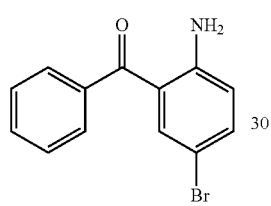

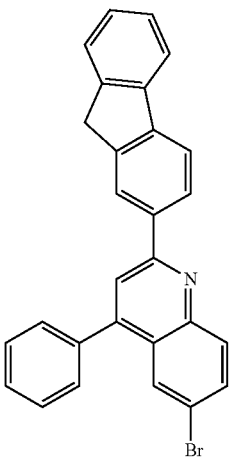

intermediate 1

In a 100 cc round-bottomed flask, 10.02 g of 2-amino-4-bromobenzophenone, 10.02 g of 2-acetylfluorene, 4.28 g of potassium hydroxide, and 100 cc of ethanol were placed. The mixture was stirred in an oil bath at 100° C. for 2.5 hours and then cooled to room temperature. The resulting solid precipitate was filtered, washed with three 50-cc portions of ethanol, and dried to give 7.47 g of intermediate 1 as a pale yellow solid.

[Chem. 23]

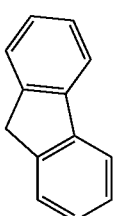

+

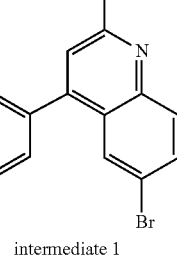

intermediate 1

-continued

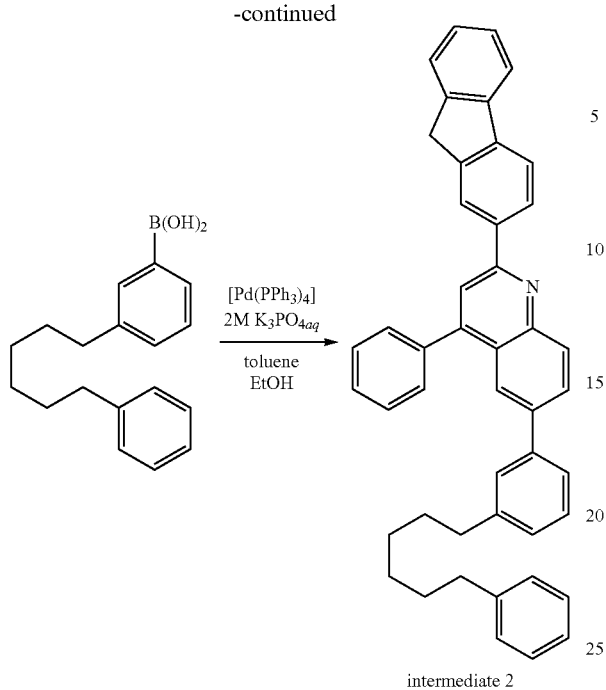

intermediate 2

In a 300 cc round-bottomed flask, 7.47 g of intermediate 1, 5.44 g of 3-(6-phenyl-n-hexyl)phenylboronic acid (see WO2016-194784A1), 1.21 g of tetrakis(triphenylphosphine)palladium(0), 30 cc of a 2 mol/L aqueous solution of tripotassium phosphate, 65 cc of toluene, and 30 cc of ethanol were placed. The mixture was stirred in an oil bath at 100° C. for 1.5 hours and then cooled to room temperature. Removal of the solvent under reduced pressure gave a residue, which was purified by silica gel column chromatography (neutral gel: 750 cc, dichloromethane/hexane=1/1) to obtain 7.83 g of intermediate 2 as a yellow solid.

[Chem. 24]

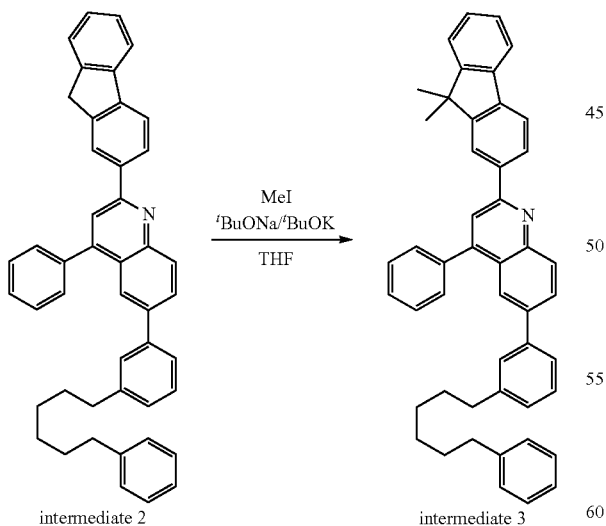

intermediate 2     intermediate 3

First, 7.83 g of intermediate 2 was placed in a 1 L round-bottomed flask and dissolved in 50 cc of dry tetrahydrofuran and 6.50 g of methyl iodide, followed by addition of 3.74 g of sodium tert-butoxide. The mixture was stirred at room temperature for 5.5 hours. During the stirring, 3.74 g of potassium tert-butoxide was added 3 hours later, and 4.29 g of methyl iodide was added 5 hours later. Upon completion of the reaction, the mixture was filtered. The filter cake was washed with 50 cc of tetrahydrofuran. The filtrate was combined with the washings. Removal of the solvent left a residue. The residue was purified by silica gel column chromatography (neutral silica gel: 400 cc, dichloromethane/hexane=1/1) to give 4.69 g of intermediate 3 as a colorless amorphous solid.

[Chem. 25]

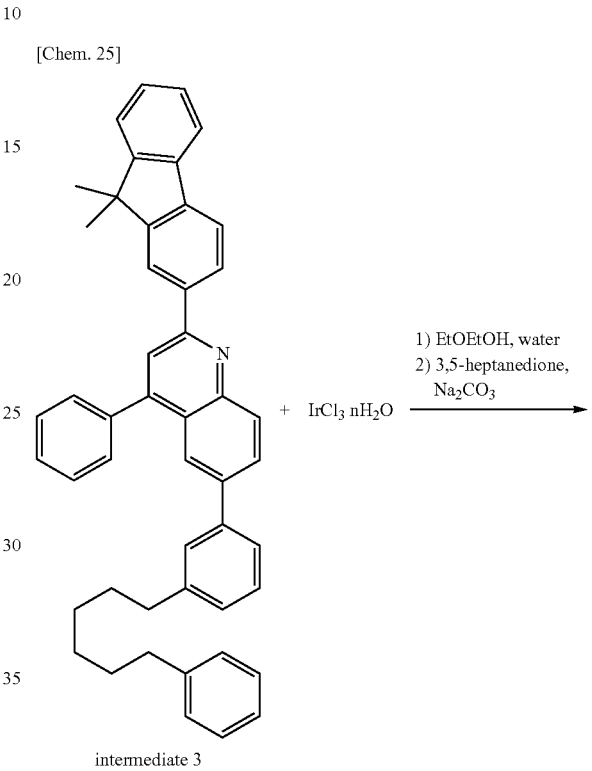

intermediate 3

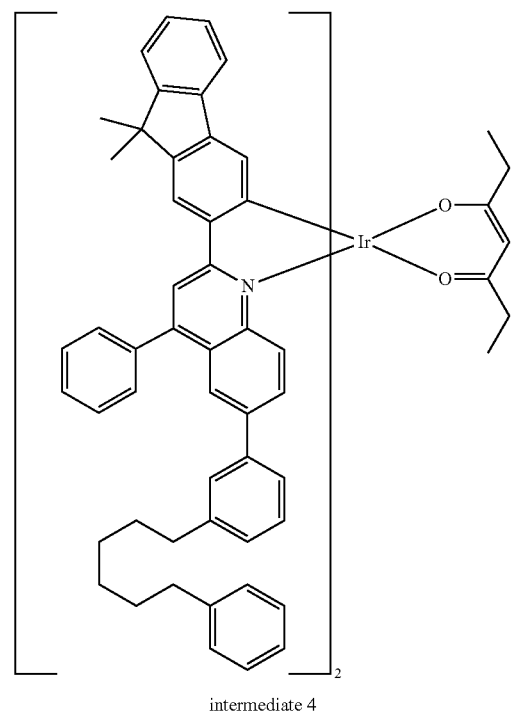

intermediate 4

In a 100 cc round-bottomed flask equipped with a Dimroth condenser having a bypass tube, 1.53 g of intermediate 3 and 0.46 g of iridium chloride n-hydrate (available from Furuya Metal Co., Ltd., iridium content: 51.25 wt %) were placed. Then 25 cc of 2-ethoxyethanol and 5 cc of water were added thereto. The mixture was stirred in an oil bath at 135° C. for 5 hours and then stirred at 140° C. for 3 hours. The mixture was allowed to stand at room temperature overnight and then stirred again at 140° C. for 9.5 hours. During this operation, 10 cc of a distilled liquid was removed through the bypass tube. The reaction mixture was cooled to room temperature, followed by addition of 1.60 g of 3,5-heptanedione and 1.56 g of sodium carbonate. The mixture was stirred in an oil bath at 135° C. for 40 minutes. Removal of the solvent under reduced pressure gave a residue, which was purified by silica gel column chromatography (neutral silica gel, dichloromethane) to obtain 1.74 g of intermediate 4 as a red amorphous solid.

[Chem. 26]

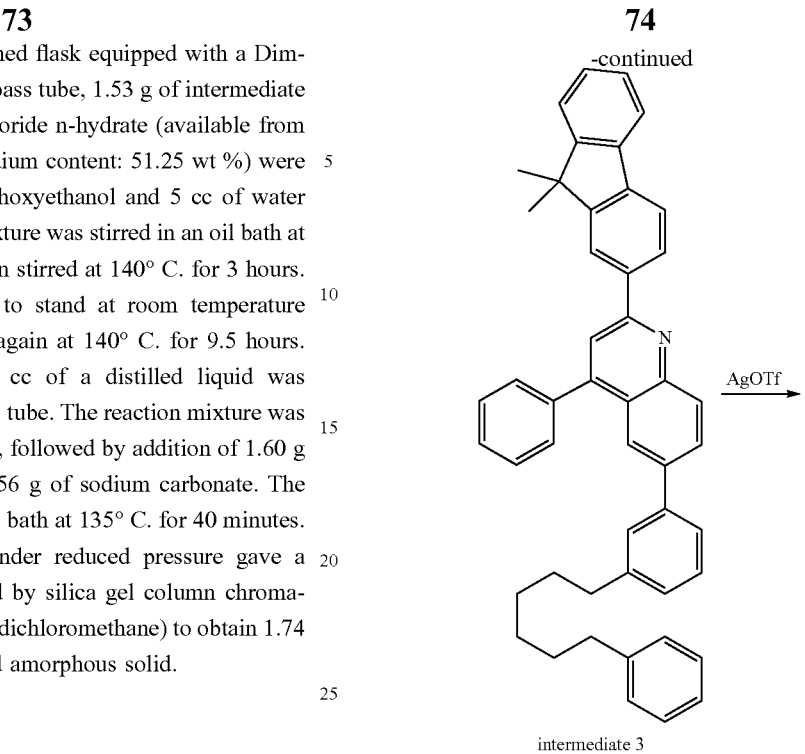

In a 100 cc round-bottomed flask, 1.74 g of intermediate 4 and 1.41 g of intermediate 3 were placed. The mixture was heated to 270° C. under stirring into a homogeneous melt with an aluminum block heater (RCH-1000, available from EYELA). The melt was cooled to 240° C., followed by addition of 0.2 g of silver(I) trifluoromethanesulfonate. The mixture was stirred at 240° C. for 80 minutes and cooled to room temperature. The resulting mixture was subjected to purification by silica gel column chromatography (neutral silica gel, dichloromethane/hexane) to give 0.83 g of comparative compound 1 as a dark red solid.

Synthesis Example 2: Synthesis of Compound 1

[Chem. 27]

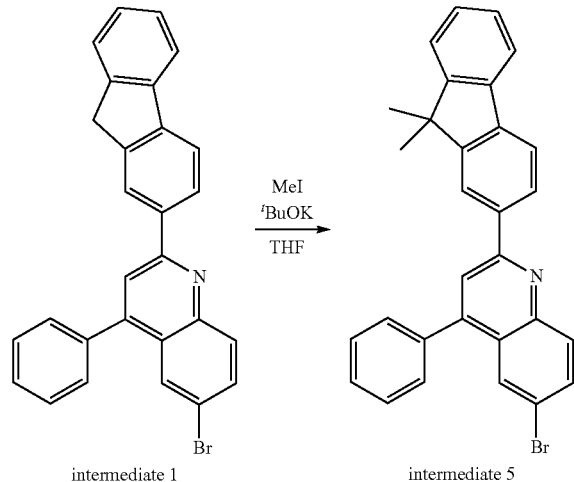

First, 10.4 g of intermediate 1 and 150 ml of dry tetrahydrofuran were placed in a 500 ml round-bottomed flask to prepare a solution. The flask was placed in an ice-water bath, followed by addition of 7.77 g of potassium tert-butoxide. The mixture was stirred for 10 minutes, followed by addition of 4.5 ml of methyl iodide. After the heat release was no longer observed, the mixture was stirred at room temperature for 2.5 hours, followed by addition of 150 ml of water. The precipitated solid was filtered, washed with water and methanol, dried to give 10.91 g of intermediate 5 as a pale orange solid.

[Chem. 28]

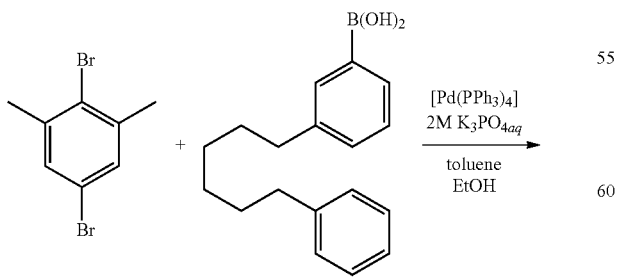

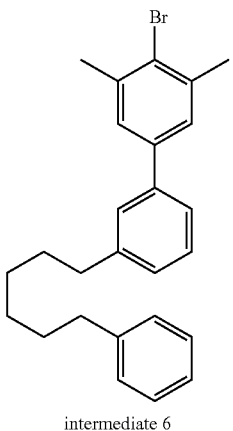

In a 500 ml round-bottomed flask, 9.0 g of 2,6-dibromo-m-xylene, 8.0 g of 3-(6-phenyl-n-hexyl)phenylboronic acid, 0.79 g of tetrakis(triphenylphosphine)palladium(0), 43 ml of a 2 mol/L aqueous solution of tripotassium phosphate, 60 ml of toluene, and 30 ml of ethanol were added. The mixture was stirred in an oil bath at 90° C. for 5 hours and then cooled to room temperature. Removal of the solvent under reduced pressure gave a residue, which was purified by silica gel column chromatography (neutral gel: 750 cc, dichloromethane/hexane=1/9) to obtain 11.3 g of intermediate 6 as a yellow solid.

[Chem. 29]

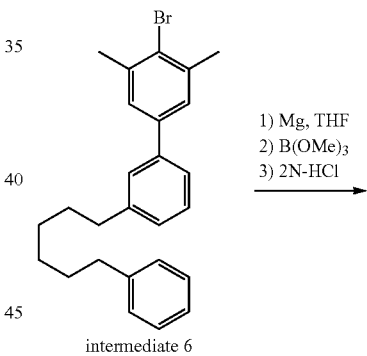

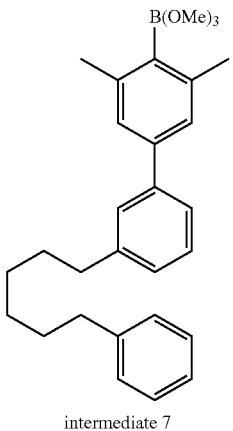

In a 300 ml four-necked flask, 0.84 g of magnesium turnings was placed. A solution of intermediate 6 dissolved in 25 ml of dry tetrahydrofuran was added dropwise via a syringe at room temperature over 10 minutes. The syringe was rinsed with 10 ml of tetrahydrofuran, and then the washings were also added dropwise thereto. The flask was placed in an oil bath at 90° C., followed by stirring for 70 minutes. The mixture was cooled in a dry ice-acetone bath, followed by dropwise addition of 5 ml of trimethoxyboran dissolved in 45 ml of dry tetrahydrofuran via a syringe over 10 minutes. The mixture was stirred at room temperature for 30 minutes, followed by addition of 20 ml of tetrahydrofuran. The mixture was stirred in an oil bath at 60° C. for 70 minutes. Then 40 ml of 2 N HCl was added thereto while the mixture was cooled in an ice-water bath under stirring. After foaming was completed, the extraction was performed with 100 ml of dichloromethane, followed by drying over magnesium sulfate. Removal of the solvent under reduced pressure gave 12.33 g of intermediate 7 as a pale brown oily substance in the form of a mixture with tetrahydrofuran.

[Chem. 30]

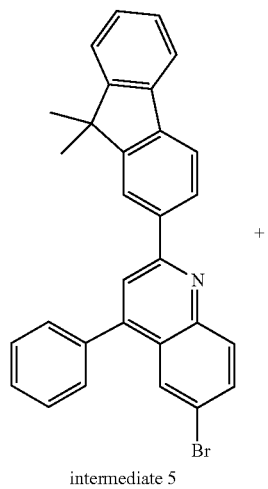

intermediate 5

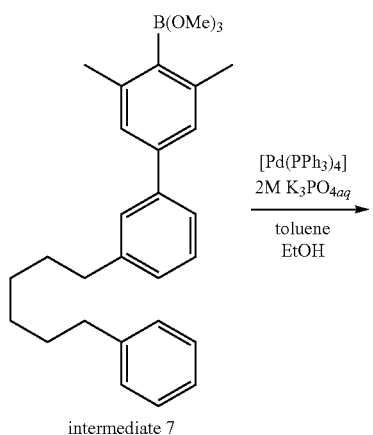

intermediate 7

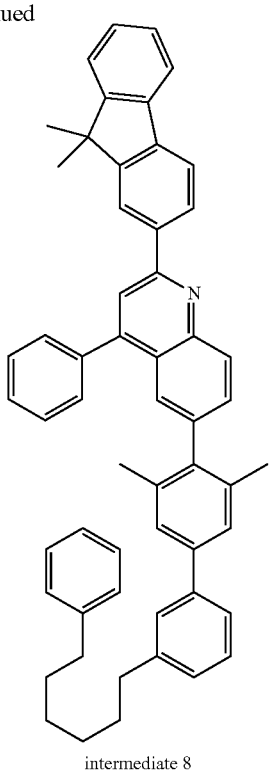

intermediate 8

In a 500 ml round-bottomed flask, 7.53 g of intermediate 5, 12.33 g of intermediate 7, 0.92 g of tetrakis(triphenylphosphine)palladium(0), 12.5 g of barium hydroxide octahydrate, 130 ml of 1,2-dimethoxyethane, and 20 ml of water were placed. The mixture was stirred in an oil bath at 100° C. for 1.5 hours. During the stirring, 2.14 g of intermediate 5 was further added at 40 minutes after the initiation of the reaction. The mixture was cooled to room temperature and filtered. The filtrate was concentrated under reduced pressure to give a residue, which was extracted with 150 ml of ethyl acetate and 50 ml of water. The oil phase was washed with saturated brine, dried over magnesium sulfate, and filtered. Removal of the solvent under reduced pressure gave a residue, which was purified by silica gel column chromatography (neutral gel: 700 cc, dichloromethane/hexane=1/1) to obtain 13.55 g of intermediate 8 as a pale yellow solid.

[Chem. 31]

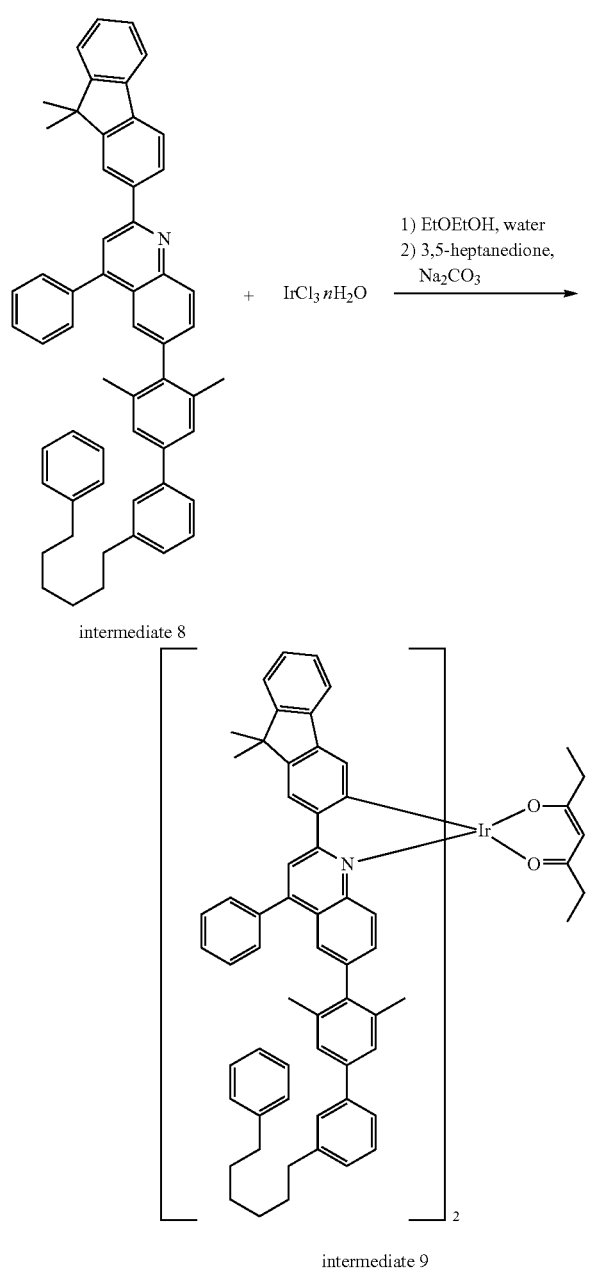

intermediate 8 intermediate 9

In a 200 cc round-bottomed flask equipped with a Dimroth condenser having a bypass tube, 4.32 g of intermediate 8 and 1.05 g of iridium chloride n-hydrate (available from Furuya Metal Co., Ltd., iridium content: 51.25 wt %) were placed. Then 60 ml of 2-ethoxyethanol and 10 ml of water were added thereto. The mixture was stirred in an oil bath at 125° C. for 1 hour and then stirred at 135° C. for 4.5 hours. The mixture was allowed to stand at room temperature overnight and then stirred again at 135° C. for 6.5 hours. During this operation, 12 ml of a distilled liquid was removed through the bypass tube. The reaction mixture was cooled to room temperature, followed by addition of 1.5 g of 3,5-heptanedione and 2.36 g of sodium carbonate. The mixture was stirred in an oil bath at 135° C. for 40 minutes. Removal of the solvent under reduced pressure gave a residue, which was purified by silica gel column chromatography (neutral silica gel, dichloromethane/hexane) to obtain 4.50 g of intermediate 9 as a red amorphous solid.

[Chem. 32]

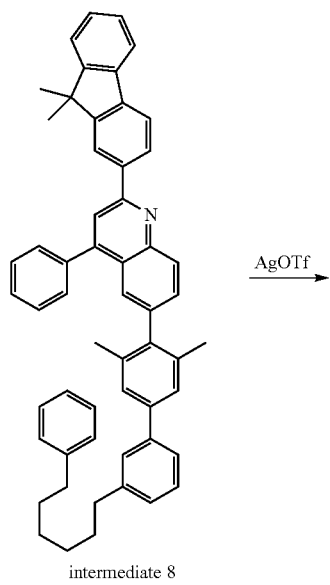

intermediate 8

-continued

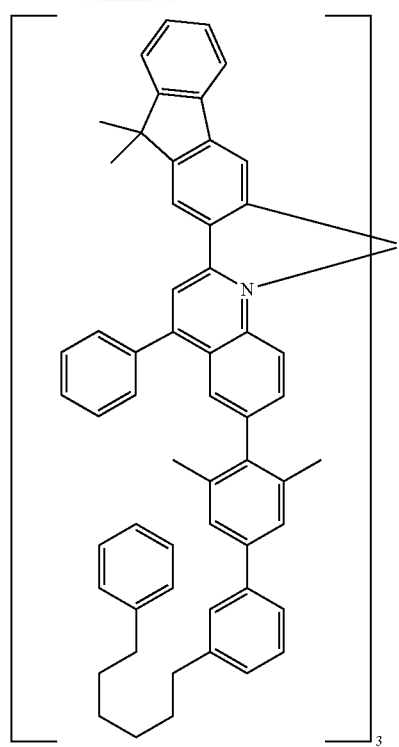

compound 1

In a 100 ml round-bottomed flask, 4.50 g of intermediate 9 and 1.53 g of intermediate 8 were placed. The mixture was heated to 200° C. in an oil bath under stirring into a homogeneous melt, followed by addition of 0.53 g of silver(I) trifluoromethanesulfonate. The mixture was stirred at 240° C. for 1 hour and then cooled to room temperature. The resulting mixture was subjected to purification by silica gel column chromatography (neutral silica gel, dichloromethane/hexane) to give 0.98 g of compound 1 as a dark red solid.

Synthesis Example 3: Synthesis of Compound 2

[Chem. 33]

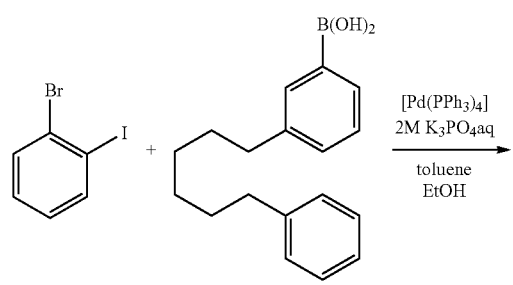

-continued

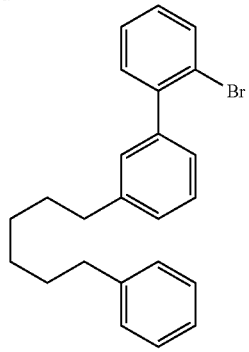

In a 500 ml round-bottomed flask, 25.20 g of 2-bromoiodobenzene, 20.41 g of 3-(6-phenyl-n-hexyl)phenylboronic acid, 3.60 g of tetrakis(triphenylphosphine)palladium (0), 90 ml of a 2 M aqueous solution of tripotassium phosphate, 100 ml of toluene, and 70 ml of ethanol were placed. The mixture was stirred in an oil bath at 105° C. for 2 hours, followed by removal of the aqueous phase. Removal of the solvent under reduced pressure gave a residue, which was purified by silica gel column chromatography (neutral silica gel, dichloromethane/hexane) to obtain 23.56 g of 3-(6-phenyl-n-hexyl)-2'-bromo-1,1'-biphenyl as a colorless oily substance.

[Chem. 34]

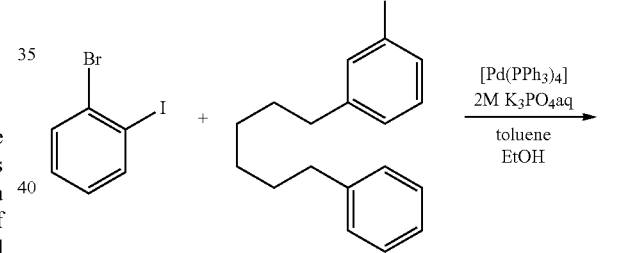

In a 1 L round-bottomed flask, 23.56 g of 3-(6-phenyl-n-hexyl)-2'-bromo-1,1'-biphenyl, 17.56 g of bis(pinacolato)diboron, 29.66 g of potassium acetate, 1.50 g of [1,1'-bis(diphenylphosphino)ferrocene]palladium(II) dichloride dichloromethane adduct, and 200 ml of dimethyl sulfoxide were placed. The mixture was stirred in an oil bath at 90° C. for a total of 15 hours. During the stirring, 2.11 g of [1,1'-bis(diphenylphosphino)ferrocene]palladium(II) dichloride dichloromethane adduct was added thereto. After the reaction was completed, 1 L of water and 0.45 L of dichloromethane were added for phase separation. The oil phase was washed with 0.5 L of water, dried over a volume of about 20 ml of magnesium sulfate, and filtered. Removal of the solvent under reduced pressure gave a residue, which was purified by silica gel column chromatography (neutral gel, dichloromethane/hexane) to obtain 23.16 g of intermediate 10 as a dark yellow oily substance. The wiggly line in the structural formula of intermediate 10 is used to indicate a mixture of rotamers.

[Chem. 35]

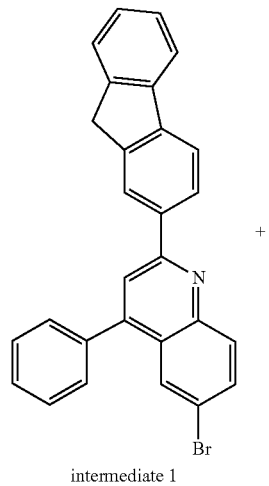

intermediate 1

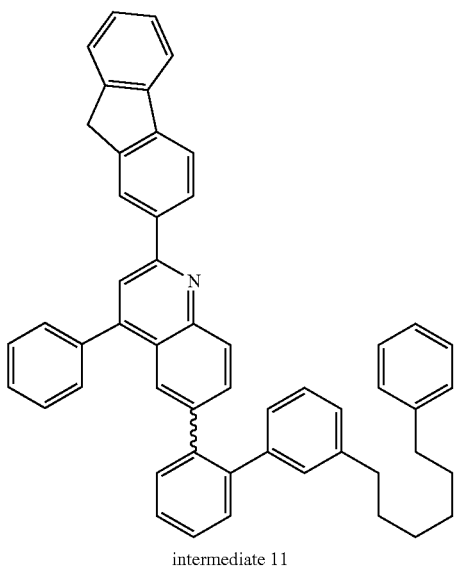

intermediate 11

In a 1 L round-bottomed flask, 14.76 g of intermediate 1, 23.16 g of intermediate 10, 2.88 g of tetrakis(triphenylphosphine)palladium(0), 70 ml of a 2 M aqueous solution of tripotassium phosphate, 160 ml of toluene, and 80 ml of ethanol were placed. The mixture was stirred in an oil bath at 105° C. for 2 hours, followed by removal of the aqueous phase. Removal of the solvent under reduced pressure gave a residue, which was purified by silica gel column chromatography (neutral silica gel, dichloromethane/hexane) to obtain 21.98 g of intermediate 11 as a cream-colored solid.

[Chem. 36]

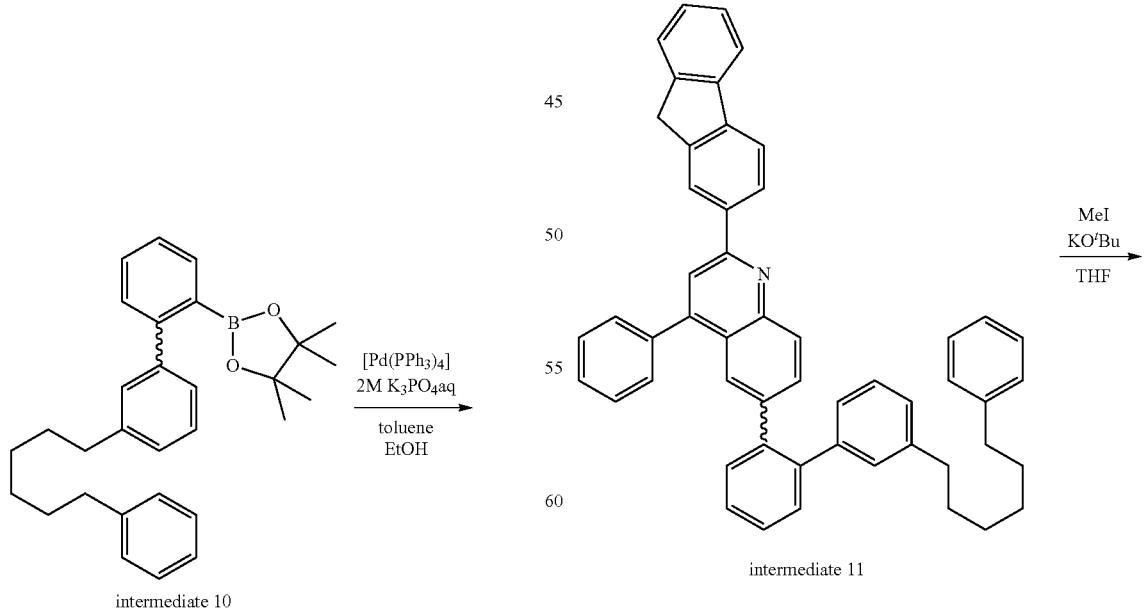

-continued

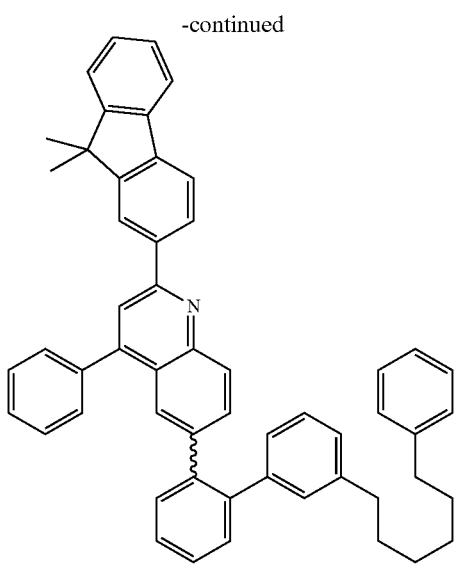

intermediate 12

In a 1 L round-bottomed flask, 21.98 g of intermediate 11, 11.0 g of potassium tert-butoxide, and 200 ml of tetrahydrofuran were placed. The mixture was stirred at room temperature to prepare a black suspension. The flask was placed in an ice-water bath, followed by injection of 6.0 ml of methyl iodide over 1 minute. The mixture was stirred at room temperature for 2 hours. After the solvent was removed under reduced pressure, 0.5 L of water and 0.3 L of dichloromethane were added for phase separation. The oil phase was dried over magnesium sulfate. Removal of the solvent from the oil phase under reduced pressure gave a solid, which was purified by silica gel column chromatography (neutral silica gel, dichloromethane/hexane) to obtain 16.18 g of intermediate 12 as a yellow amorphous substance.

[Chem. 37]

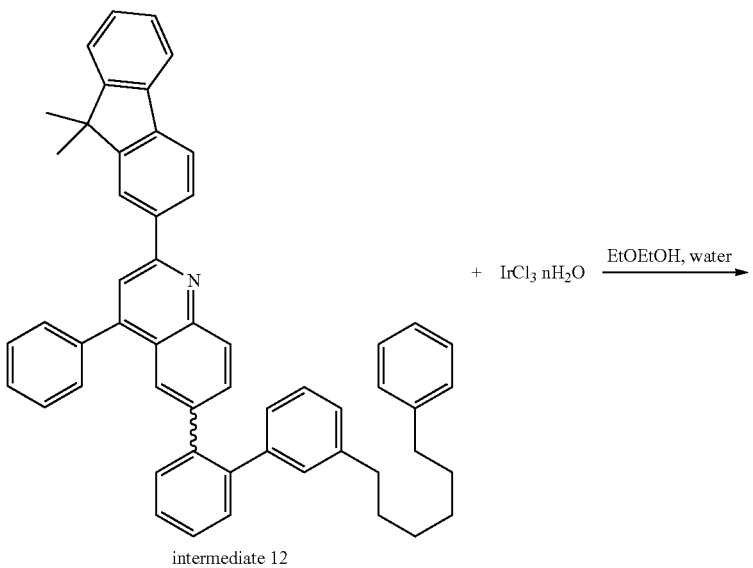

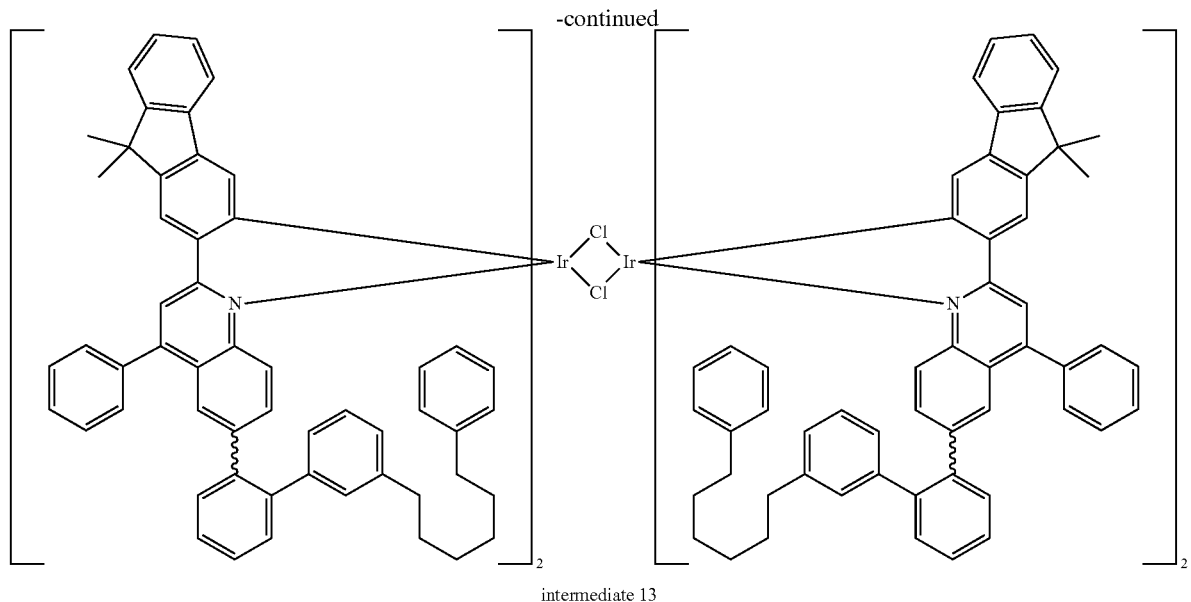

intermediate 13

In a 200 cc round-bottomed flask equipped with a Dimroth condenser having a bypass tube, 11.75 g of intermediate 12 and 3.10 g of iridium chloride n-hydrate (available from Furuya Metal Co., Ltd., iridium content: 51.25 wt %) were placed. Then 150 ml of 2-ethoxyethanol and 25 ml of water were added thereto. The mixture was stirred in an oil bath at 135° C. for 2 hours and then stirred at 140° C. for 6.5 hours. The mixture was allowed to stand at room temperature overnight and then stirred again at 140° C. for 10 hours. During this operation, 55 ml of a distilled liquid was removed through the bypass tube. Removal of the solvent under reduced pressure gave a residue, which was purified by silica gel column chromatography (neutral silica gel, dichloromethane/hexane) to obtain 6.98 g of dark red intermediate 13.

[Chem. 38]

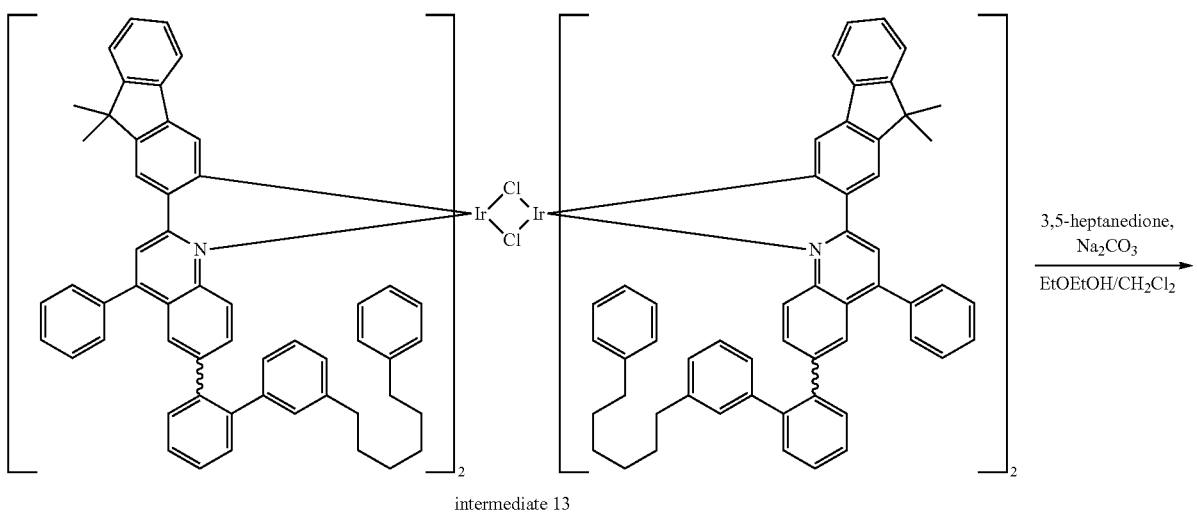

intermediate 13

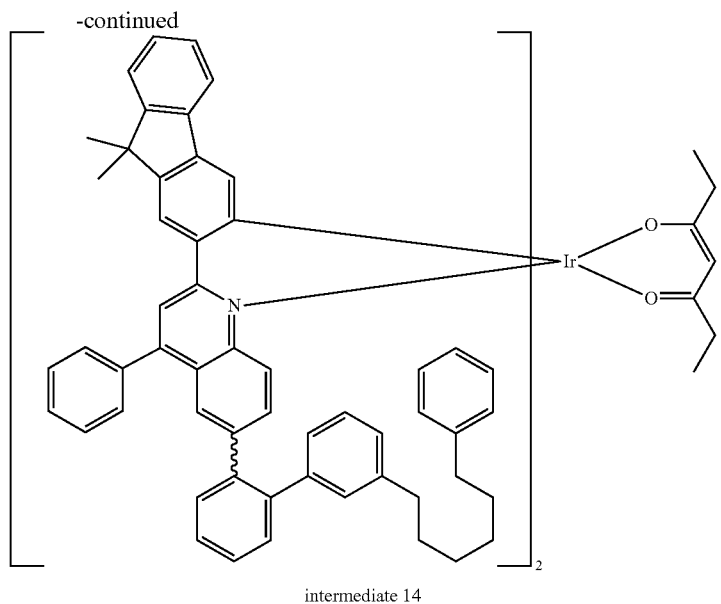

intermediate 14

In a 500 ml round-bottomed flask, 6.98 g of intermediate 13, 2.98 g of 3,5-heptanedione, 4.50 g of sodium carbonate, and 100 ml of 2-ethoxyethanol were placed. The inside was washed with 20 ml of dichloromethane. The flask was placed in an oil bath. The mixture was stirred for 1 hour while the oil temperature was increased to 135° C. Removal of the solvent under reduced pressure gave a residue, which was purified by silica gel column chromatography (neutral silica gel, dichloromethane/hexane) to obtain 4.95 g of intermediate 14 as a deep red solid.

[Chem. 39]

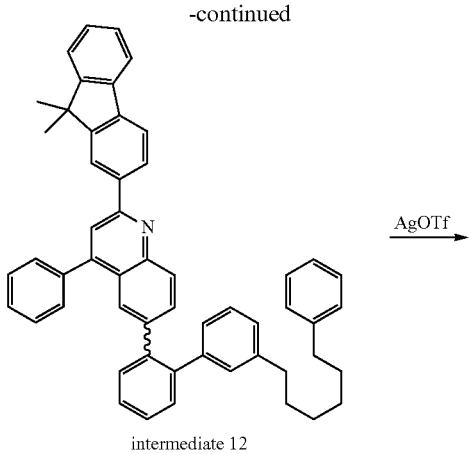

intermediate 12

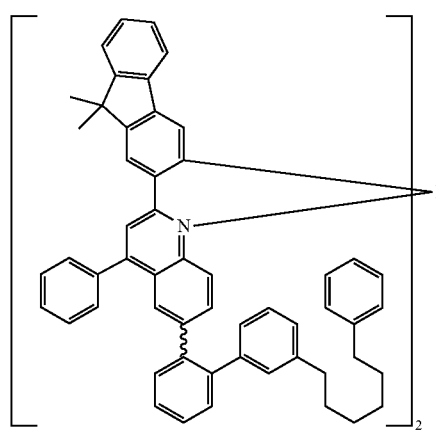

intermediate 14

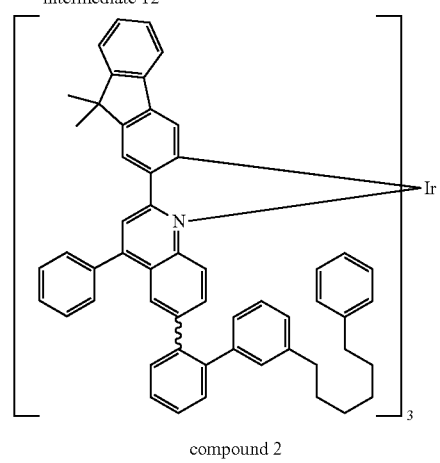

compound 2

In a 100 ml round-bottomed flask, 4.95 g of intermediate 14, 3.98 g of intermediate 12, and 0.2 mL of phenylcyclohexane were placed. The mixture was melted at 240° C. with an aluminum block heater and stirred. Then 0.73 g of silver(I) trifluoromethanesulfonate was added thereto, followed by stirring for 1.5 hours. After cooling, 50 ml of dichloromethane was added for dissolution. Then 30 ml of neutral silica gel was added thereto. The solvent was removed under reduced pressure. The gel on which the product was adsorbed was subjected to silica gel column chromatography (neutral silica gel, dichloromethane/hexane) to obtain 0.95 g of compound 2 as a deep red solid.

Synthesis Example 4: Synthesis of Comparative Compound 2

[Chem. 40]

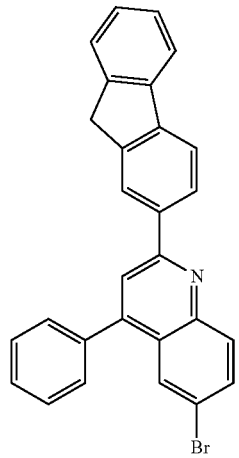

intermediate 1

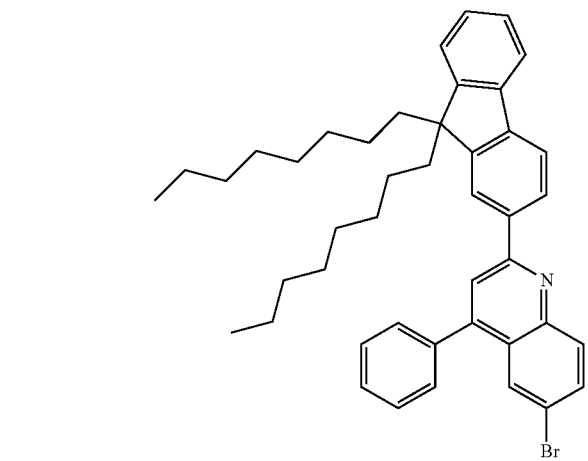

intermediate 15

[Chem. 41]

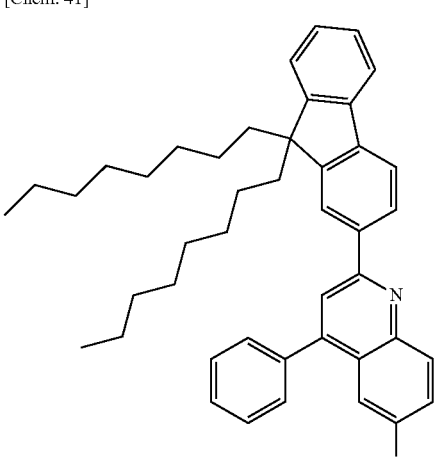

intermediate 15

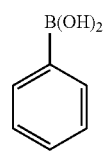

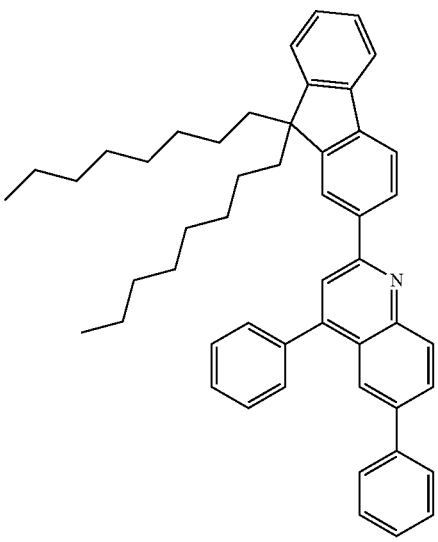

intermediate 16

In a 1 L round-bottomed flask, 15.71 g of intermediate 1, 11.76 g of potassium tert-butoxide, and 200 ml of tetrahydrofuran were placed. The mixture was stirred at room temperature for 30 minutes. The flask was placed in an ice-water bath, followed by addition of 25.13 g of 1-iodooctane. The mixture was stirred for another 30 minutes. Removal of the solvent under reduced pressure gave a residue, which was purified by silica gel column chromatography (neutral silica gel, dichloromethane/hexane) to obtain 18.66 g of intermediate 15 as a yellow amorphous substance.

In a 1 L round-bottomed flask, 18.66 g of intermediate 15, 3.72 g of phenylboronic acid, 2.37 g of tetrakis(triphenylphosphine)palladium(0), 40 ml of a 2 M aqueous solution of tripotassium phosphate, 80 ml of toluene, and 40 ml of ethanol were placed. The mixture was stirred in an oil bath at 100° C. for 2.5 hours, followed by removal of the aqueous phase. Removal of the solvent under reduced pressure gave a residue, which was purified by silica gel column chromatography (neutral silica gel, dichloromethane/hexane) to obtain 18.14 g of intermediate 16 as a yellow amorphous substance.

[Chem. 42]

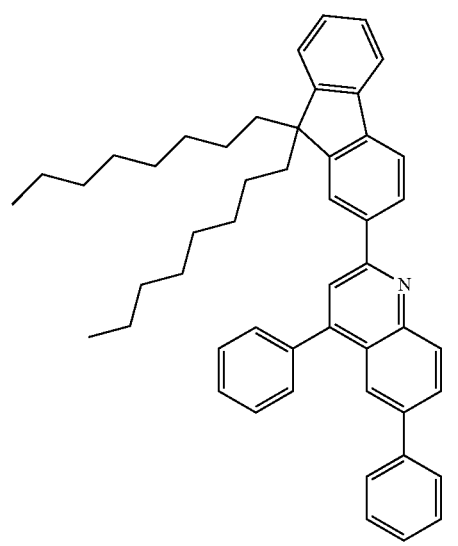

intermediate 16

$$\xrightarrow[\text{IrCl}_3\, n\text{H}_2\text{O}]{\begin{array}{c}1)\ \text{EtOEtOH, water}\\ 2)\ \text{Hacac, Na}_2\text{CO}_3\end{array}}$$

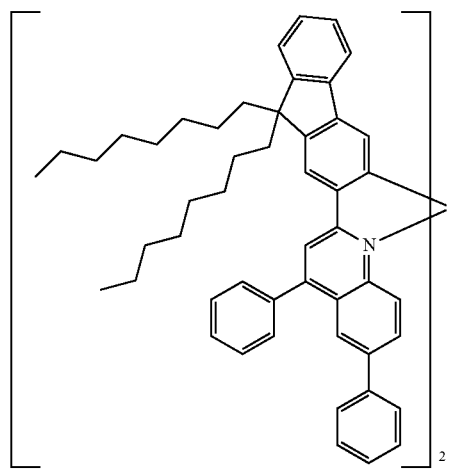

intermediate 17

In a 200 cc round-bottomed flask equipped with a Dimroth condenser having a bypass tube, 6.16 g of intermediate 16 and 1.74 g of iridium chloride n-hydrate (available from Furuya Metal Co., Ltd., iridium content: 51.25 wt %) were placed. Then 80 ml of 2-ethoxyethanol and 20 ml of water were added. The mixture was stirred in an oil bath at 145° C. for 7 hours and then stirred at 160° C. for another 3 hours. During this operation, 50 ml of ethoxyethanol was added 9 hours later. Here, 100 ml of a liquid was removed by distillation through the bypass tube. The reaction mixture was cooled to room temperature, followed by addition of 2.47 g of acetylacetone and 4.75 g of sodium carbonate. The mixture was stirred in an oil bath at 100° C. for 30 minutes. Removal of the solvent under reduced pressure gave a residue, which was purified by silica gel column chromatography (neutral silica gel, dichloromethane/hexane) to obtain 4.71 g of intermediate 17 as a red amorphous solid.

[Chem. 43]

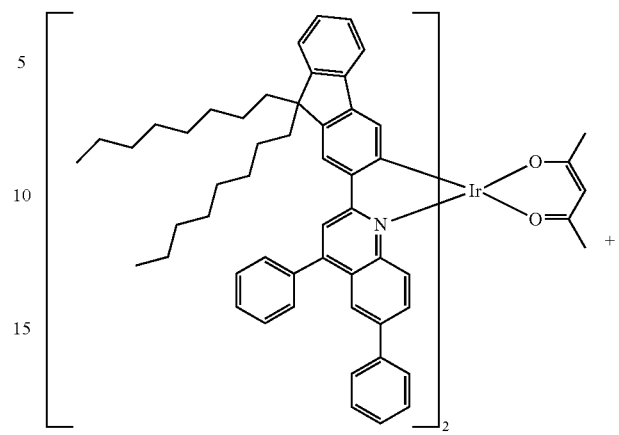

intermediate 17

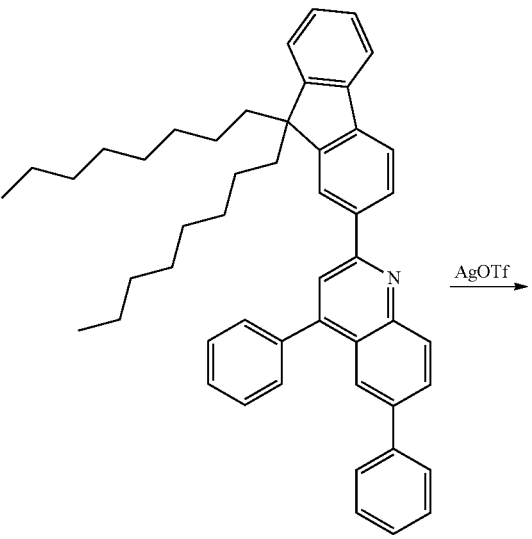

intermediate 16

$\xrightarrow{\text{AgOTf}}$

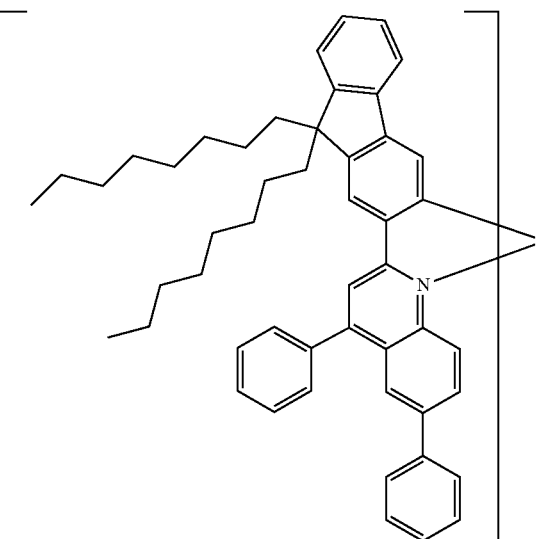

comparative compound 2

In a 100 ml round-bottomed flask, 2.02 g of intermediate 17, 2.78 g of intermediate 16, and 0.15 mL of phenylcyclohexane were placed. The mixture was melted at 240° C. with an aluminum block heater and stirred. Then 0.39 g of silver(I) trifluoromethanesulfonate was added thereto, followed by stirring for 30 minutes. After cooling, 50 ml of dichloromethane was added for dissolution. Then 20 ml of neutral silica gel was added thereto. The solvent was removed under reduced pressure. The gel on which the product was adsorbed was subjected to silica gel column chromatography (neutral silica gel, dichloromethane/hexane) to obtain 1.91 g of comparative compound 2 as a red solid.

Synthesis Example 5: Synthesis of Compound 3

Compound 3 was synthesized in the same method as in the reaction for synthesizing intermediate 4 from intermediate 3 described above, except that acetylacetone was used in place of 3,5-heptanedione.

[Chem. 44]

compound 3

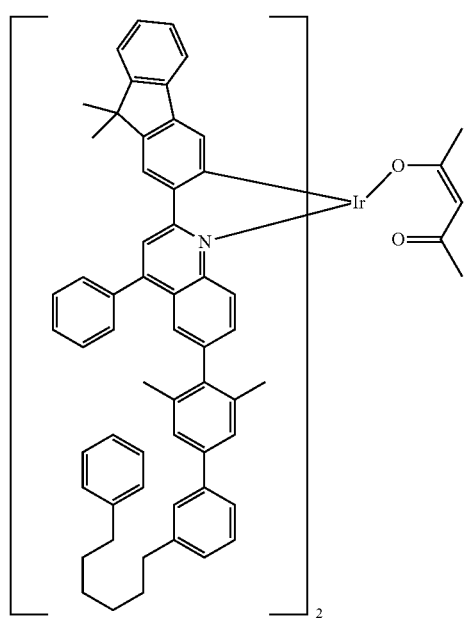

[Chem. 45]

[Comparative Compound 3]

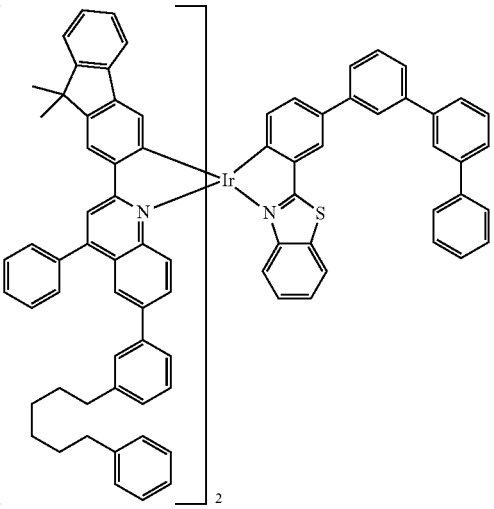

[Chem. 46]

[Reference Compound 1]

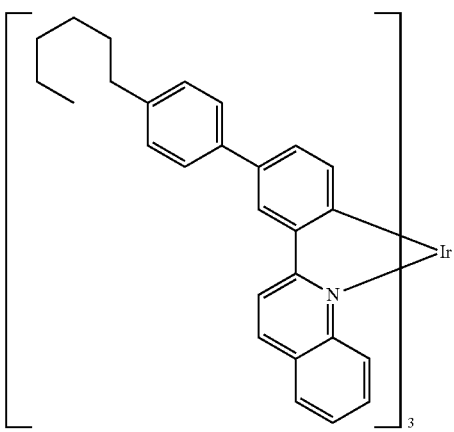

[Chem. 47]

[Reference Compound 2]

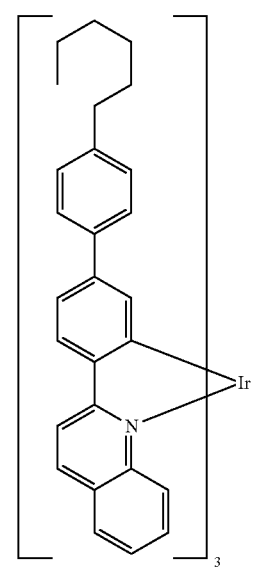

Compounds 1 to 3 and comparative compounds 1 and 2 were each mixed with cyclohexylbenzene as a solvent in an amount of 3% by weight and observed to determine whether these compounds dissolved therein at 70° C. The results indicated that all compounds dissolved and had good solubility in the solvent.

Comparative compound 3 was synthesized from intermediate 8 with reference to a method described in WO2015-087961A1.

Reference compounds 1 to 6 were synthesized with reference to the synthesis examples. They belong to a series of facial-tris-cyclometalated iridium complex compounds that differ only in hydrocarbon substituents on the phenylquinoline ligands. Each of the compounds was used as a reference to indicate the relationship between the spectral half-width and the quantum yield when the emission wavelength was changed with almost no change in the atomic environment near the iridium atom.

[Chem. 48]

[Reference Compound 3]

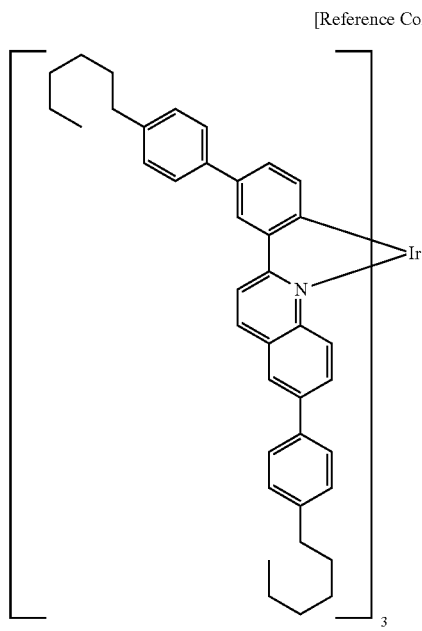

[Chem. 49]

[Reference Compound 4]

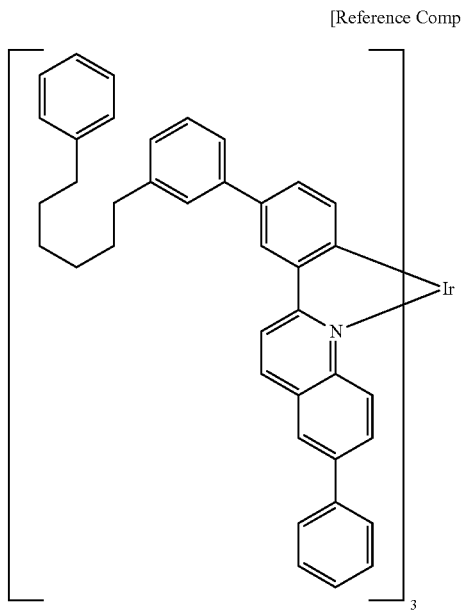

[Chem. 50]

[Reference Compound 5]

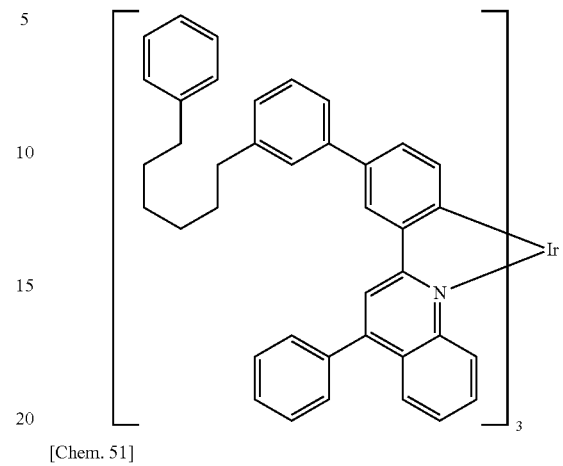

[Chem. 51]

[Reference Compound 6]

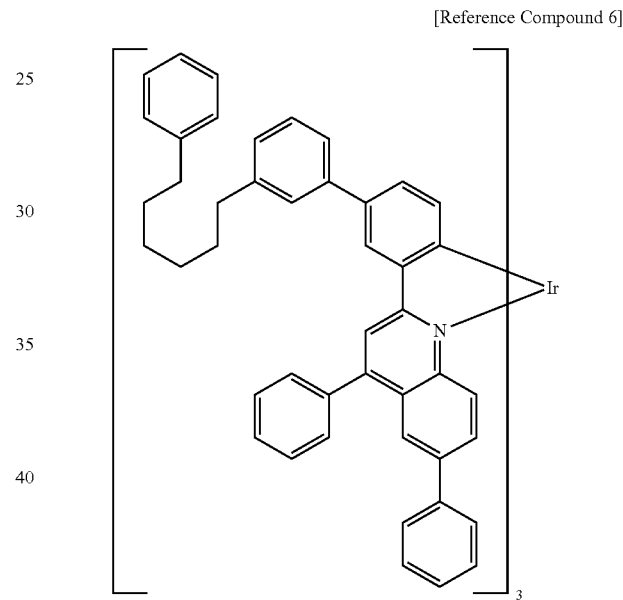

[Measurement of Maximum Emission Wavelength and Half-Width]

Compound 1 was dissolved in 2-methyltetrahydrofuran (available from Aldrich, dehydrated, inhibitor-free) at normal temperature to prepare a solution with a concentration of $1\times10^{-5}$ mol/L. The solution was placed in a quartz cell fitted with a cock composed of Teflon (registered trademark). Nitrogen bubbling was performed for 20 minutes or more. The phosphorescence spectrum thereof was then measured at room temperature. The wavelength at a maximum intensity in the measured phosphorescence spectrum was used a maximum emission wavelength (emission maximum wavelength). The width at half the intensity at the maximum emission wavelength was used as a half-width. The half-width expressed in units of $cm^{-1}$ was obtained as follows: the shorter wavelength above the height of 0.5 and the longer wavelength below the height of 0.5 were read from the data of the spectrum normalized to a converted height of 1, nm was converted into $cm^{-1}$, and the difference therebetween was used as the half-width expressed in units of $cm^{-1}$.

For the measurement of the emission spectrum, the following instruments were used.
Apparatus: C9920-02 organic EL quantum yield spectrometer, available from Hamamatsu Photonics K.K.
Light source: L9799-01 monochromatic light source Detector: PMA-11 multichannel detector
Excitation light: 380 nm
[Measurement of PL Quantum Yield]

The PL quantum yield was measured as the light emission efficiency. The PL quantum yield is an index indicating how efficiently light emission can be obtained with respect to light (energy) absorbed by the material, and was measured with the following instruments as above.
Apparatus: C9920-02 organic EL quantum yield spectrometer, available from Hamamatsu Photonics K.K.
Light source: L9799-01 monochromatic light source
Detector: PMA-11 multichannel detector
Excitation light: 380 nm The half-widths, the maximum emission wavelengths, and the PL quantum yields of compounds 2 and 3, reference compounds 1 to 6, and comparative compounds 1 to 3 were also measured.

Compound 2 has a higher quantum yield than comparative compound 1, for example. The reason for this is presumably that the presence of the aromatic ring and the aralkyl group at the position corresponding to $R^{22}$ causes steric hindrance with respect to the quinoline ring, a twist of the bond, the shortening of the conjugation length, and the suppression of the lengthening of the wavelength more than necessary, similar to compound 1.

In comparative compound 2, $R^{13}$, $R^{17}$, $R^{18}$, and $R^{22}$ are each a hydrogen atom, thus seemingly failing to cause a sufficient twist between the quinoline ring and the benzene rings. As a result, the maximum emission wavelength is longer than those of compounds 1 and 2.

Compound 3 has an extremely narrow half-width and a high quantum yield.

Figure 2:
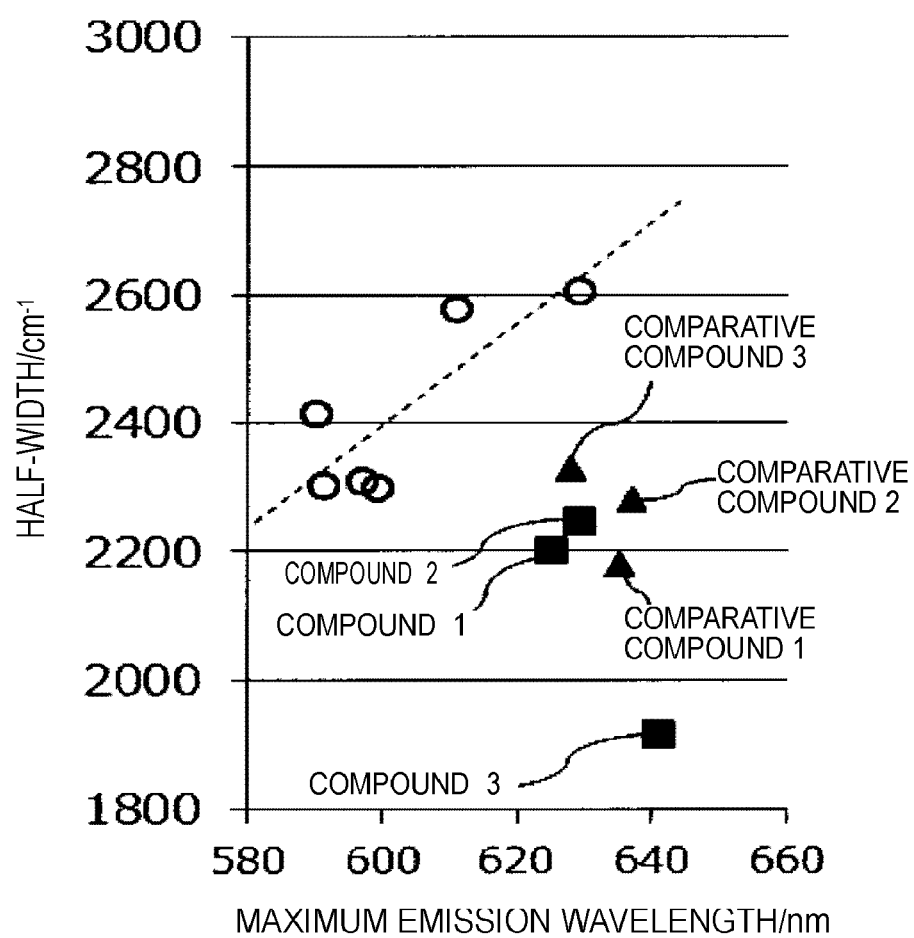
FIG. 2 is a graph illustrating the relationships between the half-widths and the maximum emission wavelengths of compounds 1 to 3, reference compounds 1 to 6, and comparative compounds 1 to 3.

FIG. 2 is a graph illustrating the relationships between the maximum emission wavelengths and the half-widths of compounds 1 to 3, reference compounds 1 to 6, and comparative compounds 1 to 3. The broken line indicates an approximate straight line between the maximum emission wavelengths and the half-widths of a family of reference compounds 1 to 6. In the family of reference compounds 1

TABLE 1

| | Maximum emission wavelength nm | PL quantum yield | Half-width nm | Half-width $cm^{-1}$ |
|---|---|---|---|---|
| Reference compound 1 | 590 | 0.71 | 89 | 2414 |
| Reference compound 2 | 591 | 0.71 | 85 | 2305 |
| Reference compound 3 | 599 | 0.73 | 87 | 2300 |
| Reference compound 4 | 597 | 0.77 | 87 | 2310 |
| Reference compound 5 | 611 | 0.68 | 103 | 2579 |
| Reference compound 6 | 629 | 0.67 | 107 | 2609 |
| Compound 1 | 625 | 0.73 | 90 | 2202 |
| Compound 2 | 629 | 0.72 | 94 | 2247 |
| Compound 3 | 641 | 0.72 | 82 | 1918 |
| Comparative compound 1 | 635 | 0.7 | 92 | 2180 |
| Comparative compound 2 | 637 | 0.65 | 98 | 2278 |
| Comparative compound 3 | 628 | 0.74 | 97 | 2328 |

Table 1 presents the half-widths, the maximum emission wavelengths, and the PL quantum yields of compounds 1 to 3, reference compounds 1 to 6, and comparative compounds 1 to 3. It can be seen that compounds 1 to 3 and reference compounds 1 to 3 have sufficiently narrow half-widths in the region of a maximum emission wavelength of 620 nm or more, which can be used as a red light-emitting material. It can be seen that the PL quantum yield has the same level as before. It was found that the incorporation of the aromatic group at the predetermined position of quinoline results in the iridium complex compound whose quantum yield is not significantly decreased even when the compound is coordinated with three fluorene ligands while keeping the half-width narrow.

Compound 1 has a particularly small half-width and a high PL quantum yield as compared with comparative compounds 1 and 2, and can be used to produce an excellent top emission-type light-emitting element. Compound 1 has a higher quantum yield than comparative compound 1, for example. The reason for this is presumably that the presence of the alkyl groups (methyl groups) as $R^{18}$ and $R^{22}$ in formula (2) causes steric hindrance with respect to the quinoline ring, a twist of the bond, the shortening of the conjugation length, and the suppression of the lengthening of the wavelength more than necessary. Additionally, the reason for the high solubility is presumably that the aromatic ring and the aralkyl group are present at the position corresponding to $R^{20}$ in the twisted moiety.

to 6 each having a phenylquinoline-based ligand that does not have a fluorene structure, a longer maximum emission wavelength tends to result in a wider half-width. In contrast, compounds 1 to 3 and comparative compounds 1 to 3 have narrow half-widths in the region of a maximum emission wavelength of 620 nm or more, which is suitable as a red light-emitting material, and thus are suitable for a top emission-type multilayer structure. The results indicate that compounds 1 to 3 are particularly excellent in terms of both of the half-width and the maximum emission wavelength.

Figure 3:
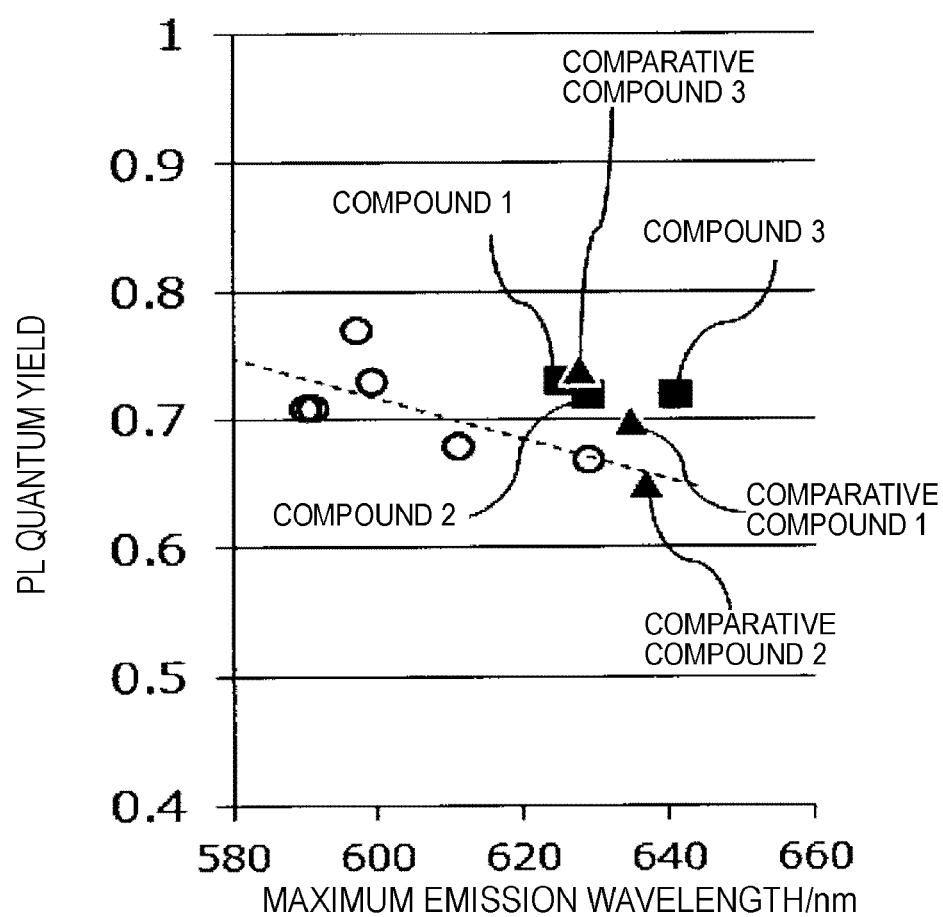
FIG. 3 is a graph illustrating the relationships between the PL quantum yields and the maximum emission wavelengths of compounds 1 to 3, reference compounds 1 to 6, and comparative compounds 1 to 3.

FIG. 3 is a graph illustrating the relationships between the maximum emission wavelengths and the PL quantum yields of compounds 1 to 3, reference compounds 1 to 6, and comparative compounds 1 to 3. In long-wavelength red light-emitting materials, typically, the PL quantum yields tend to be low according to the energy gap law. The broken line indicates an approximate straight line between the maximum emission wavelengths and the PL quantum yields of the family of reference compounds 1 to 6. In the family of reference compounds 1 to 6 each having a phenylquinoline-based ligand that does not have a fluorene structure, a longer maximum emission wavelength tends to result in a lower PL quantum yield. In contrast, it can be seen that compounds 1 to 3 have high PL quantum yields even in the region of a maximum emission wavelength of 620 nm or more.

The above-described results demonstrate that compounds 1 to 3 have narrow half-widths and PL quantum yields comparable to conventional compounds in the region of a maximum emission wavelength of 620 nm or more and thus exhibit excellent light-emitting performance when used for a top emission-type multilayer structure.

[Comparison of T1-Level Maximum Emission Wavelength]

A comparison was made of the maximum emission wavelength between compound 4 and comparative compound 4 below on the basis of calculation using the density functional theory. The excitation energy of the T level was determined from the energy difference between the energy of the ground state and the energy of the T1-level state, and the T1-level maximum emission wavelength was determined. Table 2 presents the results.

[Chem. 52]

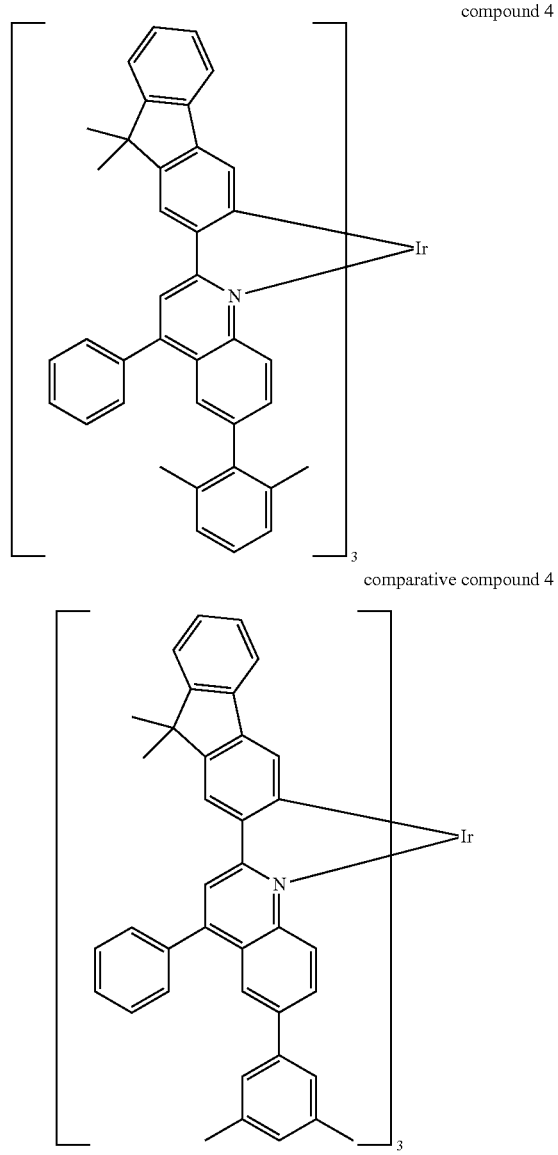

compound 4 comparative compound 4

Compound 4 can be synthesized in the same manner as compound 1, except that phenylboronic acid is used in place of 3-(6-phenyl-n-hexyl)phenylboronic acid in the synthesis of intermediate 6 and 2-bromo-6-phenyl-m-xylene that does not have the 6-phenyl-n-hexyl group is synthesized in place of intermediate 6.

The calculation of the emission wavelength, i.e., the T1 level, was performed using Gaussian 09, Revision B.01, which is commercially available electronic state calculation software (see below *). The quantum chemical calculation was performed using the density functional theory and the B3LYP functional. The following basis function was used: regarding an Ir atom, a function with a diffuse d function (exponent=0.07) and an f function (exponent=0.938) added to a function modified by Coutry and Hall using optimized coefficients for the 6p orbital based on LANL2DZ (references: J. Comp. Chem. 17. 1359(1996) and J. Am. Chem. Soc. 126.13044(2004)). Regarding other atoms, 6-31G was used. The structure optimization calculations in the ground state and the T1-level state were performed using b3LYP. The excitation energy of the T level was determined from the energy difference between the energy of the ground state and the energy of the T1-level state, and the maximum emission wavelength at the T1-level was determined.

*Gaussian 09, Revision B.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr. , J. E. Peralta, F. Ogliaro, M. Bearpark, J. J. Heyd, E. Brothers, K. N. Kudin, V. N. Staroverov, T. Keith, R. Kobayashi, J. Normand, K. Raghavachari, A. Rendell, J. C. Burant, S. S. Iyengar, J. Tomasi, M. Cossi, N. Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, O. Farkas, J. B. Foresman, J. V. Ortiz, J. Cioslowski, and D. J. Fox, Gaussian, Inc. , Wallingford CT, 2010.

TABLE 2

| | T1 maximum emission wavelength nm |
|---|---|
| Compound 4 | 614 |
| Comparative compound 4 | 622 |

The calculation results indicate that the maximum emission wavelength of compound 4 is shorter than that of comparative compound 4. The reason for this is presumably that the presence of the substituents serving as $R^{18}$ and $R^{22}$ results in steric hindrance between the quinoline ring and the benzene ring to cause a sufficient twist.

While the present invention has been described in detail using a specific embodiment, it should be apparent to those skilled in the art that various modifications can be made without departing from the spirit and scope of the present invention.

The present application is based on Japanese Patent Application No. 2019-002398 filed on Jan. 10, 2019 and Japanese Patent Application No. 2019-184629 filed on Oct. 7, 2019, which are incorporated herein by reference in their entirety.

REFERENCE SIGNS LIST 1 substrate
2 anode
3 hole injection layer
4 hole transport layer
5 light-emitting layer
6 hole blocking layer
7 electron transport layer
8 electron injection layer
9 cathode
10 organic electroluminescent element

The invention claimed is:

1. An iridium complex compound represented by formula (5):

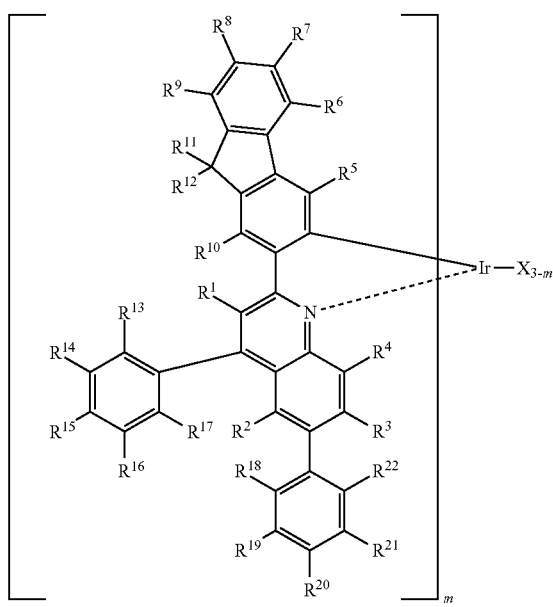

formula (5)

where in formula (5), Ir represents an iridium atom,
$R^1$ to $R^{12}$ each independently represent a hydrogen atom or a substituent;
adjacent $R^1$ to $R^{12}$ are optionally bonded together to form a ring;
$R^{13}$ to $R^{22}$ each independently represent a hydrogen atom or a substituent;
adjacent $R^{13}$ to $R^{22}$ are optionally bonded together to form a ring;
X represents a bidentate ligand;
m represents an integer of 1 to 3, and;
at least one of $R^{13}$, $R^{17}$, $R^{18}$, and $R^{22}$ represents a substituent other than a hydrogen atom.

2. The iridium complex compound according to claim 1, wherein formula (5) is represented by formula (2):

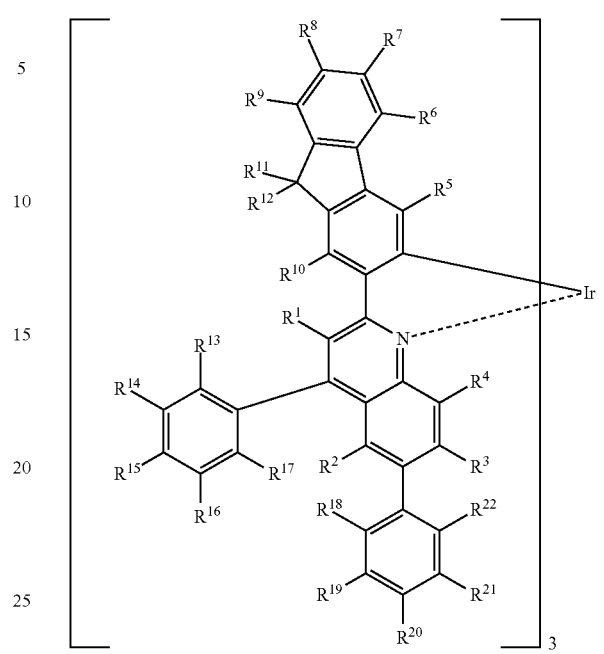

formula (2)

where in formula (2), $R^1$ to $R^{22}$ are defined the same as in formula (5).

3. The iridium complex compound according to claim 1, wherein $R^1$ to $R^{12}$, and $R^{13}$ to $R^{22}$ are as follows:
$R^1$ to $R^{12}$ are each independently selected from D, F, Cl, Br, I, —N(R')$_2$, —CN, —NO$_2$, —OH, —COOR', —C(=O) R', —C(=O) NR', —P(=O)(R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;
the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(=R')=C(—R')—, —C≡C—, —Si(—R')$_2$, —C(=O)—, —NR'—, —O—, —S—, —CONR'— or a divalent aromatic group, one or more hydrogen atoms in these groups are each optionally replaced with D, F, Cl, Br, I, or —CN;
the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R';

adjacent $R^1$ to $R^{12}$ are optionally bonded together to form a ring;

each R' is independently selected from a hydrogen atom, D, F, Cl, Br, I, —N(R")$_2$, —CN, —NO$_2$, —Si(R")$_3$, —B(OR")$_2$, —C(=O)R", —P(=O)(R")$_2$, —S(=O)$_2$R", —OSO$_2$R", a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R", one —CH$_2$— group or two or more non-adjacent —CH$_2$— groups in these groups are each optionally replaced with —C(—R")=C(—R")—, —C≡C—, —Si(—R")$_2$—, —C(=O)—, —NR"—, —O—, —S—, —CONR"—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R";

two or more R' are optionally bonded together to form an aliphatic, aromatic, or heteroaromatic, monocyclic or fused ring;

each R" is independently selected from a hydrogen atom, D, F, —CN, an aliphatic hydrocarbon group having 1 to 20 carbon atoms, an aromatic group having 3 to 20 carbon atoms, and a heteroaromatic group having 1 to 20 carbon atoms;

two or more R" are optionally bonded together to form an aliphatic, aromatic, or heteroaromatic, monocyclic or fused ring; and $R^{13}$ to $R^{22}$ are each independently a hydrogen atom or a substituent represented by R'.

4. The iridium complex compound according to claim 1, wherein in formula (5), two or more adjacent $R^1$ to $R^{10}$, $R^{11}$ and $R^{12}$, two or more adjacent $R^{13}$ to $R^{17}$, or two or more adjacent $R^{18}$ to $R^{22}$ are bonded together to form an aliphatic, aromatic, or heteroaromatic, monocyclic or fused ring.

5. The iridium complex compound according to claim 1, wherein formula (5) is represented by formula (6):

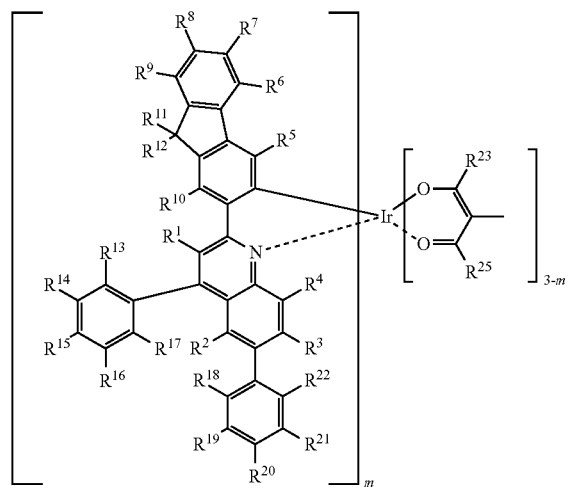

formula (6)

wherein $R^1$ to $R^{12}$ are each independently selected from D, F, Cl, Br, I, —N(R')$_2$, —CN, —NO$_2$, —OH, —COOR', —C(=O)R', —C(=O)NR', —P(=O)(R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R' one —CH$_2$— group or two or more non-adjacent —CH$_2$— groups in these groups are each optionally replaced with —C(—R')=C(—R')—, —C≡C—, —Si(—R')$_2$, —C(=O)—, —NR'—, —O—, —S—, —CONR'— or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R';

adjacent $R^1$ to $R^{12}$ are optionally bonded together to form a ring;

each R' is independently selected from a hydrogen atom, D, F, Cl, Br, I, —N(R")$_2$, —CN, —NO$_2$, —Si(R")$_3$, —B(OR")$_2$, —C(=O)R", —P(=O)(R")$_2$, —S(=O)$_2$R", —OSO$_2$R", a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

the alkyl group, the alkoxy group, the alkylthio group, the alkenyl group, and the alkynyl group are each optionally substituted with one or more of R", one —CH$_2$— group or two or more non-adjacent —CH$_2$— groups in these groups are each optionally replaced with —C(—R")=C(—R")—, —C≡C—, —Si(—R")$_2$—, —C(=O)—, —NR"—, —O—, —S—, —CONR"—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R";

two or more R' are optionally bonded together to form an aliphatic, aromatic, or heteroaromatic, monocyclic or fused ring;

each R" is independently selected from a hydrogen atom, D, F, —CN, an aliphatic hydrocarbon group having 1 to 20 carbon atoms, an aromatic group having 3 to 20 carbon atoms, and a heteroaromatic group having 1 to 20 carbon atoms;

two or more R" are optionally bonded together to form an aliphatic, aromatic, or heteroaromatic, monocyclic or fused ring; and $R^{13}$ to $R^{22}$ are each independently a hydrogen atom or a substituent represented by R', $R^{23}$ and $R^{25}$ are each independently selected from —N(R')$_2$, —COOR', —C(=O)R', —C(=O)NR', —P(=O)(R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

$R^{24}$ is selected from a hydrogen atom, D, —N(R')$_2$, —COOR', —C(=O)R', —C(=O)NR', —P(=O)(R')$_2$, —S(=O)R', —S(=O)$_2$R', —OS(=O)$_2$R', a linear, branched, or cyclic alkyl group having 1 to 30 carbon atoms, a linear, branched, or cyclic alkoxy group having 1 to 30 carbon atoms, a linear, branched, or cyclic alkylthio group having 1 to 30 carbon atoms, a linear, branched, or cyclic alkenyl group having 2 to 30 carbon atoms, a linear, branched, or cyclic alkynyl group having 2 to 30 carbon atoms, an aromatic group having 5 to 60 carbon atoms, a heteroaromatic group having 5 to 60 carbon atoms, an aryloxy group having 5 to 40 carbon atoms, an arylthio group having 5 to 40 carbon atoms, an aralkyl group having 5 to 60 carbon atoms, a heteroaralkyl group having 5 to 60 carbon atoms, a diarylamino group having 10 to 40 carbon atoms, an arylheteroarylamino group having 10 to 40 carbon atoms, and a diheteroarylamino group having 10 to 40 carbon atoms;

two or more adjacent $R^{23}$ to $R^{25}$ are optionally bonded together to form an aliphatic, aromatic, or heteroaromatic, monocyclic or fused ring;

the alkyl group, the alkoxy group, the alkylthio group, the alkenyl group, and the alkynyl group are each optionally substituted with one or more of R', one —CH$_2$— group or two or more non-adjacent —CH$_2$— groups in these groups are each optionally replaced with —C(—R')=C(—R')—, —C≡C—, —Si(—R')$_2$, —C(=O)—, —NR'—, —O—, —S—, —CONR'—, or a divalent aromatic group, one or more hydrogen atoms in these groups are each optionally replaced with D, F, Cl, Br, I, or —CN;

the aromatic group, the heteroaromatic group, the aryloxy group, the arylthio group, the aralkyl group, the heteroaralkyl group, the diarylamino group, the arylheteroarylamino group, and the diheteroarylamino group are each independently optionally substituted with one or more of R'.

6. The iridium complex compound according to claim 1, wherein at least one of $R^1$ to $R^4$ and $R^{13}$ to $R^{22}$ in formula (5) contains an alkyl group having 4 to 30 carbon atoms or an aralkyl group having 5 to 30 carbon atoms.

7. The iridium complex compound according to claim 1, wherein at least one or more of the substituents $R^{13}$, $R^{17}$, $R^{18}$, and $R^{22}$ in formula (5) each optionally have an alkyl group having 1 to 4 carbon atoms or an optionally substituted aromatic group.

8. The iridium complex compound according to claim 7, wherein each of the substituents $R^{18}$ and $R^{22}$ in formula (5) is an alkyl group having 1 to 4 carbon atoms.

9. The iridium complex compound according to claim 1, wherein at least one or more of the substituents $R^{14}$, $R^{15}$, $R^{16}$, $R^{19}$, $R^{20}$, and $R^{21}$ in formula (5) is an alkyl group, an optionally substituted aromatic ring group, or an aralkyl group.

10. The iridium complex compound according to claim 9, wherein at least one or more of the substituents $R^{14}$, $R^{15}$, $R^{16}$, $R^{19}$, $R^{20}$, and $R^{21}$ in formula (5) are each a substituted aromatic ring group, and the substituent is an aralkyl group.

11. The iridium complex compound according to claim 10, wherein the iridium complex compound is represented by formula (3):

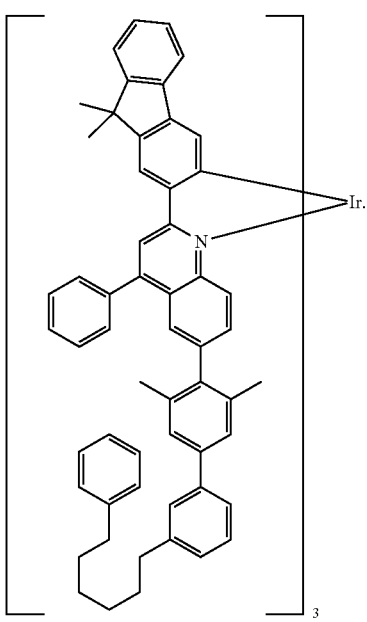

formula (3)

12. The iridium complex compound according to claim 1, wherein at least one or more of the substituents $R^{13}$, $R^{17}$, $R^{18}$, and $R^{22}$ in formula (5) are each a substituted aromatic ring group, and the substituent is an aralkyl group.

13. The iridium complex compound according to claim 12, wherein the iridium complex compound is represented by formula (4);

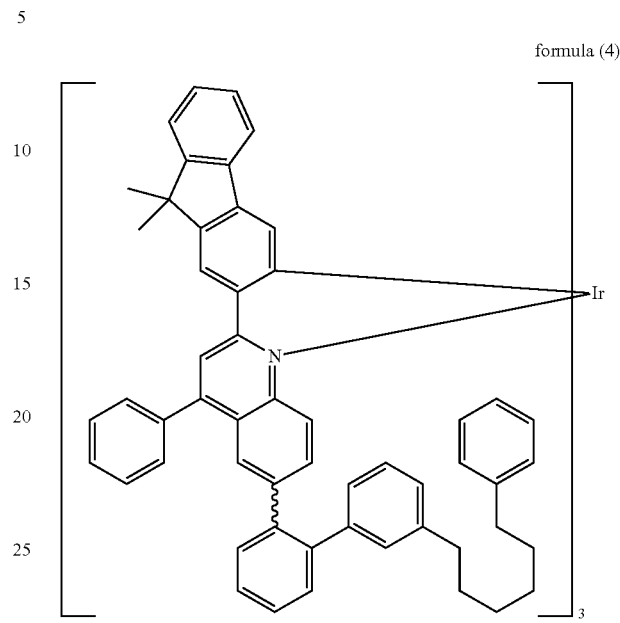

formula (4)

where in formula (4), a wiggly line indicates a mixture of rotamers.

* * * * *